(12) United States Patent
Clarke et al.

(10) Patent No.: US 7,132,264 B2
(45) Date of Patent: Nov. 7, 2006

(54) HUMAN SERPIN POLYPEPTIDES

(75) Inventors: Howard R. G. Clarke, Seattle, WA (US); Robert F. DuBose, Bellevue, WA (US); Steven R. Wiley, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 11/219,282

(22) Filed: Sep. 2, 2005

(65) Prior Publication Data

US 2006/0018892 A1    Jan. 26, 2006

Related U.S. Application Data

(62) Division of application No. 10/094,944, filed on Mar. 8, 2002, now Pat. No. 6,958,387.

(60) Provisional application No. 60/274,522, filed on Mar. 8, 2001, provisional application No. 60/274,519, filed on Mar. 8, 2001.

(51) Int. Cl.
*C07K 1/00* (2006.01)
*C07H 21/02* (2006.01)
*C07H 21/04* (2006.01)
*C12N 1/20* (2006.01)
*C12N 5/00* (2006.01)

(52) U.S. Cl. ............ 435/69.2; 536/23.1; 536/23.5; 435/252.3; 435/325; 435/320.1; 530/350

(58) Field of Classification Search ............ 530/350; 536/23.5, 23.1; 435/320.1, 69.1, 252.3, 325
See application file for complete search history.

(56) References Cited

U.S. PATENT DOCUMENTS

| 6,583,269 | B1 | 6/2003 | Hu et al. |
| 2003/0096952 | A1 | 5/2003 | Majumder et al. |
| 2003/0224498 | A1 | 12/2003 | Hu et al. |
| 2003/0236389 | A1 | 12/2003 | Shimkets et al. |
| 2004/0033504 | A1 | 2/2004 | Agarwal et al. |

FOREIGN PATENT DOCUMENTS

| EP | 1433848 A1 | 6/2004 |
| WO | WO 2001074851 A2 | 10/2001 |
| WO | WO 2001074851 A3 | 10/2001 |
| WO | WO 2001075067 A2 | 10/2001 |
| WO | WO 2001075067 A3 | 10/2001 |
| WO | WO 2001081363 A1 | 11/2001 |
| WO | WO 2002057452 A2 | 7/2002 |
| WO | WO 2002057452 A3 | 7/2002 |

OTHER PUBLICATIONS

Hillier, L. et al., GenBank Database Accession No. AA242969, Nov. 27, 1996.
Schick C. et al., "Cross-class inhibition of the cysteine proteinases cathepsins K, L, and S by the serpin squamous cell carcinoma antigen 1: a kinetic analysis", *Biochemistry* 37(15): 5258-5266, Apr. 14, 1998.
Silverman G. A. et al., "SCCA1 and SCCA2 are proteinase inhibitors that map to the serpin cluster at 18q21.3", *Tumour Biol* 19(6): 480-487, Nov.-Dec. 1998.
Spring P. et al., "Identification and cDNA cloning of *headpin*, a novel differentially expressed serpin that maps to chromosome 18q", *Biochem Biophys Res Comm* 264: 299-304, Oct. 14, 1999.
Carninci and Hayashizaki (Reference 1), Carninci et al. (Reference 2), The RIKEN Genome Exploration Research Group Phaese II Team and FANTOM Consortium (Reference 3), and Adachi J. et al. (Reference 4), GenBank Database Accession No. AK009018, Feb. 8, 2001.
Askew, Y. S. et al. (Reference 1) and Silverman and Askew (Reference 2), GenBank Database Accession No. AF411191, Sep. 19, 2001.
Majumder, K. et al., GenBank Database Accession No. CAD13083, Nov. 30, 2001.
Askew, Y. S. et al., "SERPINB12 is a novel member of the human ov-serpin family that is widely expressed and inhibits trypsin-like serine proteinases", *J Biol Chem* 276(52): 49320-49330, Dec. 28, 2001.

*Primary Examiner*—Rebecca E. Prouty
*Assistant Examiner*—Malgorzata A. Walicka
(74) *Attorney, Agent, or Firm*—Susan E. Lingenfelter

(57) ABSTRACT

This invention relates to Thypin, a new member of the human serpin polypeptide family, methods of making Thypin polypeptides and using these polypeptides to treat various medical disorders and to methods of screening for compounds that agonize or antagonize Thypin polypeptide activities.

8 Claims, 1 Drawing Sheet

SEQUENCE LISTING

<160> NUMBER OF SEQ ID NOS: 35

<210> SEQ ID NO 1
<211> LENGTH: 1278
<212> TYPE: DNA

-continued

```
<213> ORGANISM: Homo sapiens
<220> FEATURE:
<221> NAME/KEY: CDS
<222> LOCATION: (1)..(1278)
<223> OTHER INFORMATION:

<400> SEQUENCE: 1
```

| | | | | | | | | | | | | | | | | |
|---|---|---|---|---|---|---|---|---|---|---|---|---|---|---|---|---|
| atg | gac | tct | ctt | gtt | aca | gca | aac | acc | aaa | ttt | tgc | ttt | gat | ctt | ttt | 48 |
| Met | Asp | Ser | Leu | Val | Thr | Ala | Asn | Thr | Lys | Phe | Cys | Phe | Asp | Leu | Phe | |
| 1 | | | | 5 | | | | | 10 | | | | | 15 | | |
| caa | gag | ata | ggc | aaa | gat | gat | cgt | cat | aaa | aac | ata | ttt | ttc | tct | ccc | 96 |
| Gln | Glu | Ile | Gly | Lys | Asp | Asp | Arg | His | Lys | Asn | Ile | Phe | Phe | Ser | Pro | |
| | | | 20 | | | | | 25 | | | | | 30 | | | |
| ctg | agc | ctc | tca | gct | gcc | ctt | ggt | atg | gta | cgc | ttg | ggt | gct | aga | agt | 144 |
| Leu | Ser | Leu | Ser | Ala | Ala | Leu | Gly | Met | Val | Arg | Leu | Gly | Ala | Arg | Ser | |
| | 35 | | | | | 40 | | | | | 45 | | | | | |
| gac | agt | gca | cat | cag | att | gat | gag | gta | cta | cac | ttc | aac | gaa | ttt | tcc | 192 |
| Asp | Ser | Ala | His | Gln | Ile | Asp | Glu | Val | Leu | His | Phe | Asn | Glu | Phe | Ser | |
| 50 | | | | | 55 | | | | | 60 | | | | | | |
| cag | aat | gaa | agc | aaa | gaa | cct | gac | cct | tgt | ctg | aaa | agc | aac | aaa | caa | 240 |
| Gln | Asn | Glu | Ser | Lys | Glu | Pro | Asp | Pro | Cys | Leu | Lys | Ser | Asn | Lys | Gln | |
| 65 | | | | | 70 | | | | | 75 | | | | | 80 | |
| aaa | gtg | ctg | gct | gac | agc | tct | ctg | gag | ggg | cag | aaa | aaa | acg | aca | gag | 288 |
| Lys | Val | Leu | Ala | Asp | Ser | Ser | Leu | Glu | Gly | Gln | Lys | Lys | Thr | Thr | Glu | |
| | | | | 85 | | | | | 90 | | | | | 95 | | |
| cct | ctg | gat | cag | cag | gct | ggg | tcc | tta | aac | aat | gag | agc | gga | ctg | gtc | 336 |
| Pro | Leu | Asp | Gln | Gln | Ala | Gly | Ser | Leu | Asn | Asn | Glu | Ser | Gly | Leu | Val | |
| | | | 100 | | | | | 105 | | | | | 110 | | | |
| agc | tgc | tac | ttt | ggg | cag | ctt | ctc | tcc | aaa | tta | gac | agg | atc | aag | act | 384 |
| Ser | Cys | Tyr | Phe | Gly | Gln | Leu | Leu | Ser | Lys | Leu | Asp | Arg | Ile | Lys | Thr | |
| | 115 | | | | | 120 | | | | | 125 | | | | | |
| gat | tac | aca | ctg | agt | att | gcc | aac | agg | ctt | tat | gga | gag | cag | gaa | ttc | 432 |
| Asp | Tyr | Thr | Leu | Ser | Ile | Ala | Asn | Arg | Leu | Tyr | Gly | Glu | Gln | Glu | Phe | |
| 130 | | | | | 135 | | | | | 140 | | | | | | |
| cca | atc | tgt | cag | gaa | tac | tta | gat | ggt | gtg | att | caa | ttt | tac | cac | acg | 480 |
| Pro | Ile | Cys | Gln | Glu | Tyr | Leu | Asp | Gly | Val | Ile | Gln | Phe | Tyr | His | Thr | |
| 145 | | | | | 150 | | | | | 155 | | | | | 160 | |
| acg | att | gaa | agt | gtt | gat | ttc | caa | aaa | aac | cct | gaa | aaa | tcc | aga | caa | 528 |
| Thr | Ile | Glu | Ser | Val | Asp | Phe | Gln | Lys | Asn | Pro | Glu | Lys | Ser | Arg | Gln | |
| | | | | 165 | | | | | 170 | | | | | 175 | | |
| gag | att | aac | ttc | tgg | gtt | gaa | tgt | caa | tcc | caa | ggt | aaa | atc | aag | gaa | 576 |
| Glu | Ile | Asn | Phe | Trp | Val | Glu | Cys | Gln | Ser | Gln | Gly | Lys | Ile | Lys | Glu | |
| | | | 180 | | | | | 185 | | | | | 190 | | | |
| ctc | ttc | agc | aag | gac | gct | att | aat | gct | gag | act | gtg | ctg | gta | ctg | gtg | 624 |
| Leu | Phe | Ser | Lys | Asp | Ala | Ile | Asn | Ala | Glu | Thr | Val | Leu | Val | Leu | Val | |
| | | 195 | | | | | 200 | | | | | 205 | | | | |
| aat | gct | gtt | tac | ttc | aag | gcc | aaa | tgg | gaa | aca | tac | ttt | gac | cat | gaa | 672 |
| Asn | Ala | Val | Tyr | Phe | Lys | Ala | Lys | Trp | Glu | Thr | Tyr | Phe | Asp | His | Glu | |
| 210 | | | | | 215 | | | | | 220 | | | | | | |
| aac | acg | gtg | gat | gca | cct | ttc | tgt | cta | aat | gcg | aat | gaa | aac | aag | agt | 720 |
| Asn | Thr | Val | Asp | Ala | Pro | Phe | Cys | Leu | Asn | Ala | Asn | Glu | Asn | Lys | Ser | |
| 225 | | | | | 230 | | | | | 235 | | | | | 240 | |
| gtg | aag | atg | atg | acg | caa | aaa | ggc | ctc | tac | aga | att | ggc | ttc | ata | gag | 768 |
| Val | Lys | Met | Met | Thr | Gln | Lys | Gly | Leu | Tyr | Arg | Ile | Gly | Phe | Ile | Glu | |
| | | | | 245 | | | | | 250 | | | | | 255 | | |
| gag | gtg | aag | gca | cag | atc | ctg | gaa | atg | agg | tac | acc | aag | ggg | aag | ctc | 816 |
| Glu | Val | Lys | Ala | Gln | Ile | Leu | Glu | Met | Arg | Tyr | Thr | Lys | Gly | Lys | Leu | |
| | | | 260 | | | | | 265 | | | | | 270 | | | |
| agc | atg | ttc | gtg | ctg | ctg | cca | tct | cac | tct | aaa | gat | aac | ctg | aag | ggt | 864 |
| Ser | Met | Phe | Val | Leu | Leu | Pro | Ser | His | Ser | Lys | Asp | Asn | Leu | Lys | Gly | |
| | 275 | | | | | 280 | | | | | 285 | | | | | |

-continued

```
ctg gaa gag ctt gaa agg aaa atc acc tat gaa aaa atg gtg gcc tgg      912
Leu Glu Glu Leu Glu Arg Lys Ile Thr Tyr Glu Lys Met Val Ala Trp
    290                 295                 300 agc agc tca gaa aac atg tca gaa gaa tcg gtg gtc ctg tcc ttc ccc      960
Ser Ser Ser Glu Asn Met Ser Glu Glu Ser Val Val Leu Ser Phe Pro
305                 310                 315                 320 cgg ttc acc ctg gaa gac agc tat gat ctc aat tcc att tta caa gac     1008
Arg Phe Thr Leu Glu Asp Ser Tyr Asp Leu Asn Ser Ile Leu Gln Asp
                325                 330                 335 atg ggc att acg gat atc ttt gat gaa acg agg gct gat ctt act gga     1056
Met Gly Ile Thr Asp Ile Phe Asp Glu Thr Arg Ala Asp Leu Thr Gly
            340                 345                 350 atc tct cca agt ccc aat ttg tac ttg tca aaa att atc cac aaa acc     1104
Ile Ser Pro Ser Pro Asn Leu Tyr Leu Ser Lys Ile Ile His Lys Thr
        355                 360                 365 ttt gtg gag gtg gat gaa aac ggt acc cag gca gct gca gcc act ggg     1152
Phe Val Glu Val Asp Glu Asn Gly Thr Gln Ala Ala Ala Ala Thr Gly
    370                 375                 380 gct gtt gtc tcg gaa agg tca cta cga tct tgg gtg gag ttt aat gcc     1200
Ala Val Val Ser Glu Arg Ser Leu Arg Ser Trp Val Glu Phe Asn Ala
385                 390                 395                 400 aac cac cct ttt ctc ttt ttc att aga cac aac aaa acc caa acc att     1248
Asn His Pro Phe Leu Phe Phe Ile Arg His Asn Lys Thr Gln Thr Ile
                405                 410                 415 ctc ttt tat ggc agg gtc tgc tct cct taa                             1278
Leu Phe Tyr Gly Arg Val Cys Ser Pro
            420                 425
```

<210> SEQ ID NO 2
<211> LENGTH: 425
<212> TYPE: PRT
<213> ORGANISM: Homo sapiens

<400> SEQUENCE: 2

```
Met Asp Ser Leu Val Thr Ala Asn Thr Lys Phe Cys Phe Asp Leu Phe
1               5                   10                  15

Gln Glu Ile Gly Lys Asp Asp Arg His Lys Asn Ile Phe Phe Ser Pro
            20                  25                  30

Leu Ser Leu Ser Ala Ala Leu Gly Met Val Arg Leu Gly Ala Arg Ser
        35                  40                  45

Asp Ser Ala His Gln Ile Asp Glu Val Leu His Phe Asn Glu Phe Ser
    50                  55                  60

Gln Asn Glu Ser Lys Glu Pro Asp Pro Cys Leu Lys Ser Asn Lys Gln
65                  70                  75                  80

Lys Val Leu Ala Asp Ser Ser Leu Glu Gly Gln Lys Lys Thr Thr Glu
                85                  90                  95

Pro Leu Asp Gln Gln Ala Gly Ser Leu Asn Asn Glu Ser Gly Leu Val
            100                 105                 110

Ser Cys Tyr Phe Gly Gln Leu Leu Ser Lys Leu Asp Arg Ile Lys Thr
        115                 120                 125

Asp Tyr Thr Leu Ser Ile Ala Asn Arg Leu Tyr Gly Glu Gln Glu Phe
    130                 135                 140

Pro Ile Cys Gln Glu Tyr Leu Asp Gly Val Ile Gln Phe Tyr His Thr
145                 150                 155                 160

Thr Ile Glu Ser Val Asp Phe Gln Lys Asn Pro Glu Lys Ser Arg Gln
                165                 170                 175

Glu Ile Asn Phe Trp Val Glu Cys Gln Ser Gln Gly Lys Ile Lys Glu
```

```
                 180                 185                 190
Leu Phe Ser Lys Asp Ala Ile Asn Ala Glu Thr Val Leu Val Leu Val
            195                 200                 205
Asn Ala Val Tyr Phe Lys Ala Lys Trp Glu Thr Tyr Phe Asp His Glu
        210                 215                 220
Asn Thr Val Asp Ala Pro Phe Cys Leu Asn Ala Asn Glu Asn Lys Ser
225                 230                 235                 240
Val Lys Met Met Thr Gln Lys Gly Leu Tyr Arg Ile Gly Phe Ile Glu
                245                 250                 255
Glu Val Lys Ala Gln Ile Leu Glu Met Arg Tyr Thr Lys Gly Lys Leu
            260                 265                 270
Ser Met Phe Val Leu Pro Ser His Ser Lys Asp Asn Leu Lys Gly
        275                 280                 285
Leu Glu Glu Leu Glu Arg Lys Ile Thr Tyr Glu Lys Met Val Ala Trp
        290                 295                 300
Ser Ser Ser Glu Asn Met Ser Glu Glu Ser Val Val Leu Ser Phe Pro
305                 310                 315                 320
Arg Phe Thr Leu Glu Asp Ser Tyr Asp Leu Asn Ser Ile Leu Gln Asp
                325                 330                 335
Met Gly Ile Thr Asp Ile Phe Asp Glu Thr Arg Ala Asp Leu Thr Gly
            340                 345                 350
Ile Ser Pro Ser Pro Asn Leu Tyr Leu Ser Lys Ile Ile His Lys Thr
        355                 360                 365
Phe Val Glu Val Asp Glu Asn Gly Thr Gln Ala Ala Ala Thr Gly
        370                 375                 380
Ala Val Val Ser Glu Arg Ser Leu Arg Ser Trp Val Glu Phe Asn Ala
385                 390                 395                 400
Asn His Pro Phe Leu Phe Phe Ile Arg His Asn Lys Thr Gln Thr Ile
                405                 410                 415
Leu Phe Tyr Gly Arg Val Cys Ser Pro
            420                 425

<210> SEQ ID NO 3
<211> LENGTH: 26
<212> TYPE: DNA
<213> ORGANISM: Artificial Sequence
<220> FEATURE:
<223> OTHER INFORMATION: oligonucleotide

<400> SEQUENCE: 3
tggttttaga tcgttataag ttttac                                          26

<210> SEQ ID NO 4
<211> LENGTH: 30
<212> TYPE: DNA
<213> ORGANISM: Artificial Sequence
<220> FEATURE:
<223> OTHER INFORMATION: oligonucleotide

<400> SEQUENCE: 4
ctccagctcc aaagtactag acactgctcc                                      30

<210> SEQ ID NO 5
<211> LENGTH: 38
<212> TYPE: DNA
<213> ORGANISM: Artificial Sequence
<220> FEATURE:
<223> OTHER INFORMATION: oligonucleotide
```

-continued

```
<400> SEQUENCE: 5
atactagtag tatggactct cttgttacag caaacacc                              38

<210> SEQ ID NO 6
<211> LENGTH: 40
<212> TYPE: DNA
<213> ORGANISM: Artificial Sequence
<220> FEATURE:
<223> OTHER INFORMATION: oligonucleotide

<400> SEQUENCE: 6
tagcggccgc ttaaggagag cagaccctgc cataaaagag                            40

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
atggactctc ttgttacagc                                                  20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
ctctccataa agcctgttgg                                                  20

<210> SEQ ID NO 9
<211> LENGTH: 379
<212> TYPE: PRT
<213> ORGANISM: Homo sapiens

<400> SEQUENCE: 9
```

Met Glu Gln Leu Ser Ser Ala Asn Thr Arg Phe Ala Leu Asp Leu Phe
1               5                   10                  15

Leu Ala Leu Ser Glu Asn Asn Pro Ala Gly Asn Ile Phe Ile Ser Pro
            20                  25                  30

Phe Ser Ile Ser Ser Ala Met Ala Met Val Phe Leu Gly Thr Arg Gly
        35                  40                  45

Asn Thr Ala Ala Gln Leu Ser Lys Thr Phe His Phe Asn Thr Val Glu
    50                  55                  60

Glu Val His Ser Arg Phe Gln Ser Leu Asn Ala Asp Ile Asn Lys Arg
65                  70                  75                  80

Gly Ala Ser Tyr Ile Leu Lys Leu Ala Asn Arg Leu Tyr Gly Glu Lys
                85                  90                  95

Thr Tyr Asn Phe Leu Pro Glu Phe Leu Val Ser Thr Gln Lys Thr Tyr
            100                 105                 110

Gly Ala Asp Leu Ala Ser Val Asp Phe Gln His Ala Ser Glu Asp Ala
        115                 120                 125

Arg Lys Thr Ile Asn Gln Trp Val Lys Gly Gln Thr Glu Gly Lys Ile
    130                 135                 140

Pro Glu Leu Leu Ala Ser Gly Met Val Asp Asn Met Thr Lys Leu Val
145                 150                 155                 160

Leu Val Asn Ala Ile Tyr Phe Lys Gly Asn Trp Lys Asp Lys Phe Met

-continued

```
                165                 170                 175
Lys Glu Ala Thr Thr Asn Ala Pro Phe Arg Leu Asn Lys Lys Asp Arg
            180                 185                 190

Lys Thr Val Lys Met Met Tyr Gln Lys Lys Phe Ala Tyr Gly Tyr
        195                 200                 205

Ile Glu Asp Leu Lys Cys Arg Val Leu Glu Leu Pro Tyr Gln Gly Glu
        210                 215                 220

Glu Leu Ser Met Val Ile Leu Leu Pro Asp Asp Ile Glu Asp Glu Ser
225                 230                 235                 240

Thr Gly Leu Lys Lys Ile Glu Glu Gln Leu Thr Leu Glu Lys Leu His
            245                 250                 255

Glu Trp Thr Lys Pro Glu Asn Leu Asp Phe Ile Glu Val Asn Val Ser
        260                 265                 270

Leu Pro Arg Phe Lys Leu Glu Glu Ser Tyr Thr Leu Asn Ser Asp Leu
        275                 280                 285

Ala Arg Leu Gly Val Gln Asp Leu Phe Asn Ser Ser Lys Ala Asp Leu
        290                 295                 300

Ser Gly Met Ser Gly Ala Arg Asp Ile Phe Ile Ser Lys Ile Val His
305                 310                 315                 320

Lys Ser Phe Val Glu Val Asn Glu Glu Gly Thr Glu Ala Ala Ala Ala
            325                 330                 335

Thr Ala Gly Ile Ala Thr Phe Cys Met Leu Met Pro Glu Glu Asn Phe
            340                 345                 350

Thr Ala Asp His Pro Phe Leu Phe Phe Ile Arg His Asn Ser Ser Gly
            355                 360                 365

Ser Ile Leu Phe Leu Gly Arg Phe Ser Ser Pro
        370                 375

<210> SEQ ID NO 10
<211> LENGTH: 415
<212> TYPE: PRT
<213> ORGANISM: Homo sapiens

<400> SEQUENCE: 10

Met Glu Asp Leu Cys Val Ala Asn Thr Leu Phe Ala Leu Asn Leu Phe
1               5                   10                  15

Lys His Leu Ala Lys Ala Ser Pro Thr Gln Asn Leu Phe Leu Ser Pro
            20                  25                  30

Trp Ser Ile Ser Ser Thr Met Ala Met Val Tyr Met Gly Ser Arg Gly
        35                  40                  45

Ser Thr Glu Asp Gln Met Ala Lys Val Leu Gln Phe Asn Glu Val Gly
    50                  55                  60

Ala Asn Ala Val Thr Pro Met Thr Pro Glu Asn Phe Thr Ser Cys Gly
65                  70                  75                  80

Phe Met Gln Gln Ile Gln Lys Gly Ser Tyr Pro Asp Ala Ile Leu Gln
                85                  90                  95

Ala Gln Ala Ala Asp Lys Ile His Ser Ser Phe Arg Ser Leu Ser Ser
            100                 105                 110

Ala Ile Asn Ala Ser Thr Gly Asn Tyr Leu Leu Glu Ser Val Asn Lys
        115                 120                 125

Leu Phe Gly Glu Lys Ser Ala Ser Phe Arg Glu Glu Tyr Ile Arg Leu
    130                 135                 140

Cys Gln Lys Tyr Tyr Ser Ser Glu Pro Gln Ala Val Asp Phe Leu Glu
145                 150                 155                 160
```

```
Cys Ala Glu Glu Ala Arg Lys Lys Ile Asn Ser Trp Val Lys Thr Gln
                165                 170                 175

Thr Lys Gly Lys Ile Pro Asn Leu Leu Pro Glu Gly Ser Val Asp Gly
            180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Pro Asp Glu Ile
            260                 265                 270

Ala Asp Val Ser Thr Gly Leu Glu Leu Leu Glu Ser Glu Ile Thr Tyr
        275                 280                 285

Asp Lys Leu Asn Lys Trp Thr Ser Lys Asp Lys Met Ala Glu Asp Glu
290                 295                 300

Val Glu Val Tyr Ile Pro Gln Phe Lys Leu Glu Glu His Tyr Glu Leu
305                 310                 315                 320

Arg Ser Ile Leu Arg Ser Met Gly Met Glu Asp Ala Phe Asn Lys Gly
                325                 330                 335

Arg Ala Asn Phe Ser Gly Met Ser Glu Arg Asn Asp Leu Phe Leu Ser
            340                 345                 350

Glu Val Phe His Gln Ala Met Val Asp Val Asn Glu Glu Gly Thr Glu
        355                 360                 365

Ala Ala Ala Gly Thr Gly Gly Val Met Thr Gly Arg Thr Gly His Gly
370                 375                 380

Gly Pro Gln Phe Val Ala Asp His Pro Phe Leu Phe Leu Ile Met His
385                 390                 395                 400

Lys Ile Thr Asn Cys Ile Leu Phe Phe Gly Arg Phe Ser Ser Pro
                405                 410                 415

<210> SEQ ID NO 11
<211> LENGTH: 397
<212> TYPE: PRT
<213> ORGANISM: Homo sapiens

<400> SEQUENCE: 11

Met Asp Ser Leu Ala Thr Ser Ile Asn Gln Phe Ala Leu Glu Leu Ser
1               5                   10                  15

Lys Lys Leu Ala Glu Ser Ala Gln Gly Lys Asn Ile Phe Phe Ser Ser
            20                  25                  30

Trp Ser Ile Ser Thr Ser Leu Thr Ile Val Tyr Leu Gly Ala Lys Gly
        35                  40                  45

Thr Thr Ala Ala Gln Met Ala Gln Val Leu Gln Phe Asn Arg Asp Gln
    50                  55                  60

Gly Val Lys Cys Asp Pro Glu Ser Glu Lys Lys Arg Lys Met Glu Phe
65                  70                  75                  80

Asn Leu Ser Asn Ser Glu Glu Ile His Ser Asp Phe Gln Thr Leu Ile
                85                  90                  95

Ser Glu Ile Leu Lys Pro Asn Asp Asp Tyr Leu Leu Lys Thr Ala Asn
            100                 105                 110

Ala Ile Tyr Gly Glu Lys Thr Tyr Ala Phe His Asn Lys Tyr Leu Glu
        115                 120                 125
```

```
Asp Met Lys Thr Tyr Phe Gly Ala Glu Pro Gln Pro Val Asn Phe Val
    130                 135                 140

Glu Ala Ser Asp Gln Ile Arg Lys Asp Ile Asn Ser Trp Val Glu Arg
145                 150                 155                 160

Gln Thr Glu Gly Lys Ile Gln Asn Leu Leu Pro Asp Asp Ser Val Asp
                165                 170                 175

Ser Thr Thr Arg Met Ile Leu Val Asn Ala Leu Tyr Phe Lys Gly Ile
            180                 185                 190

Trp Glu His Gln Phe Leu Val Gln Asn Thr Thr Glu Lys Pro Phe Arg
        195                 200                 205

Ile Asn Glu Thr Thr Ser Lys Pro Val Gln Met Met Phe Met Lys Lys
    210                 215                 220

Leu His Ile Phe His Ile Glu Lys Pro Lys Ala Val Gly Leu Gln
225                 230                 235                 240

Leu Tyr Tyr Lys Ser Arg Asp Leu Ser Leu Ile Leu Leu Pro Glu
                245                 250                 255

Asp Ile Asn Gly Leu Glu Gln Leu Glu Lys Ala Ile Thr Tyr Glu Lys
            260                 265                 270

Leu Asn Glu Trp Thr Ser Ala Asp Met Met Glu Leu Tyr Glu Val Gln
        275                 280                 285

Leu His Leu Pro Lys Phe Lys Leu Glu Asp Ser Tyr Asp Leu Lys Ser
    290                 295                 300

Thr Leu Ser Ser Met Gly Met Ser Asp Ala Phe Ser Gln Ser Lys Ala
305                 310                 315                 320

Asp Phe Ser Gly Met Ser Ser Ala Arg Asn Leu Phe Leu Ser Asn Val
                325                 330                 335

Phe His Lys Ala Phe Val Glu Ile Asn Glu Gln Gly Thr Glu Ala Ala
            340                 345                 350

Ala Gly Ser Gly Ser Glu Ile Asp Ile Arg Ile Arg Val Pro Ser Ile
        355                 360                 365

Glu Phe Asn Ala Asn His Pro Phe Leu Phe Phe Ile Arg His Asn Lys
    370                 375                 380

Thr Asn Thr Ile Leu Phe Tyr Gly Arg Leu Cys Ser Pro
385                 390                 395

<210> SEQ ID NO 12
<211> LENGTH: 390
<212> TYPE: PRT
<213> ORGANISM: Homo sapiens

<400> SEQUENCE: 12

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
                20                  25                  30

Ser Ile Thr Ser Ala Leu Gly Met Val Leu Leu Gly Ala Lys Asp Asn
            35                  40                  45

Thr Ala Gln Gln Ile Lys Lys Val Leu His Phe Asp Gln Val Thr Glu
50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
```

-continued

```
                 100                 105                 110
Tyr Leu Phe Leu Gln Glu Tyr Leu Asp Ala Ile Lys Lys Phe Tyr Gln
            115                 120                 125

Thr Ser Val Glu Ser Val Asp Phe Ala Asn Ala Pro Glu Glu Ser Arg
130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Glu Lys Phe Trp Pro Asn Lys Asn Thr Tyr Lys
            195                 200                 205

Ser Ile Gln Met Met Arg Gln Tyr Thr Ser Phe His Phe Ala Ser Leu
        210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
        275                 280                 285

Val Glu Glu Ser Tyr Asp Leu Lys Asp Thr Leu Arg Thr Met Gly Met
        290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                325                 330                 335

Thr Glu Glu Gly Ala Glu Ala Ala Ala Ala Thr Ala Val Val Gly Phe
            340                 345                 350

Gly Ser Ser Pro Ala Ser Thr Asn Glu Glu Phe His Cys Asn His Pro
        355                 360                 365

Phe Leu Phe Phe Ile Arg Gln Asn Lys Thr Asn Ser Ile Leu Phe Tyr
370                 375                 380

Gly Arg Phe Ser Ser Pro
385                 390

<210> SEQ ID NO 13
<211> LENGTH: 390
<212> TYPE: PRT
<213> ORGANISM: Homo sapiens

<400> SEQUENCE: 13

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
            20                  25                  30

Ser Ile Thr Ser Ala Leu Gly Met Val Leu Leu Gly Ala Lys Asp Asn
        35                  40                  45

Thr Ala Gln Gln Ile Ser Lys Val Leu His Phe Asp Gln Val Thr Glu
    50                  55                  60

Asn Thr Thr Glu Lys Ala Ala Thr Tyr His Val Asp Arg Ser Gly Asn
65                  70                  75                  80
```

```
Val His His Gln Phe Gln Lys Leu Leu Thr Glu Phe Asn Lys Ser Thr
                85                  90                  95
Asp Ala Tyr Glu Leu Lys Ile Ala Asn Lys Leu Phe Gly Glu Lys Thr
            100                 105                 110
Tyr Gln Phe Leu Gln Glu Tyr Leu Asp Ala Ile Lys Lys Phe Tyr Gln
        115                 120                 125
Thr Ser Val Glu Ser Thr Asp Phe Ala Asn Ala Pro Glu Glu Ser Arg
    130                 135                 140
Lys Lys Ile Asn Ser Trp Val Glu Ser Gln Thr Asn Glu Lys Ile Lys
145                 150                 155                 160
Asn Leu Phe Pro Asp Gly Thr Ile Gly Asn Asp Thr Thr Leu Val Leu
                165                 170                 175
Val Asn Ala Ile Tyr Phe Lys Gly Gln Trp Glu Asn Lys Phe Lys Lys
            180                 185                 190
Glu Asn Thr Lys Glu Glu Lys Phe Trp Pro Asn Lys Asn Thr Tyr Lys
        195                 200                 205
Ser Val Gln Met Met Arg Gln Tyr Asn Ser Phe Asn Phe Ala Leu Leu
    210                 215                 220
Glu Asp Val Gln Ala Lys Val Leu Glu Ile Pro Tyr Lys Gly Lys Asp
225                 230                 235                 240
Leu Ser Met Ile Val Leu Leu Pro Asn Glu Ile Asp Gly Leu Gln Lys
                245                 250                 255
Leu Glu Glu Lys Leu Thr Ala Glu Lys Leu Met Glu Trp Thr Ser Leu
            260                 265                 270
Gln Asn Met Arg Glu Thr Cys Val Asp Leu His Leu Pro Arg Phe Lys
        275                 280                 285
Met Glu Glu Ser Tyr Asp Leu Lys Asp Thr Leu Arg Thr Met Gly Met
    290                 295                 300
Val Asn Ile Phe Asn Gly Asp Ala Asp Leu Ser Gly Met Thr Trp Ser
305                 310                 315                 320
His Gly Leu Ser Val Ser Lys Val Leu His Lys Ala Phe Val Glu Val
                325                 330                 335
Thr Glu Glu Gly Val Glu Ala Ala Ala Thr Ala Val Val Val
            340                 345                 350
Glu Leu Ser Ser Pro Ser Thr Asn Glu Glu Phe Cys Cys Asn His Pro
        355                 360                 365
Phe Leu Phe Phe Ile Arg Gln Asn Lys Thr Asn Ser Ile Leu Phe Tyr
    370                 375                 380
Gly Arg Phe Ser Ser Pro
385                 390

<210> SEQ ID NO 14
<211> LENGTH: 617
<212> TYPE: PRT
<213> ORGANISM: Homo sapiens
<220> FEATURE:
<221> NAME/KEY: MISC_FEATURE
<222> LOCATION: (90)..(90)
<223> OTHER INFORMATION: unsure
<220> FEATURE:
<221> NAME/KEY: MISC_FEATURE
<222> LOCATION: (215)..(215)
<223> OTHER INFORMATION: unsure
<220> FEATURE:
<221> NAME/KEY: MISC_FEATURE
<222> LOCATION: (225)..(225)
<223> OTHER INFORMATION: unsure
<220> FEATURE:
<221> NAME/KEY: MISC_FEATURE
```

```
<222> LOCATION: (232)..(233)
<223> OTHER INFORMATION: unsure
<220> FEATURE:
<221> NAME/KEY: MISC_FEATURE
<222> LOCATION: (289)..(289)
<223> OTHER INFORMATION: unsure
<220> FEATURE:
<221> NAME/KEY: MISC_FEATURE
<222> LOCATION: (309)..(309)
<223> OTHER INFORMATION: unsure
<220> FEATURE:
<221> NAME/KEY: MISC_FEATURE
<222> LOCATION: (318)..(318)
<223> OTHER INFORMATION: unsure
<220> FEATURE:
<221> NAME/KEY: MISC_FEATURE
<222> LOCATION: (322)..(322)
<223> OTHER INFORMATION: unsure
<220> FEATURE:
<221> NAME/KEY: MISC_FEATURE
<222> LOCATION: (331)..(332)
<223> OTHER INFORMATION: unsure
<220> FEATURE:
<221> NAME/KEY: MISC_FEATURE
<222> LOCATION: (367)..(367)
<223> OTHER INFORMATION: unsure
<220> FEATURE:
<221> NAME/KEY: MISC_FEATURE
<222> LOCATION: (369)..(369)
<223> OTHER INFORMATION: unsure
<220> FEATURE:
<221> NAME/KEY: MISC_FEATURE
<222> LOCATION: (374)..(374)
<223> OTHER INFORMATION: unsure
<220> FEATURE:
<221> NAME/KEY: MISC_FEATURE
<222> LOCATION: (378)..(378)
<223> OTHER INFORMATION: unsure
<220> FEATURE:
<221> NAME/KEY: MISC_FEATURE
<222> LOCATION: (425)..(425)
<223> OTHER INFORMATION: unsure
<220> FEATURE:
<221> NAME/KEY: MISC_FEATURE
<222> LOCATION: (430)..(430)
<223> OTHER INFORMATION: unsure

<400> SEQUENCE: 14

Met Gly Ser Leu Ser Thr Ala Asn Val Glu Phe Cys Leu Asp Val Phe
1               5                   10                  15

Lys Glu Leu Asn Ser Asn Asn Ile Gly Asp Asn Ile Phe Phe Ser Ser
            20                  25                  30

Leu Ser Leu Leu Tyr Ala Leu Ser Met Val Leu Leu Gly Ala Arg Gly
        35                  40                  45

Glu Thr Ala Glu Gln Leu Glu Lys Val Leu His Phe Ser His Thr Val
    50                  55                  60

Asp Ser Leu Lys Pro Gly Phe Lys Asp Ser Pro Lys Cys Ser Gln Ala
65                  70                  75                  80

Gly Arg Ile His Ser Glu Phe Gly Val Xaa Phe Ser Gln Ile Asn Gln
                85                  90                  95

Pro Asp Ser Asn Cys Thr Leu Ser Ile Ala Asn Arg Leu Tyr Gly Thr
            100                 105                 110

Lys Thr Met Ala Phe His Gln Gln Tyr Leu Ser Cys Ser Glu Lys Trp
        115                 120                 125

Tyr Gln Ala Arg Leu Gln Thr Val Asp Phe Glu Gln Ser Thr Glu Glu
    130                 135                 140

Thr Arg Lys Thr Ile Asn Ala Trp Val Glu Asn Lys Thr Asn Gly Lys
145                 150                 155                 160
```

```
Val Ala Asn Leu Phe Gly Lys Ser Thr Ile Asp Pro Ser Ser Val Met
            165                 170                 175

Val Leu Val Asn Ala Ile Tyr Phe Lys Gly Gln Trp Gln Asn Lys Phe
            180                 185                 190

Gln Val Arg Glu Thr Val Lys Ser Pro Phe Gln Leu Ser Glu Val Ser
            195                 200                 205

Ile Leu Phe Ser Asp Ser Xaa Gln Met Leu Glu Asp Thr Ile Ile Ile
            210                 215                 220

Xaa Gly Gln Phe Arg Lys Met Xaa Xaa Phe Ser Glu Asn Ile Gly Leu
225                 230                 235                 240

Gly Phe Cys Trp Phe Leu Leu Tyr Phe Leu Gln Ile Phe Ile Phe
            245                 250                 255

Pro Leu Leu Ser Asp Asn Asn Phe Tyr His Arg Ala Pro Asn Trp Arg
            260                 265                 270

Leu Gly Ile Leu Arg Phe Ser Gly Arg Gly Glu Asn Pro Phe Phe Ser
            275                 280                 285

Xaa Arg Ser Leu Gly Leu Phe Phe Pro Tyr Ile Leu Trp Leu Cys Ser
            290                 295                 300

Pro Ala Ala His Xaa Gly Tyr Leu Cys Tyr Phe Phe Xaa Arg Val
305                 310                 315                 320

Ser Xaa Gly Lys Ile Lys Lys Lys Met Ile Xaa Xaa Tyr Ile Leu Phe
            325                 330                 335

Leu Pro Thr Lys Ile Met Leu Ala Lys Asn Pro Asp Phe Val Phe Gly
            340                 345                 350

Arg Pro Ser Tyr Leu Tyr Ile Leu Leu Glu Gln Phe Ser Leu Xaa Pro
            355                 360                 365

Xaa Leu Ile Leu Asn Xaa Lys Asn Gly Xaa Pro Leu Gln Arg Glu Val
            370                 375                 380

Ile Arg Asn Leu Leu Cys Ser Phe Tyr Phe Thr His Ala Phe Arg Val
385                 390                 395                 400

Phe Met Gln Ile Ser Val Leu Arg Lys Val Ile Ser Thr His Thr Cys
            405                 410                 415

Ala Leu Thr Tyr Val Ser Ile Leu Xaa Ser Phe Ser Ser Xaa Gln Gly
            420                 425                 430

Lys Asn Val Thr Val Glu Met Met Tyr Gln Ile Gly Thr Phe Lys Leu
            435                 440                 445

Ala Phe Val Lys Glu Pro Gln Met Gln Val Leu Glu Leu Pro Tyr Val
450                 455                 460

Asn Asn Lys Leu Ser Met Ile Ile Leu Leu Pro Val Gly Ile Ala Asn
465                 470                 475                 480

Leu Lys Gln Ile Glu Lys Gln Leu Asn Ser Gly Thr Phe His Glu Trp
            485                 490                 495

Thr Ser Ser Asn Met Met Glu Arg Glu Val Glu Val His Leu Pro
            500                 505                 510

Arg Phe Lys Leu Glu Thr Lys Tyr Glu Leu Asn Ser Leu Leu Lys Ser
            515                 520                 525

Leu Gly Val Thr Asp Leu Phe Asn Gln Val Lys Ala Asp Leu Ser Gly
            530                 535                 540

Met Ser Pro Thr Lys Gly Leu Tyr Leu Ser Lys Ala Ile His Lys Ser
545                 550                 555                 560

Tyr Leu Asp Val Ser Glu Glu Gly Thr Glu Ala Ala Ala Thr Gly
            565                 570                 575

Asp Ser Ile Ala Val Lys Ser Leu Pro Met Arg Ala Gln Phe Lys Ala
```

```
                 580                 585                 590
Asn His Pro Phe Leu Phe Phe Ile Arg His Thr His Thr Asn Thr Ile
            595                 600                 605

Leu Phe Cys Gly Lys Leu Ala Ser Pro
    610                 615

<210> SEQ ID NO 15
<211> LENGTH: 37
<212> TYPE: PRT
<213> ORGANISM: Artificial Sequence
<220> FEATURE:
<223> OTHER INFORMATION: Synthetic fusion protein

<400> SEQUENCE: 15

Met Glu Thr Asp Thr Leu Leu Leu Trp Val Leu Leu Leu Trp Val Pro
1               5                   10                  15

Gly Ser Thr Gly Asp Tyr Lys Asp Glu Gly Ser His His His His
            20                  25                  30

His Gly Thr Ser Ser
        35

<210> SEQ ID NO 16
<211> LENGTH: 22
<212> TYPE: DNA
<213> ORGANISM: Artificial Sequence
<220> FEATURE:
<223> OTHER INFORMATION: oligonucleotide

<400> SEQUENCE: 16
aacgacagag cctctggatc ag                                            22

<210> SEQ ID NO 17
<211> LENGTH: 21
<212> TYPE: DNA
<213> ORGANISM: Artificial Sequence
<220> FEATURE:
<223> OTHER INFORMATION: oligonucleotide

<400> SEQUENCE: 17
gagaagctgc ccaaagtagc a                                             21

<210> SEQ ID NO 18
<211> LENGTH: 29
<212> TYPE: DNA
<213> ORGANISM: Artificial Sequence
<220> FEATURE:
<223> OTHER INFORMATION: oligonucleotide

<400> SEQUENCE: 18
cagtccgctc tcattgttta aggacccag                                     29

<210> SEQ ID NO 19
<211> LENGTH: 384
<212> TYPE: PRT
<213> ORGANISM: Mus musculus
<220> FEATURE:
<221> NAME/KEY: MISC_FEATURE
<222> LOCATION: (124)..(124)
<223> OTHER INFORMATION: unsure

<400> SEQUENCE: 19

Met His Leu Phe Ala Glu Thr Ile Asn Lys Phe Thr Leu Glu Leu Tyr
1               5                   10                  15

Arg Gln Leu Arg Glu Ser Asp Asn Asn Ile Phe Tyr Ser Pro Ile Ser
```

```
                    20                  25                  30
Met Met Thr Ala Leu Ala Met Leu Gln Leu Gly Ala Lys Gly Asn Thr
            35                  40                  45

Glu Lys Gln Ile Glu Lys Val Leu Gln Phe Asn Glu Thr Thr Lys Lys
    50                  55                  60

Thr Thr Glu Lys Ser Ala His Cys His Asp Glu Lys Asn Val His Glu
65                  70                  75                  80

Gln Phe Gln Lys Phe Met Thr Gln Leu Asn Lys Ser Asn Asp Ala Tyr
                85                  90                  95

Asp Leu Lys Thr Ala Asn Ser Ile Tyr Gly Ala Lys Ala Phe Pro Phe
            100                 105                 110

Leu Gln Thr Phe Leu Glu Asp Ile Lys Lys Tyr Xaa Glu Val Asn Val
        115                 120                 125

Glu Ser Leu Asp Phe Ala His Ala Ala Glu Glu Arg Gln Lys Lys Ile
    130                 135                 140

Asn Ser Trp Val Glu Ser Gln Thr Asn Gly Lys Ile Lys Asp Leu Phe
145                 150                 155                 160

Pro Ser Gly Ser Leu Asn Ser Ser Thr Ile Leu Val Leu Val Asn Ala
                165                 170                 175

Val Tyr Phe Lys Gly Gln Trp Asn His Thr Phe Asp Glu Lys His Thr
            180                 185                 190

Lys Glu Glu Lys Phe Trp Leu Asn Lys Asn Thr Ser Lys Pro Val Gln
        195                 200                 205

Met Met Lys Gln Arg Asn Lys Phe Asn Phe Met Phe Leu Glu Asp Val
    210                 215                 220

Gln Thr Lys Ile Val Glu Ile Pro Tyr Lys Gly Lys Glu Leu Ser Met
225                 230                 235                 240

Phe Val Leu Leu Pro Val Glu Ile Asp Gly Leu Lys Lys Leu Glu Glu
                245                 250                 255

Gln Leu Ser Thr Glu Lys Leu Leu Glu Trp Thr Arg Ala Glu Asn Met
            260                 265                 270

His Met Thr Glu Leu Tyr Leu Ser Leu Pro Arg Phe Lys Val Glu Glu
        275                 280                 285

Lys Tyr Asp Leu Ser Val Pro Leu Lys His Met Gly Met Val Gly Ala
    290                 295                 300

Phe Asp Pro Gln Lys Ala Asp Phe Ser Gly Met Asn Ser Thr Gln Gly
305                 310                 315                 320

Leu Val Val Ser Lys Val Leu His Lys Ser Phe Val Glu Val Asn Glu
                325                 330                 335

Glu Gly Thr Glu Ala Ala Ala Thr Thr Gly Ile Lys Ser His Asn Leu
            340                 345                 350

Ser Leu Gln Ile Thr Glu Asp Phe Tyr Cys Asp His Pro Leu Val Lys
        355                 360                 365

His Ser Lys Thr Asn Ser Ile Leu Phe Phe Gly Thr Ile Ser Ser Pro
    370                 375                 380

<210> SEQ ID NO 20
<211> LENGTH: 387
<212> TYPE: PRT
<213> ORGANISM: Mus musculus

<400> SEQUENCE: 20

Met Asp Leu Phe Ala Val Ala Thr Thr Lys Phe Thr Leu Glu Leu Tyr
1               5                   10                  15
```

```
Arg Gln Leu Arg Glu Ser Asp Asn Asn Ile Phe Tyr Ser Pro Ile Ser
             20                  25                  30

Met Met Arg Thr Leu Ala Met Leu Leu Gly Ala Lys Ala Asn Thr
         35                  40                  45

Glu Gln Gln Ile Lys Lys Val Leu His Phe Asn Glu Thr Thr Lys Lys
 50                  55                  60

Thr Thr Glu Lys Ser Ala Glu Ser His Asp Glu Asn Val His Gln
 65                  70                  75                  80

Gln Phe Gln Met Leu Met Thr Gln Leu Asn Lys Phe Asn Asn Ala Tyr
                 85                  90                  95

Asp Leu Lys Val Pro Asn Ser Ile Tyr Gly Ala Lys Asp Phe Pro Phe
                100                 105                 110

Leu Gln Thr Phe Leu Lys Asp Ile Arg Lys Tyr Tyr Gln Ala Asn Val
                115                 120                 125

Glu Ser Leu Asp Phe Ala His Ala Ala Glu Glu Ser Gln Lys Lys Ile
130                 135                 140

Asn Ser Trp Met Ala Arg Gln Thr Asn Gly Lys Ile Lys Asp Leu Phe
145                 150                 155                 160

Pro Ser Gly Ser Leu Asn Ser Ser Thr Ile Leu Val Leu Val Asn Ala
                165                 170                 175

Val Tyr Phe Lys Gly Gln Trp Asn His Lys Phe Asp Glu Lys His Thr
            180                 185                 190

Arg Glu Glu Lys Phe Trp Leu Asn Lys Asn Thr Ser Lys Pro Val Gln
        195                 200                 205

Met Met Lys Gln Arg Asn Lys Phe Asn Phe Ile Phe Leu Glu Asn Val
    210                 215                 220

Gln Ala Lys Ile Val Glu Ile Pro Tyr Lys Gly Lys Glu Leu Ser Met
225                 230                 235                 240

Phe Val Leu Leu Pro Val Glu Ile Asp Gly Leu Lys Lys Phe Glu Glu
                245                 250                 255

Gln Leu Thr Ala Asp Lys Leu Leu Gln Trp Thr Arg Ala Glu Asn Met
                260                 265                 270

His Leu Thr Glu Leu Tyr Leu Ser Leu Pro Gln Phe Lys Val Glu Glu
            275                 280                 285

Lys Tyr Asp Leu Arg Val Pro Leu Glu His Met Gly Met Val Asp Ala
        290                 295                 300

Phe Asp Pro Gln Lys Ala Asp Phe Ser Gly Met Ser Asn Ser Gln Gly
305                 310                 315                 320

Leu Val Val Ser Lys Val Leu His Lys Ser Phe Val Glu Val Asn Glu
                325                 330                 335

Glu Gly Ala Glu Ala Ala Thr Ala Met Ser Val Glu Ser Arg Ser Leu
            340                 345                 350

Ser Val Pro Lys Pro Asn Asp Phe Ser Cys Asn His Pro Phe Leu Phe
        355                 360                 365

Val Met Lys Gln Asn Lys Thr Asn Ser Ile Leu Phe Phe Gly Arg Val
    370                 375                 380

Ser Ser Pro
385

<210> SEQ ID NO 21
<211> LENGTH: 367
<212> TYPE: PRT
<213> ORGANISM: Mus musculus

<400> SEQUENCE: 21
```

Met Ala Ser Leu Ala Val Ser Ile Asn Gln Phe Ala Leu Glu Phe Ser
1               5                   10                  15

Lys Lys Leu Ala Glu Ser Ala Glu Gly Arg Asn Ile Phe Phe Ser Pro
            20                  25                  30

Trp Gly Ile Ser Thr Ala Leu Ala Met Val Tyr Leu Gly Thr Lys Gly
        35                  40                  45

Thr Thr Ala Asp Gln Met Ala Gln Val Leu Gln Phe Ser Ser Val Glu
50                  55                  60

Asp Phe Lys Ser Cys Pro Asp Ser Glu Lys Lys Arg Lys Met Glu Phe
65                  70                  75                  80

Asn Ser Gly Lys Phe Glu Ile Gln Ser Asp Phe Gln Thr Leu Ala
                85                  90                  95

Ala Glu Ile Leu Lys Pro Gly Asn Ser Tyr Val Leu Lys Thr Ala Asn
            100                 105                 110

Arg Ile Tyr Gly Glu Lys Thr Tyr Pro Phe His Asn Lys Tyr Leu Glu
            115                 120                 125

Asp Met Lys Thr Tyr Phe Gly Ala Glu Pro Gln Ser Val Asn Phe Val
130                 135                 140

Glu Ala Ser Gly Gln Ile Arg Lys Glu Ile Asn Ser Trp Val Gly Ser
145                 150                 155                 160

Gln Thr Gly Gly Lys Ile Pro Asn Leu Leu Pro Asp Asp Ser Val Asp
                165                 170                 175

Thr Lys Thr Lys Met Val Leu Val Asn Ala Leu Tyr Phe Lys Gly Thr
            180                 185                 190

Trp Glu His Gln Phe Ser Val Lys Ser Thr Thr Glu Arg Pro Phe Arg
        195                 200                 205

Val Asn Lys Thr Thr Ser Lys Pro Val Gln Met Met Ser Met Lys Gln
        210                 215                 220

Ser Leu Gln Val Phe His Ile Glu Glu Leu Gln Thr Ile Gly Leu Gln
225                 230                 235                 240

Leu His Tyr Gln Asn Arg Asp Leu Ser Leu Leu Leu Leu Pro Glu
                245                 250                 255

Ala Ile Asp Gly Leu Glu Gln Phe Lys Met Glu Glu Ser Tyr Asp Leu
            260                 265                 270

Lys Ser Ala Leu Lys Gly Met Gly Met Thr Asp Val Phe Ser Gln Ser
            275                 280                 285

Lys Ala Asp Phe Ser Asn Met Thr Ser Glu Arg Asn Leu Phe Leu Ser
            290                 295                 300

Asn Val Phe His Lys Thr Phe Leu Glu Ile Asn Glu Glu Gly Thr Glu
305                 310                 315                 320

Ala Ala Ala Gly Thr Gly Ser Glu Ile Ser Val Arg Ile Lys Ala Pro
                325                 330                 335

Ser Ile Glu Leu Asn Val Asp His Pro Phe Leu Phe Phe Ile Arg His
            340                 345                 350

Asn Lys Thr Lys Ser Ile Leu Phe Cys Gly Arg Phe Cys Ser Pro
            355                 360                 365

<210> SEQ ID NO 22
<211> LENGTH: 389
<212> TYPE: PRT
<213> ORGANISM: Mus musculus

<400> SEQUENCE: 22

Met Asp Ser Leu Gly Thr Ala Ala Thr Gln Phe Leu Phe Asp Leu Phe

```
1               5                   10                  15
Lys Glu Leu Asn Lys Thr Asn Asp Gly Asn Val Phe Phe Ser Pro Val
                20                  25                  30

Gly Ile Ser Thr Ala Ile Gly Met Ile Ile Leu Gly Thr Arg Gly Ala
                35                  40                  45

Thr Ala Ser Glu Leu Gln Lys Val Leu Tyr Thr Glu Gln Gly Thr Glu
            50                  55                  60

Ser Ser Arg Ile Lys Ser Glu Glu Glu Ile Glu Lys Arg Glu Glu
65                  70                  75                  80

Ile His His Gln Leu Gln Met Leu Leu Thr Glu Ile Ser Lys Phe Ser
                    85                  90                  95

Asn Asp Tyr Asp Leu Ile Ile Ser Asn Arg Leu Phe Gly Glu Lys Thr
                100                 105                 110

Tyr Leu Phe Leu Gln Lys Tyr Ile Asp Tyr Val Glu Lys Tyr Tyr His
                115                 120                 125

Ala Ser Leu Glu Pro Val Asp Phe Val Asn Ala Ala Asp Glu Ser Arg
                130                 135                 140

Lys Lys Ile Asn Ser Trp Val Glu Ser Gln Thr Asn Gly Lys Val Lys
145                 150                 155                 160

Asp Leu Phe Pro Glu Gly Ser Leu Asn Ser Ser Thr Lys Leu Val Leu
                165                 170                 175

Ile Asn Thr Val Tyr Phe Lys Gly Leu Trp Asp Arg Glu Phe Lys Lys
                180                 185                 190

Glu His Thr Lys Glu Glu Asp Phe Trp Leu Asn Lys Asn Leu Ser Lys
                195                 200                 205

Pro Val Gln Met Met Ala Leu Cys Ser Ser Phe Asn Phe Thr Phe Leu
                210                 215                 220

Glu Asp Leu Gln Ala Lys Ile Val Gly Ile Pro Tyr Lys Asn Asn Asp
225                 230                 235                 240

Ile Ser Met Phe Val Leu Leu Pro Asn Asp Ile Asp Gly Leu Glu Lys
                245                 250                 255

Ile Met Asp Lys Met Ser Pro Glu Lys Leu Val Glu Trp Thr Ser Pro
                260                 265                 270

Gly His Leu Glu Gln Arg Arg Val Asp Leu Arg Leu Pro Arg Leu Gln
                275                 280                 285

Val Glu Glu Thr Tyr Asp Leu Glu Pro Val Leu Glu Ala Val Gly Ile
                290                 295                 300

His Ser Ala Phe Ser Glu His Ala Asp Tyr Ser Gly Met Ser Ala Arg
305                 310                 315                 320

Ser Gly Leu His Ala Gln Asn Phe Leu His Arg Ser Phe Leu Val Val
                325                 330                 335

Thr Glu Glu Gly Val Glu Ala Thr Ala Gly Thr Gly Val Gly Leu Lys
                340                 345                 350

Val Ser Ser Ala Ala Ser Cys Glu Leu Val His Cys Asn His Pro Phe
                355                 360                 365

Leu Phe Phe Ile Arg His Arg Glu Ser Asp Ser Ile Leu Phe Phe Gly
                370                 375                 380

Lys Phe Ser Ser Pro
385

<210> SEQ ID NO 23
<211> LENGTH: 417
<212> TYPE: PRT
<213> ORGANISM: Homo sapiens
```

<400> SEQUENCE: 23

```
Met Ala Ser Tyr Leu Tyr Gly Val Leu Phe Ala Val Gly Leu Cys Ala
1               5                   10                  15

Pro Ile Tyr Cys Val Ser Pro Ala Asn Ala Pro Ser Ala Tyr Pro Arg
            20                  25                  30

Pro Ser Ser Thr Lys Ser Thr Pro Ala Ser Gln Val Tyr Ser Leu Asn
        35                  40                  45

Thr Asp Phe Ala Phe Arg Leu Tyr Arg Arg Leu Val Leu Glu Thr Pro
    50                  55                  60

Ser Gln Asn Ile Phe Phe Ser Pro Val Ser Val Ser Thr Ser Leu Ala
65                  70                  75                  80

Met Leu Ser Leu Gly Ala His Ser Val Thr Lys Thr Gln Ile Leu Gln
                85                  90                  95

Gly Leu Gly Phe Asn Leu Thr His Thr Pro Glu Ser Ala Ile His Gln
            100                 105                 110

Gly Phe Gln His Leu Val His Ser Leu Thr Val Pro Ser Lys Asp Leu
        115                 120                 125

Thr Leu Lys Met Gly Ser Ala Leu Phe Val Lys Glu Leu Gln Leu
    130                 135                 140

Gln Ala Asn Phe Leu Gly Asn Val Lys Arg Leu Tyr Glu Ala Glu Val
145                 150                 155                 160

Phe Ser Thr Asp Phe Ser Asn Pro Ser Ile Ala Gln Ala Arg Ile Asn
            165                 170                 175

Ser His Val Lys Lys Thr Gln Gly Lys Val Val Asp Ile Ile Gln
        180                 185                 190

Gly Leu Asp Leu Leu Thr Ala Met Val Leu Val Asn His Ile Phe Phe
    195                 200                 205

Lys Ala Lys Trp Glu Lys Pro Phe His Leu Glu Tyr Thr Arg Lys Asn
210                 215                 220

Phe Pro Phe Leu Val Gly Glu Gln Val Thr Val Gln Val Pro Met Met
225                 230                 235                 240

His Gln Lys Glu Gln Phe Ala Phe Gly Val Asp Thr Glu Leu Asn Cys
            245                 250                 255

Phe Val Leu Gln Met Asp Tyr Lys Gly Asp Ala Val Ala Phe Phe Val
        260                 265                 270

Leu Pro Ser Lys Gly Lys Met Arg Gln Leu Glu Gln Ala Leu Ser Ala
    275                 280                 285

Arg Thr Leu Ile Lys Trp Ser His Ser Leu Gln Lys Arg Trp Ile Glu
290                 295                 300

Val Phe Ile Pro Arg Phe Ser Ile Ser Ala Ser Tyr Asn Leu Glu Thr
305                 310                 315                 320

Ile Leu Pro Lys Met Gly Ile Gln Asn Ala Phe Asp Lys Asn Ala Asp
            325                 330                 335

Phe Ser Gly Ile Ala Lys Arg Asp Ser Leu Gln Val Ser Lys Ala Thr
        340                 345                 350

His Lys Ala Val Leu Asp Val Ser Glu Glu Gly Thr Glu Ala Thr Ala
    355                 360                 365

Ala Thr Thr Thr Lys Phe Ile Val Arg Ser Lys Asp Gly Pro Ser Tyr
370                 375                 380

Phe Thr Val Ser Phe Asn Arg Thr Phe Leu Met Met Ile Thr Asn Lys
385                 390                 395                 400

Ala Thr Asp Gly Ile Leu Phe Leu Gly Lys Val Glu Asn Pro Thr Lys
```

405                 410                 415
Ser

<210> SEQ ID NO 24
<211> LENGTH: 403
<212> TYPE: PRT
<213> ORGANISM: Homo sapiens

<400> SEQUENCE: 24

Met Ala Ser Tyr Leu Tyr Gly Val Leu Phe Ala Val Gly Leu Cys Ala
1               5                   10                  15

Pro Ile Tyr Cys Val Ser Pro Ala Asn Ala Pro Ser Ala Tyr Pro Arg
            20                  25                  30

Pro Ser Ser Thr Lys Ser Thr Pro Ala Ser Gln Val Tyr Ser Leu Asn
        35                  40                  45

Thr Asp Phe Ala Phe Arg Leu Tyr Arg Arg Leu Val Leu Glu Thr Pro
    50                  55                  60

Ser Gln Asn Ile Phe Phe Ser Pro Val Ser Val Ser Thr Ser Leu Ala
65                  70                  75                  80

Met Leu Ser Leu Gly Ala His Ser Val Thr Lys Thr Glu Ile Leu Gln
                85                  90                  95

Gly Leu Gly Phe Asn Leu Thr His Thr Pro Glu Ser Ala Ile His Gln
            100                 105                 110

Gly Phe Gln His Leu Val His Ser Leu Thr Val Pro Ser Lys Asp Leu
        115                 120                 125

Thr Leu Lys Met Gly Ser Ala Leu Phe Val Lys Lys Glu Leu Gln Leu
    130                 135                 140

Gln Ala Asn Phe Leu Gly Asn Val Lys Arg Leu Tyr Glu Ala Glu Val
145                 150                 155                 160

Phe Ser Thr Asp Phe Ser Asn Pro Ser Ile Ala Gln Ala Arg Ile Asn
                165                 170                 175

Ser His Val Lys Lys Thr Gln Gly Lys Val Val Asp Ile Ile Gln
            180                 185                 190

Gly Leu Asp Leu Leu Thr Ala Met Val Leu Val Asn His Ile Phe Phe
        195                 200                 205

Lys Ala Lys Trp Glu Lys Pro Phe His Pro Glu Tyr Thr Arg Lys Asn
    210                 215                 220

Phe Pro Phe Leu Val Gly Glu Gln Val Thr Val His Val Pro Met Met
225                 230                 235                 240

His Gln Lys Glu Gln Phe Ala Phe Gly Val Asp Thr Glu Leu Asn Cys
                245                 250                 255

Phe Val Leu Gln Met Asp Tyr Lys Gly Asp Ala Val Ala Phe Phe Val
            260                 265                 270

Leu Pro Ser Lys Gly Lys Met Arg Gln Leu Glu Gln Ala Leu Ser Ala
        275                 280                 285

Arg Thr Leu Arg Lys Trp Ser His Ser Leu Gln Lys Arg Trp Ile Glu
    290                 295                 300

Val Phe Ile Pro Arg Phe Ser Ile Ser Ala Ser Tyr Asn Leu Glu Thr
305                 310                 315                 320

Ile Leu Pro Lys Met Gly Ile Gln Asn Ala Phe Asp Lys Asn Ala Asp
                325                 330                 335

Phe Ser Gly Ile Ala Lys Arg Asp Ser Leu Gln Val Ser Lys Ala Thr
            340                 345                 350

His Lys Ala Val Leu Asp Val Ser Glu Glu Gly Thr Glu Ala Thr Ala

```
                 355                 360                 365
Ala Thr Thr Lys Phe Ile Val Arg Ser Lys Asp Gly Pro Ser Tyr
        370                 375                 380

Phe Thr Val Ser Phe Asn Arg Thr Phe Leu Met Met Ile Thr Asn Lys
385                 390                 395                 400

Ala Thr Asp

<210> SEQ ID NO 25
<211> LENGTH: 46
<212> TYPE: PRT
<213> ORGANISM: Homo sapiens

<400> SEQUENCE: 25

Trp Ile Glu Val Phe Ile Pro Arg Phe Ser Ile Ser Ala Ser Tyr Asn
1               5                   10                  15

Leu Glu Thr Ile Leu Pro Lys Met Gly Ile Gln Asn Ala Phe Asp Lys
            20                  25                  30

Asn Ala Asp Phe Ser Gly Ile Ala Lys Arg Asp Ser Leu Gln
        35                  40                  45

<210> SEQ ID NO 26
<211> LENGTH: 179
<212> TYPE: PRT
<213> ORGANISM: Homo sapiens

<400> SEQUENCE: 26

Met Ala Phe Ile Ala Ala Leu Gly Leu Leu Met Ala Gly Ile Cys Pro
1               5                   10                  15

Ala Val Leu Cys Asp Gly Thr Leu Gly Arg Asp Thr Leu Ser His Glu
            20                  25                  30

Asp His Gly Lys Gly Arg Gln Leu His Ser Leu Thr Leu Ala Ser Ser
        35                  40                  45

Asn Thr Asp Phe Ala Leu Ser Leu Tyr Lys Lys Leu Ala Leu Arg Asn
    50                  55                  60

Pro Asp Lys Asn Val Val Phe Ser Pro Leu Ser Ile Ser Ala Ala Leu
65                  70                  75                  80

Thr Ile Leu Ser Leu Gly Ala Lys Asp Ser Thr Met Glu Glu Ile Leu
                85                  90                  95

Glu Gly Leu Lys Phe Asn Leu Thr Glu Ile Thr Glu Glu Glu Ile His
            100                 105                 110

Gln Gly Phe Gly His Leu Leu Gln Arg Leu Ser Gln Pro Glu Asp Gln
        115                 120                 125

Val Glu Ile Asn Thr Gly Ser Ala Leu Phe Ile Asp Lys Glu Gln Pro
    130                 135                 140

Ile Leu Ser Glu Phe Gln Glu Lys Thr Arg Ala Leu Tyr Gln Ala Glu
145                 150                 155                 160

Ala Phe Ile Ala Asp Phe Lys Gln Pro Asn Glu Ala Lys Lys Leu Ile
                165                 170                 175

Asn Asp Tyr

<210> SEQ ID NO 27
<211> LENGTH: 551
<212> TYPE: PRT
<213> ORGANISM: Homo sapiens

<400> SEQUENCE: 27

Met Glu Gly His Gly Leu Pro Cys Pro Ser Leu Gly Leu Leu Phe Trp
```

-continued

```
1               5                   10                  15
Cys Trp Gly Arg Glu Cys Gln Arg His Glu Glu Gly Ser Ile Arg
                20                  25                  30

Tyr Leu Val Pro Ser Lys Ser Pro Thr Ser Lys Val Ile Ser Gly Ile
                35                  40                  45

Pro Gln Cys Asp Lys Gly Leu Asp Glu Gly Phe Leu Ala Gly Pro Pro
    50                  55                  60

Gly Ser Arg Asn Leu Asp Arg Val Val Glu Thr Ser Pro Ala Glu Thr
65                  70                  75                  80

Ala Ile Ala Ser Phe Leu Ser Val Leu Ser Cys Asp Ser Lys Gln Ile
                85                  90                  95

Leu Leu His Phe Phe Lys Arg Gly Ala His Glu Cys Trp Arg Pro Thr
                100                 105                 110

Arg Thr Glu Ser Ser Lys Glu Thr Cys Asn Ser Asp Thr Lys Val Cys
                115                 120                 125

Glu Tyr Val Ala His Ser Arg Glu Glu Gly Leu Glu Lys Arg Glu Asp
                130                 135                 140

Val Phe Tyr Leu Gly Pro Leu Pro Lys Ile Gly Thr Ile Val Leu Ser
145                 150                 155                 160

Gly Leu Ala Cys Lys Leu Leu Gln Glu Gly Thr Leu Pro Ala Ser Met
                165                 170                 175

Pro Pro Phe Leu Ile Thr Leu Phe Leu Phe His Ser Cys Cys Leu Arg
                180                 185                 190

Ala Asn Gly His Leu Arg Glu Gly Met Thr Leu Leu Lys Thr Glu Phe
                195                 200                 205

Ala Leu His Leu Tyr Gln Ser Val Ala Ala Cys Arg Asn Glu Thr Asn
                210                 215                 220

Phe Val Ile Ser Pro Ala Gly Val Ser Leu Pro Leu Glu Ile Leu Gln
225                 230                 235                 240

Phe Gly Ala Glu Gly Ser Thr Gly Gln Gln Leu Ala Asp Ala Leu Gly
                245                 250                 255

Tyr Thr Val His Asp Lys Arg Val Lys Asp Phe Leu His Ala Val Tyr
                260                 265                 270

Ala Thr Leu Pro Thr Ser Ser Gln Gly Thr Glu Met Glu Leu Ala Cys
                275                 280                 285

Ser Leu Phe Val Gln Val Gly Thr Pro Leu Ser Pro Cys Phe Val Glu
                290                 295                 300

His Val Ser Trp Trp Ala Asn Ser Ser Leu Glu Pro Ala Asp Leu Ser
305                 310                 315                 320

Glu Pro Asn Ser Thr Ala Ile Gln Thr Ser Glu Gly Ala Ser Arg Glu
                325                 330                 335

Thr Ala Gly Gly Gly Pro Ser Glu Gly Pro Gly Gly Trp Pro Trp Glu
                340                 345                 350

Gln Val Ser Ala Ala Phe Ala Gln Leu Val Leu Val Ser Thr Met Ser
                355                 360                 365

Phe Gln Gly Thr Trp Arg Lys Arg Phe Ser Ser Thr Asp Thr Gln Ile
                370                 375                 380

Leu Pro Phe Thr Cys Ala Tyr Gly Leu Val Leu Gln Val Pro Met Met
385                 390                 395                 400

His Gln Thr Thr Glu Val Asn Tyr Gly Gln Phe Gln Asp Thr Ala Gly
                405                 410                 415

His Gln Val Gly Val Leu Glu Leu Pro Tyr Leu Gly Ser Ala Val Ser
                420                 425                 430
```

```
Leu Phe Leu Val Leu Pro Arg Asp Lys Asp Thr Pro Leu Ser His Ile
            435                 440                 445

Glu Pro His Leu Thr Ala Ser Thr Ile His Leu Trp Thr Thr Ser Leu
    450                 455                 460

Arg Arg Ala Arg Met Asp Val Phe Leu Pro Arg Phe Arg Ile Gln Asn
465                 470                 475                 480

Gln Phe Asn Leu Lys Ser Ile Leu Asn Ser Trp Gly Val Thr Asp Leu
                485                 490                 495

Phe Asp Pro Leu Lys Ala Asn Leu Lys Gly Ile Ser Gly Gln Asp Gly
            500                 505                 510

Phe Tyr Val Ser Glu Ala Ile His Lys Ala Lys Ile Glu Val Leu Glu
            515                 520                 525

Glu Gly Thr Lys Ala Ser Gly Ala Thr Gly Phe Ile Gln Lys Asn Val
            530                 535                 540

Leu Lys Val Met Ser Asn Leu
545                 550

<210> SEQ ID NO 28
<211> LENGTH: 376
<212> TYPE: PRT
<213> ORGANISM: Homo sapiens

<400> SEQUENCE: 28

Pro Pro Phe Leu Ile Thr Leu Phe Leu Phe His Ser Cys Cys Leu Arg
1               5                   10                  15

Ala Asn Gly His Leu Arg Glu Gly Met Thr Leu Leu Lys Thr Glu Phe
                20                  25                  30

Ala Leu His Leu Tyr Gln Ser Val Ala Ala Cys Arg Asn Glu Thr Asn
            35                  40                  45

Phe Val Ile Ser Pro Ala Gly Val Ser Leu Pro Leu Glu Ile Leu Gln
        50                  55                  60

Phe Gly Ala Glu Gly Ser Thr Gly Gln Gln Leu Ala Asp Ala Leu Gly
65                  70                  75                  80

Tyr Thr Val His Ala Lys Ala Pro Ser Met Glu Leu Ala Cys Ser Leu
                85                  90                  95

Phe Val Gln Val Gly Thr Pro Leu Ser Pro Cys Phe Val Glu His Val
                100                 105                 110

Ser Trp Trp Ala Asn Ser Ser Leu Glu Pro Ala Asp Leu Ser Glu Pro
            115                 120                 125

Asn Ser Thr Ala Ile Gln Thr Ser Glu Gly Ala Ser Arg Glu Thr Ala
130                 135                 140

Gly Gly Gly Pro Ser Glu Gly Pro Gly Gly Trp Pro Trp Glu Gln Val
145                 150                 155                 160

Ser Ala Ala Phe Ala Gln Leu Val Leu Val Ser Thr Met Ser Phe Gln
                165                 170                 175

Gly Thr Trp Arg Lys Arg Phe Ser Ser Thr Asp Thr Gln Ile Leu Pro
                180                 185                 190

Phe Thr Cys Ala Tyr Gly Leu Val Leu Gln Val Pro Met Met His Gln
            195                 200                 205

Thr Thr Glu Val Asn Tyr Gly Gln Phe Gln Asp Thr Ala Gly His Gln
        210                 215                 220

Val Gly Val Leu Glu Leu Pro Tyr Leu Gly Ser Ala Val Ser Leu Phe
225                 230                 235                 240

Leu Val Leu Pro Arg Asp Lys Asp Thr Pro Leu Ser His Ile Glu Pro
```

-continued

```
                245                 250                 255
His Leu Thr Ala Ser Thr Ile His Leu Trp Thr Thr Ser Leu Arg Arg
            260                 265                 270

Ala Arg Met Asp Val Phe Leu Pro Arg Phe Arg Ile Gln Asn Gln Phe
            275                 280                 285

Asn Leu Lys Ser Ile Leu Asn Ser Trp Gly Val Thr Asp Leu Phe Asp
            290                 295                 300

Pro Leu Lys Ala Asn Leu Lys Gly Ile Ser Gly Gln Asp Gly Phe Tyr
305                 310                 315                 320

Val Ser Glu Ala Ile His Lys Ala Lys Ile Glu Val Leu Glu Glu Gly
            325                 330                 335

Thr Lys Ala Ser Gly Ala Thr Ala Leu Leu Leu Lys Arg Ser Arg
            340                 345                 350

Ile Pro Ile Phe Lys Ala Asp Arg Pro Phe Ile Tyr Phe Leu Arg Glu
            355                 360                 365

Pro Asn Thr Ala Phe Leu Ser Phe
            370                 375

<210> SEQ ID NO 29
<211> LENGTH: 255
<212> TYPE: PRT
<213> ORGANISM: Homo sapiens

<400> SEQUENCE: 29

Trp Lys Arg Met Ala Gln Ile Leu Trp Thr Pro Gln Met Ser Gly Phe
1               5                   10                  15

Arg Glu Lys Leu Leu Arg Ala Cys Trp Gln Arg His Phe Ser Gln Lys
                20                  25                  30

Ser Pro Cys Gly Ala Gly Val Arg Gly Val Pro Gly Pro Ser Thr Met
            35                  40                  45

Ser Ala Leu Ser Glu Ala Asn Gly Ser Ser His His Leu Leu Lys Glu
        50                  55                  60

Pro Tyr Glu Glu Asn Pro Ser Cys Asn Val Leu Leu Ser Val Pro Ser
65                  70                  75                  80

Val Ser Ser Ala Leu Ala Met Leu Phe Leu Gly Val Glu Gly Asn Val
                85                  90                  95

Ala Ala Gln Met Ala Gln Ala Arg Arg Pro Pro Leu His Lys Glu Glu
            100                 105                 110

Glu Leu Phe Val Ala Ile Arg Val Val Cys Gln Lys Phe Leu Asp Phe
            115                 120                 125

Leu Pro Ser Ser Thr Cys Arg Gly Gly Val Thr Ser Ile Lys Ser Tyr
        130                 135                 140

Pro Pro Ile Val Ile Asn Arg Lys Leu Asp Asn Val Tyr Glu Thr Thr
145                 150                 155                 160

Gly Asp Thr Phe His Ile Gly Tyr Asp Trp Ser Ile Ile Leu Glu Gly
                165                 170                 175

Arg Pro Thr Asn Ala Gly Arg Pro Ser Thr Arg Ala Ser Ala His
            180                 185                 190

Val Gln Leu Leu Asn Cys Pro Ala Ser Glu Leu Leu Trp Lys Met Ser
        195                 200                 205

Leu Tyr Met Lys Lys Ser Ala Ser Gly Gln Ser Gln Ala Gln Trp Ile
    210                 215                 220

Ala Lys Met Trp Lys Ser Pro Arg Phe Lys Leu Gln Glu Asn Arg Ser
225                 230                 235                 240
```

```
Met Glu Ser Ala Leu Ser Cys Trp Gly Ile Thr Asp Ala Phe Asp
            245                 250                 255
```

<210> SEQ ID NO 30
<211> LENGTH: 86
<212> TYPE: PRT
<213> ORGANISM: Homo sapiens

<400> SEQUENCE: 30

```
Met Ser Ala Leu Ser Glu Ala Asn Gly Ser His His Leu Leu Lys
1               5                   10                  15

Glu Pro Tyr Glu Glu Asn Pro Ser Cys Asn Val Leu Leu Ser Val Pro
            20                  25                  30

Ser Val Ser Ser Ala Leu Ala Met Leu Phe Leu Gly Val Glu Gly Asn
            35                  40                  45

Val Ala Ala Gln Met Ala Gln Ala Arg Arg Pro Pro Leu His Lys Glu
        50                  55                  60

Glu Glu Leu Phe Val Ala Ile Arg Val Val Cys Gln Lys Phe Leu Asp
65                  70                  75                  80

Phe Leu Pro Ser Ser Thr
                85
```

<210> SEQ ID NO 31
<211> LENGTH: 51
<212> TYPE: PRT
<213> ORGANISM: Homo sapiens

<400> SEQUENCE: 31

```
Trp Lys Met Ser Leu Tyr Met Lys Lys Ser Ala Ser Gly Gln Ser Gln
1               5                   10                  15

Ala Gln Trp Ile Ala Lys Met Trp Lys Ser Pro Arg Phe Lys Leu Glu
            20                  25                  30

Glu Asn Arg Ser Met Glu Ser Ala Leu Ser Cys Trp Gly Ile Thr Asp
            35                  40                  45

Ala Phe Asp
    50
```

<210> SEQ ID NO 32
<211> LENGTH: 356
<212> TYPE: PRT
<213> ORGANISM: Homo sapiens

<400> SEQUENCE: 32

```
Ala Phe Cys Leu Leu Ala Val Ala Leu Ala Thr Glu Val Lys Lys Pro
1               5                   10                  15

Ala Ala Thr Ala Ala Pro Gly Thr Ala Glu Lys Leu Ser Pro Lys Ala
            20                  25                  30

Ala Thr Leu Ala Glu His Ser Ala Gly Leu Ala Phe Ser Leu Tyr Gln
            35                  40                  45

Ala Met Ala Lys Asp Gln Ala Val Glu Asn Ile Leu Val Ser Pro Val
        50                  55                  60

Val Val Ala Ser Ser Leu Gly Leu Val Ser Leu Gly Gly Lys Ala Thr
65                  70                  75                  80

Thr Ala Ser Glu Ala Lys Ala Val Leu Ser Ala Lys Gln Leu Ser Asp
                85                  90                  95

Glu Glu Val His Ala Gly Val Gly Glu Pro Leu Arg Ser Leu Ser Asn
            100                 105                 110

Ser Thr Ala Arg Asn Val Thr Trp Lys Leu Cys Ser Arg Leu Ser Lys
```

```
                115                 120                 125
Gln His Tyr Asn Cys Glu His Ser Lys Ile Asn Phe His Asp Lys Arg
            130                 135                 140

Ser Ala Leu Gln Ser Ile His Glu Trp Ala Val Gln Thr Thr Asp Gly
145                 150                 155                 160

Lys Leu Pro Lys Val Thr Lys Asp Met Glu Cys Met Asp Gly Ala Leu
                165                 170                 175

Leu Val Asn Thr Met Phe Phe Lys Pro His Trp Asn Glu Lys Phe His
                180                 185                 190

His Lys Met Val Glu Asn Arg Gly Phe Met Val Thr Arg Phe Tyr Thr
                195                 200                 205

Val Gly Val Met Val Met His Gln Thr Gly Leu Tyr Asn Tyr Tyr Asp
            210                 215                 220

Asn Glu Lys Glu Lys Leu Gln Ile Val Glu Met Pro Leu Ala His Lys
225                 230                 235                 240

Leu Ser Ser Leu Ile Ile Leu Met Pro His His Val Glu Pro Leu Glu
                245                 250                 255

Ala Leu Lys Ser Trp Leu Gly Leu Thr Glu Ala Ile Asp Lys Asn Lys
                260                 265                 270

Ala Asn Leu Ser Arg Met Pro His Lys Lys Asp Leu Tyr Leu Thr Ser
            275                 280                 285

Val Phe His Ala Thr Ala Phe Glu Leu Asp Thr Asp Gly Asn Ser Phe
        290                 295                 300

Asp Gln Asp Ile Tyr Gly Ser Lys Glu Leu Arg Ser Pro Lys Leu Phe
305                 310                 315                 320

Tyr Ser Asp His Pro Phe Ile Phe Leu Val Trp Asp Thr Gln Ser Gly
                325                 330                 335

Ser Leu Leu Phe Thr Gly His Leu Val Arg Pro Lys Val Asp Lys Met
            340                 345                 350

Gln Asp Glu Phe
        355

<210> SEQ ID NO 33
<211> LENGTH: 409
<212> TYPE: PRT
<213> ORGANISM: Homo sapiens
<220> FEATURE:
<221> NAME/KEY: MISC_FEATURE
<222> LOCATION: (293)..(293)
<223> OTHER INFORMATION: unsure

<400> SEQUENCE: 33

Ala Phe Cys Leu Leu Glu Ala Ala Leu Ala Ala Glu Val Lys Lys Pro
1               5                   10                  15

Ala Ala Ala Ala Ala Pro Gly Thr Ala Glu Lys Leu Ser Pro Lys Ala
                20                  25                  30

Ala Thr Leu Ala Glu Arg Ser Ala Gly Leu Ala Phe Ser Leu Tyr Gln
            35                  40                  45

Ala Met Ala Lys Asp Gln Ala Val Glu Asn Ile Leu Val Ser Pro Val
        50                  55                  60

Val Val Ala Ser Ser Leu Gly Leu Val Ser Leu Gly Gly Lys Ala Thr
65                  70                  75                  80

Thr Ala Ser Gln Ala Lys Ala Val Leu Ser Ala Glu Gln Leu Arg Asp
                85                  90                  95

Glu Glu Val His Ala Gly Leu Gly Glu Leu Leu Arg Ser Leu Ser Asn
                100                 105                 110
```

-continued

```
Ser Thr Ala Arg Asn Val Thr Trp Lys Leu Gly Ser Arg Leu Tyr Gly
        115                 120                 125

Pro Ser Ser Val Ser Phe Ala Asp Asp Phe Val Arg Ser Ser Lys Gln
    130                 135                 140

His Tyr Asn Cys Glu His Ser Lys Ile Asn Phe Arg Asp Lys Arg Ser
145                 150                 155                 160

Ala Leu Gln Ser Ile Asn Glu Trp Ala Ala Gln Thr Thr Asp Gly Lys
                165                 170                 175

Leu Pro Glu Val Thr Lys Asp Val Glu Arg Thr Asp Gly Ala Leu Leu
            180                 185                 190

Val Asn Ala Met Phe Phe Lys Pro His Trp Asp Glu Lys Phe His His
        195                 200                 205

Lys Met Val Asp Asn Arg Gly Phe Met Val Thr Arg Ser Tyr Thr Val
    210                 215                 220

Gly Val Met Met Met His Arg Thr Gly Leu Tyr Asn Tyr Tyr Asp Asp
225                 230                 235                 240

Glu Lys Glu Lys Leu Gln Ile Val Glu Met Pro Leu Ala His Lys Leu
                245                 250                 255

Ser Ser Leu Ile Ile Leu Met Pro His His Val Glu Pro Leu Glu Arg
            260                 265                 270

Leu Glu Lys Leu Leu Thr Lys Glu Gln Leu Lys Ile Trp Met Gly Lys
        275                 280                 285

Met Gln Lys Lys Xaa Val Ala Ile Ser Leu Pro Lys Gly Val Val Glu
    290                 295                 300

Val Thr His Asp Leu Gln Lys His Leu Ala Gly Leu Gly Leu Thr Glu
305                 310                 315                 320

Ala Ile Asp Lys Asn Lys Ala Asp Leu Ser Arg Met Ser Gly Lys Lys
                325                 330                 335

Asp Leu Tyr Leu Ala Ser Val Phe His Ala Thr Ala Phe Glu Leu Asp
            340                 345                 350

Thr Asp Gly Asn Pro Phe Asp Gln Asp Ile Tyr Gly Arg Glu Glu Leu
        355                 360                 365

Arg Ser Pro Lys Leu Phe Tyr Ala Asp His Pro Phe Ile Phe Leu Val
    370                 375                 380

Arg Asp Thr Gln Ser Gly Ser Leu Leu Phe Ile Gly Arg Leu Val Arg
385                 390                 395                 400

Pro Lys Gly Asp Lys Met Arg Asp Glu
                405

<210> SEQ ID NO 34
<211> LENGTH: 351
<212> TYPE: PRT
<213> ORGANISM: Homo sapiens

<400> SEQUENCE: 34

Ala Phe Cys Leu Leu Ala Val Ala Leu Ala Thr Glu Val Lys Lys Pro
1               5                   10                  15

Ala Ala Thr Ala Ala Pro Gly Thr Ala Glu Lys Leu Ser Pro Lys Ala
                20                  25                  30

Ala Thr Leu Ala Glu His Ser Ala Gly Leu Ala Phe Ser Leu Tyr Gln
            35                  40                  45

Ala Met Ala Lys Asp Gln Ala Val Glu Asn Ile Leu Val Ser Pro Val
        50                  55                  60

Val Val Ala Ser Ser Leu Gly Leu Val Ser Leu Gly Gly Lys Ala Thr
```

```
            65                  70                  75                  80
Thr Ala Ser Glu Ala Lys Ala Val Leu Ser Ala Lys Gln Leu Ser Asp
                85                  90                  95
Gln Glu Val His Ala Gly Val Gly Glu Pro Leu Arg Ser Leu Ser Asn
            100                 105                 110
Tyr Thr Ala Arg Asn Gly Thr Trp Lys Leu Cys Ser Arg Leu Ser Lys
        115                 120                 125
Gln His Tyr Asn Cys Glu His Ser Lys Ile Asn Phe His Asp Lys Arg
    130                 135                 140
Ser Ala Leu Gln Ser Ile His Glu Trp Ala Val Gln Thr Thr Asp Gly
145                 150                 155                 160
Lys Leu Pro Lys Val Thr Lys Asp Met Glu Cys Met Asp Gly Ala Leu
                165                 170                 175
Leu Val Asn Thr Met Phe Phe Lys Pro His Trp Asn Glu Lys Phe His
            180                 185                 190
His Lys Met Val Glu Asn Arg Gly Phe Met Val Thr Arg Phe Tyr Thr
        195                 200                 205
Val Gly Val Met Val Met His Gln Thr Gly Leu Tyr Asn Tyr Tyr Asp
    210                 215                 220
Asn Glu Lys Glu Lys Leu Gln Ile Val Glu Met Pro Leu Ala His Lys
225                 230                 235                 240
Leu Ser Ser Leu Ile Ile Leu Met Pro His His Lys Leu Leu Ala Arg
                245                 250                 255
Leu Gly Leu Thr Glu Ala Ile Asp Lys Asn Lys Ala Asn Leu Ser Arg
            260                 265                 270
Met Pro His Lys Lys Asp Leu Tyr Leu Thr Ser Val Phe His Ala Thr
        275                 280                 285
Ala Phe Glu Leu Asp Thr Asp Gly Asn Ser Phe Asp Gln Asp Ile Tyr
    290                 295                 300
Gly Ser Lys Glu Leu Arg Ser Pro Lys Leu Phe Tyr Ser Asp His Pro
305                 310                 315                 320
Phe Ile Phe Leu Val Trp Asp Thr Gln Ser Gly Ser Leu Leu Phe Thr
                325                 330                 335
Gly His Leu Val Arg Pro Lys Val Asp Lys Met Gln Asp Glu Phe
            340                 345                 350

<210> SEQ ID NO 35
<211> LENGTH: 302
<212> TYPE: PRT
<213> ORGANISM: Homo sapiens

<400> SEQUENCE: 35

Met Ala Lys Asp Gln Ala Val Glu Asn Ile Leu Val Ser Pro Val Val
1               5                   10                  15
Val Ala Ser Ser Leu Gly Leu Val Ser Leu Gly Ser Lys Ala Thr Thr
                20                  25                  30
Ala Ser Glu Ala Lys Ala Val Leu Ser Ala Lys Gln Leu Arg Asp Glu
            35                  40                  45
Glu Val His Ala Gly Val Gly Glu Pro Leu Arg Ser Leu Ser Asn Ser
        50                  55                  60
Thr Ala Arg Asn Val Thr Trp Lys Leu Cys Ser Arg Leu Ser Lys Gln
65                  70                  75                  80
His Tyr Asn Cys Glu His Ser Lys Ile Asn Phe His Asp Lys Arg Ser
                85                  90                  95
```

-continued

```
Ala Leu Gln Ser Ile His Glu Trp Ala Val Gln Thr Thr Asp Gly Lys
            100                 105                 110

Leu Pro Lys Val Thr Lys Asp Met Glu Cys Met Asp Gly Ala Leu Leu
        115                 120                 125

Val Asn Thr Met Phe Phe Lys Pro His Trp Asn Glu Lys Phe His His
    130                 135                 140

Lys Met Val Glu Asn Arg Gly Phe Met Val Thr Arg Phe Tyr Thr Val
145                 150                 155                 160

Gly Val Met Val Met His Gln Thr Gly Leu Tyr Asn Tyr Tyr Asp Asn
                165                 170                 175

Glu Lys Glu Lys Leu Gln Ile Val Glu Met Pro Leu Ala His Lys Leu
            180                 185                 190

Ser Ser Leu Ile Ile Leu Met Pro His His Lys Leu Leu Ala Arg Leu
            195                 200                 205

Gly Leu Thr Glu Ala Ile Asp Lys Asn Lys Ala Asn Leu Ser Arg Met
    210                 215                 220

Pro His Lys Lys Asp Leu Tyr Leu Thr Ser Val Phe His Ala Thr Ala
225                 230                 235                 240

Phe Glu Leu Asp Thr Asp Gly Asn Ser Phe Asp Gln Asp Ile Tyr Gly
                245                 250                 255

Ser Lys Glu Leu Arg Ser Pro Lys Leu Phe Tyr Ser Asp His Pro Phe
            260                 265                 270

Ile Phe Leu Val Trp Asp Thr Gln Ser Gly Ser Leu Leu Phe Thr Gly
            275                 280                 285

His Leu Val Arg Pro Lys Val Asp Lys Met Gln Asp Glu Phe
    290                 295                 300
```

HUMAN SERPIN POLYPEPTIDES

This application is a divisional of U.S. patent application Ser. No. 10/094,944, filed Mar. 8, 2002, now U.S. Pat. No. 3,958,387 which claims the benefit under 35 U.S.C. 119(e) of U.S. provisional application Ser. No. 60/274,519, filed 8 Mar. 2001; and Ser. No. 60/274,522, filed 8 Mar. 2001; all of which are incorporated in their entirety by reference herein.

FIELD OF THE INVENTION

This invention relates to Thypin and other new members of the human serpin polypeptide family, and to methods of making and using such serpin polypeptides.

BACKGROUND OF THE INVENTION

"Serpin" is a name given to members of a group of single-chain 40–60 kDa proteins many of which are serine protease inhibitors, an activity from which the family originally derived its name (for reviews, see for example, Bird, *Results Probl Cell Differ* 24:63–89 (1998); Pemberton, *Cancer J* 10(1):1–11 (1997); Worrall et al., *Biochem Soc Trans* 27(4):746–50 (1999); and Irving et al., *Genome Res* 10:1845–64 (2000)). Serpins are conserved at the primary amino acid sequence level and also in their tertiary structure. Serpin family members generally share about 15–50% amino acid sequence identity. Three-dimensional computer generated models of the serpins are virtually superimposable. Serpins are found in vertebrates and animal viruses, plants and insects, and identified members of this superfamily number nearly 300.

Serpins may localize to the intracellular or extracellular space, the latter being mediated by a classical N-terminal signal sequence. A subset of the serpin family, the ovalbumin-like serpins (or "ov-serpins"), have a non-cleavable facultative signal sequence found near the N-terminus (Remold-O'Donnell, *FEBS Letters* 315:105–108 (1993)). Ov-serpins that possess this non-canonical signal sequence can demonstrate dual localization inside and outside the cell and are suspected to inhibit different intracellular and extracellular proteases. An example of a serpin with dual localization is PAI-2. Regulation of this dual localization may result in elevated plasma levels associated with various pathologies, such as SCCA in squamous cell carcinoma (Pemberton, 1997).

Serine proteases, which provide the targets for many of the inhibitory serpins, are involved in, and regulate, many aspects of biology including: degradation of extracellular matrix (such as elastases), vascular hemostasis (such as thrombin in coagulation, plasmin in thrombolysis), complement activation (such as complement factors), vasodilation in inflammation and hypertension (such as kallikreins), and digestion (such as trypsin). Leukocytes produce and store in vesicles many different serine proteases involved in cytotoxic responses (e.g. granzymes, chymases). Serpins also play a role in cell migration.

Serpin family members participate in variety of intracellular and extracellular processes, including serving as chaperones for protein folding, storage proteins, and transporting hormones. Inhibitory serpins participate in many important biological activities, including: complement activation; fibrinolysis; coagulation; cellular differentiation; tumor suppression; and selection processes associated with tumor survival (i.e., apoptosis and cell migration). Mutations in serpins may cause a number of diseases, some of which are associated with serpin polymerization (Irving et al, 2000). Such diseases include, for example, blood clotting disorders, emphysema, cirrhosis and dementia.

Many serpins are found at relatively high levels in human plasma. Plasma serpins are variably glycosylated, though this glycosylation may not be required for activity (Potempa et al., *J Biol Chem* 269:15957 (1994)). These include α1 antitrypsin (α1AT), which is involved in restructuring of connective tissue; C1 inhibitor, which controls complement activation; plasminogen activator inhibitors 1 and 2 (PAI-1 and PAI-2), which help control fibrinolysis; and antithrombin, which is involved in regulating the coagulation cascade. Also present in blood are angiotensinogen, which when cleaved gives rise to vasopressor peptide that helps control blood pressure, as well as thyroxine binding globulin (TBG) and the corticosteroid binding globulin (CBG). Proteolytic cleavage of TBG appears to provide a mechanism for site-specific release of thyroxine (Schussler, *Thyroid* 10(2): 141–49 (2000)). The serpins maspin, PAI-2 and α1AT, under certain circumstances are capable of polymerizing (Pemberton, 1997). Some serpins, such as AT-III, achieve a much higher level of inhibitory activity if activated by polysulfated oligosaccharides such as heparin (Potempa et al., 1994). Other serpins shown to bind heparin cofactor II include protease nexin-1, active protein C inhibitor and PAI-1 (Potempa et al., 1994).

The ov-serpins are characterized by their relatively high degree of homology with chicken ovalbumin. The ov-serpins are reviewed, for example, in Worrall et al., 1999 and in Remold-O'Donnell, 1993. Ov-serpins generally have eight exons, seven introns and highly conserved intron-exon boundaries, though the ov-serpin PI-6 has only seven exons and six introns. The ov-serpins typically lack the extended N-terminal and C-terminal regions found in other serpins. Moreover, they possess an internal hydrophobic sequence near the amino terminus that allows both secretion and intracellular retention, depending on the cell type or the state of differentiation of the cell in which the protein is expressed. Ov-serpins have a higher degree of amino acid homology with one another than with the other serpins (e.g., they are 40% to 50% homologous with each other, but only about 30% homologous with the other serpins). In addition, ov-serpins have a penultimate serine at the C-terminus, and they have nearly identical splice-junction positions. The ov-serpins are predominantly intracellular, though some are secreted as well as being found intracellularly (e.g., maspin and PAI-2).

Other physiological processes in which serpins have been implicated include prevention of tumor invasiveness (maspin), storage (ovalbumin) and functioning as a chaperone in protein folding (HSP47) (see, for example, Whisstock et al., *Trends Biochem Sci* 23(2):63–67 (1998); Sauk et al., *Connective Tissue Res* 37 (1–2): 105–119 (1998)). The heat shock protein HSP47, although studied primarily for its role in collagen processing, sometimes escapes from the endoplasmic reticulum and reaches the cell surface, thus prompting Sauk et al. to propose that it could modulate cell migration during development and/or metastatic invasion of cancer cells (Sauk et al., 1998).

The clinical manifestations of serpin dysfunction include emphysema and cirrhosis (whisstock et al., 1998; Bird, 1998), which are associated with deficiencies in α1-proteinase inhibitor (also called "α1-antitrypsin"), which ordinarily control alveolar damage by neutrophil elastase. Accumulation of α1-proteinase inhibitor mutants in liver can give ruse to hepatitis or cirrhosis (Bird, 1998). Defective antithrombin III may underlie recurrent thromboembolic disease, and certain bleeding disorders could be related to deficient α2-antiplasmin activity, which results in higher levels of active plasmin thus increased fibrinolysis, while other clinical manifestations of serpin dysfunction include thrombosis, associated with antithrombin, which targets thrombin thereby inhibiting the coagulation cascade (Bird, 1998). It has been noted also that mutations in antithrombin III and α$_2$-antiplasmin are associated with uncontrolled coagulopathies, and that hereditary angioneurotic edema is associated with deficiencies in C1-inhibitor, which targets C1-elastase and is an enzyme involved in the complement cascade (Potempa et al., 1998; Whisstock, 1998).

It has been noted that many aspects of osteoarthritis and rheumatoid arthritis involve cell invasion, that is, the ability of cells to cross anatomical barriers separating tissue compartments, and that proteases such as plasminogen activators and the matrix metalloproteinases play a role in controlling the activity of invading and proliferating cells in inflamed joints (Del Rosso et al., *Clin Exp Rheumatol* 17:485–98 (1999)). Del Rosso et al. summarize evidence that urokinase plasminogen activator (uPA) plays a key role in extracellular matrix destruction and formation of lesions in arthritic joints. They suggest that pharmacologically controlling the plasminogen activating system may be a viable approach to preventing the development of bone lesions and joint ankylosis in arthritis.

The serpin family also includes viral proteins that play a role in viral virulence. For example the cowpox cytokine response modifier gene (CrmA) can block apoptosis induced by a variety of stimuli, and is known to inhibit several of the interleukin-1β converting enzymes (ICE-like cysteine proteases). CrmA is considered a virulence factor for the cowpox virus. SERP1 (myxoma virus) targets uPA, tissue plasminogen activator (tPA) and plasmin, and promotes myxoma virus virulence.

The ov-serpins appear to be clustered within a 500 kb region telomeric to BCL2 at 18q21.3 (Silverman et al., *Tumor Biol* 19:480–87 (1998)). The two SCCA genes are less than 10 kb apart in this region and are flanked by the genes encoding PAI-2 and maspin (also called SERPINB5 or PI5). Additional serpins mapping to 18q21.3 are the cytoplasmic antiproteinase 2 (CAP2, also called PI8), bone marrow-associated serpin (bomapin, also called PI10 or serpin B10), hurpin (also called SERPINB13 OR "headpin") and megsin. The order of several of these serpins is cen-maspin, hurpin, SCCA-2, SCCA-1, megsin, PAI-2, bomapin and CAP2-tel. The SCCA-2 coding region has been cloned, and is disclosed in WO 9714425. Contigs containing this gene cluster can be found at the NCBI website using the nucleotide search and entering one of the following contig numbers: AC019355; AP001404; or AC015536. Chromosome 18q is known to be associated with breakpoints and loss of heterozygosity in cancers of the head and neck and other malignancies, thus suggesting that intact functioning of the serpin genes within this cluster may be disadvantageous to tumor growth (Spring et al., *Biochem Biophys Res Comm* 264:299–304 (1999)).

Some of the serpins have no discernable protease inhibitory activity, while others have been shown to inhibit serine or cysteine proteases (see, for example, Pemberton, 1997). Most of the ov-serpins inhibit serine proteases, however, SCCA-1, for example, inhibits cysteine proteases such as papain, cathepsins L, S and K, while the closely related SCCA-2 (92% amino acid sequence identity) inhibits chymotrypsin-like serine proteases such as mast cell chymase and cathepsin G. SCCA-1 is found mainly inside of cells, while the more acidic SCCA-2 is largely expressed in squamous cell carcinoma and released outside the cells (Suminami et al., *Tumor Biol* 19:488–93 (1998)). The cowpox CrmA protein also is a cysteine proteinase inhibitor. Hurpin is predicted to be an inhibitory serpin based on its hinge region homology with other serpins that possess this type of activity (Spring et al., (1999).

The basic scaffold possessed by all serpins usually includes nine a helices and three β-pleated sheets. Serpins that inhibit proteinases do so via a reactive site loop or "RSL" of about 20 to 30 amino acids located 30 to 40 amino acids from the carboxy terminus. The RSL is exposed on the surface of the protein and is susceptible to cleavage by non-target proteases (see, for example, Potempa et al., 1994). The core structure of the serpin molecule folds into a three-β-sheet pear shape that presents the RSL at the top of the structure. The RSL contains "bait" sequences that are believed to mimic the target proteinase's substrate. The inhibitory serpins regulate the activity of specific serine proteases by mimicking the protease's substrate and covalently binding to the protease when cleaved at the RSL. Upon cleavage by the target protease, inhibitory serpins undergo a dramatic conformational change, called the "stressed-to-relaxed" transition, which is accompanied by the insertion of the remaining reactive site loop into one of the β sheets. During this transition, serpins form a stable heat-resistant complex with the target protease. The sequence of the RSL, and particular the P1 and adjacent amino acid residues, determine an inhibitory serpin's specificity for a protease. An RSL is considered a key feature of serpin family members, and this structure is presented in the exposed surface loop at the top of the protein even in serpins that are not known to inhibit any proteinases.

Serpins with inhibitory activity possess several regions important in controlling and modulating serpin conformational changes associated with attaching to a target protease. As summarized in Irving et al. (2000), these are the hinge region (the P15–P9 portion of the RSL); the breach (located at top of the A β-sheet, the point of initial insertion of the RSL into the A β-sheet); the shutter (at top of the A β-sheet, the point of initial insertion of the RSL into the A β-sheet); and the gate (including strands s3C and s4C; to insert into the A β-sheet, the RSL must pass around the β-turn linking strands s3C and s4C). Inhibitory serpins possess a high degree of conservation at many key amino acid residues located in the above regions which that are believed to be necessary for enabling the protein to undergo the stressed to relaxed transition (see, for example, Table 2 in Irving et al., 2000).

Serpins lacking protease inhibitory function may exploit their "bait" sequences to attract a proteinase that cleaves within the bait sequence to activate a biological effector. Leukocyte elastase inhibitor (LEI), for example, appears to be converted by the serine protease elastase into a deoxyribonuclease that functions to degrade DNA during apoptosis (discussed in WO 99/58560). Another serpin, thyroxine binding globulin, is proteolytically cleaved to release biologically active T$_4$ at specific locations in the body (Schussler, 2000) and angiotensinogen present in serum is cleaved by its target proteinase to generate the biologically active angiotensin protein. Similarly, corticosteroid binding protein is cleaved by the elastase at inflammatory sites to locally release corticol (Schussler, 2000).

The serpins PAI-1 and PAI-2 are involved in regulating the proteolytic breakdown of the extracellular matrix. Additionally, experiments have shown that PAI-2 protects cells against apoptosis induced by TNFα, apparently by blocking a protease, though PAI-2 does not protect against other apoptotic signals (for review, see Bird, 1998). PAI-2 also has been shown to bind to the anti-inflammatory and growth regulatory lipocortins (annexins). PAI-2 thus may be involved in regulating inflammation or growth factor signaling.

Proteinase inhibitor-9 (PI-9) is an ov-serpin proposed to protect cytotoxic T lymphocytes and natural killer cells from self-induced apoptosis resulting from exposure to granzyme B, an enzyme these lymphocytes produce to induce DNA degradation in target cells (Bird, 1998). PI-9 is not secreted and is apparently restricted to lymphoid tissue. Another inhibitory serpin, protease nexin I (PN-1) is secreted and is a potent heparin-dependent thrombin and urokinase inhibitor (Bird, 1998). It is proposed that PN-1 balances the action of thrombin on neuronal cells, thereby rescuing neural cells from apoptosis that otherwise would be induced by the action of thrombin on receptors on the surface of the neurons (Bird, 1998).

Serpins were originally shown to be involved in suppressing tumor invasion by directly inhibiting the matrix-degrading serine proteases uPA and plasmin produced by some tumor cells. Tumor-produced proteases are believed to facilitate a tumor's ability to metastasize, thus are targets for therapeutic intervention. Some cysteine proteases, such as the calpains, have been implicated in apoptotic pathways involved in tumor surveillance (Pemberton, 1997).

One serpin with demonstrated tumor-suppressing capacity is the ov-serpin maspin. Maspin is found mainly in the membrane fraction of epithelial cells (such as breast and prostate), and its expression is downregulated in mammary tumor epithelium (reviewed in Sager et al., in "Chemistry and Biology of Serpins," eds. Church et al., Plenum Press, NY, 1997, at pages 77–88). Although maspin has been shown to suppress the invasiveness of both breast and prostate tumor cells, it does not appear to inhibit any proteases. Even so, if trypsin is used to cleave the maspin RSL, maspin loses its ability to inhibit tumors. Evidently, maspin interferes with tumor growth by some as-yet-unidentified mechanism that requires an intact RSL.

In some cancers, elevated plasma levels of certain serpins serve as markers of cancer progression. For example, the level of the prostate specific antigen (PSA) in complex with α1AT is used to monitor the progression of prostate cancer (Pemberton, 1997). Another serpin used as a tumor marker for prostate cancer is prostapin, which is described in WO 99/58560. The ov-serpins SCCA-1 and SCCA-2 in fact were originally identified as squamous cell carcinoma antigens, and a monoclonal antibody with which both SCCA's react is commonly used to monitor progression of this type of tumor (Barnes et al., Gynecol Oncol 78:62–66 (2000)). The SCCAs are elevated in squamous cell carcinomas of cervix, lung and esophagus, and SCCA levels are used as a serological marker for the extent of disease in advanced cases of these tumors (Silverman et al., 1998; Barnes et al., 2000). Suminami et al. (1998) report that the SCCA produced in epithelial cancers is primarily SCCA-2, and propose that SCCA-2 normally protects epithelial cells from inflammation. Elevated serum levels of SCCA have also been observed in patients with benign skin disorders with an inflammatory component. Such conditions include psoriasis and eczema (Barnes et al., 2000). SCCA-1 and SCCA-2 are elevated in psoriatic epidermis and are disclosed as psoriasis markers called "psoriastatin 1" and "psoriastatin 2" (WO 97/14425). Another related serpin, hurpin, also is overexpressed in psoriatic skin lesions and is disclosed as a lung tumor antigen (WO 99/47674). Hurpin is expressed in normal oral mucosal tissue, skin and in cultured keratinocytes, but is underexpressed in squamous cell cancers of the oral cavity (Spring et al., 1999). Bomapin is expressed specifically in the bone marrow (Riewald and Schleef, J Biol Chem 270:26754–57 (1995)).

Various serpins are expressed by many tissues in the body (see, for example, Worrall et al., 1999). Those present at high concentrations in the blood generally are synthesized in the liver. PAI-2 and LEI, for example, are expressed in monocytes. Maspin is expressed in normal mammary epithelium (Sager et al., 1997). SCCA-1 and SCCA-2 are expressed in normal and malignant squamous epithelium, particularly in the spinous and granular layers of epidermis and in the intermediate layer of the ectocervical epithelium (Suminami et al., 1998).

In order to develop more effective treatments for conditions and diseases mediated by serpins and their targets, more information is needed about unidentified members of the serpin polypeptide family.

SUMMARY OF THE INVENTION

The present invention is based upon the discovery of new human serpin family members, including Thypin (previously referred to as 'epipin'). The Thypin gene is located within a cluster of related serpin family members at chromosome 18q21.3. Among the serpins, Thypin is most closely related to SCCA-1, SCCA-2 and hurpin, all of which are expressed in psoriatic tissue.

The invention provides an isolated Thypin polypeptide consisting of, consisting essentially of, or more preferably, comprising an amino acid sequence selected from the group consisting of:

(a) the amino acid sequences shown in SEQ ID NO:2;
(b) fragments of the amino acid sequences of (a) comprising at least 20 contiguous amino acids;
(c) fragments of the amino acid sequences of (a) comprising at least 30 contiguous amino acids;
(d) fragments of the amino acid sequences of any of (a)–(c) having Thypin polypeptide activity;
(e) fragments of the amino acid sequences of any of (a)–(c) comprising amino acids from 374 to 395 of SEQ ID NO:2;
(f) amino acid sequences comprising at least 20 amino acids and sharing amino acid identity with the amino acid sequences of any of (a)–(e), wherein the percent amino acid identity is selected from the group consisting of: at least 70%, at least 75%, at least 80%, at least 85%, at least 90%, at least 95%, at least 97.5%, at least 99%, and at least 99.5%;
(g) an amino acid sequence of (f), wherein a polypeptide comprising said amino acid sequence of (f) binds to an antibody that also binds to a polypeptide comprising an amino acid sequence of any of (a)–(e); and
(h) an amino acid sequence of (f) or (g) having Thypin polypeptide activity.

Preferably, such polypeptides are isolated Thypin polypeptides or isolated polypeptides that are variants of Thypin. As used herein, a "variant" is a polypeptide that differs from the amino acid sequence of SEQ ID NO:2 only in conservative substitutions and/or modifications such that the therapeutic, antigenic and/or protease inhibitory properties of the polypeptide are retained. In a preferred embodiment, such substitutions or modifications do not involve the Thypin RSL (amino acids 374–395 of SEQ ID NO:2) and differ from the polypeptide defined by SEQ ID NO:2 by the substitution, deletion or addition of five or fewer amino acids. Preferred Thypin variants share 95% or more amino acid sequence identity with SEQ ID NO:2.

Other aspects of the invention are isolated nucleic acids encoding polypeptides of the invention, and isolated nucleic acids, preferably having a length of at least 15 nucleotides, that hybridize under conditions of moderate stringency to the complement of nucleic acids encoding polypeptides of the invention, such as the nucleotide sequence given in SEQ ID NO:1. In yet other embodiments, the nucleic acids hybridize under highly stringent conditions with the complement of SEQ ID NO:1. In preferred embodiments of the invention, such nucleic acids encode a polypeptide having Thypin polypeptide activity, or comprise a nucleotide sequence that shares nucleotide sequence identity with the nucleotide sequences of SEQ ID NO:1, wherein the percent nucleotide sequence identity is selected from the group consisting of: at least 70%, at least 75%, at least 80%, at least 85%, at least 90%, at least 95%, at least 97.5%, at least 99%, and at least 99.5%. Such nucleic acids preferably encode Thypin, a Thypin variant, or an antigenic fragment thereof. Also encompassed are segments of SEQ ID NO:1 at least 15 nucleotides in length for use as probes for in situ hybridization to chromosome 18q. The invention also provides an isolated genomic nucleic acid corresponding to the nucleic acids of the invention.

Further provided by the invention are expression vectors and recombinant host cells comprising at least one nucleic acid of the invention, and preferred recombinant host cells wherein said nucleic acid is integrated into the host cell genome. In other embodiments, the vector nucleic acid does not become integrated.

Also provided is a process for producing a polypeptide encoded by the nucleic acids of the invention, comprising culturing a recombinant host cell under conditions promoting expression of said polypeptide, wherein the recombinant host cell comprises at least one nucleic acid of the invention. A preferred process provided by the invention further comprises purifying said polypeptide. In another aspect of the invention, the polypeptide produced by said process is provided.

Further aspects of the invention are isolated antibodies that bind specifically to the polypeptides of the invention, preferably monoclonal antibodies, also preferably humanized antibodies or humanized antibodies, and preferably wherein the antibody inhibits the activity of said polypeptides.

The invention additionally provides a method of designing an inhibitor of the polypeptides of the invention, the method comprising the steps of determining the three-dimensional structure of any such polypeptide, analyzing the three-dimensional structure for the likely binding sites of substrates, synthesizing a molecule that incorporates a predicted reactive site, and determining the polypeptide-inhibiting activity of the molecule.

In a further aspect of the invention, a method is provided for identifying compounds that alter Thypin polypeptide activity comprising
 (a) mixing a test compound with a polypeptide of the invention; and
 (b) determining whether the test compound alters the Thypin polypeptide activity of said polypeptide.

In another aspect of the invention, a method is provided identifying compounds that inhibit the binding activity of Thypin polypeptides comprising
 (a) mixing a test compound with a polypeptide of the invention and a binding partner of said polypeptide; and
 (b) determining whether the test compound inhibits the binding activity of said polypeptide.

The invention also provides a method for increasing protease inhibitory activities, comprising providing at least one compound selected from the group consisting of the polypeptides of the invention and agonists of said polypeptides; with a preferred embodiment of the method further comprising increasing said activities in a patient by administering at least one polypeptide of the invention.

Further provided by the invention is a method for decreasing protease inhibitory activity, comprising providing at least one antagonist of the polypeptides of the invention; with a preferred embodiment of the method further comprising decreasing said activities in a patient by administering at least one antagonist of the polypeptides of the invention, and with a further preferred embodiment wherein the antagonist is an antibody that inhibits the activity of any of said polypeptides.

The invention additionally provides a method for treating conditions and diseases mediated by Thypins and their targets, comprising administering at least one compound selected from the group consisting of the polypeptides of the invention and agonists of said polypeptides; with a preferred embodiment wherein the condition or disease mediated by Thypins or their targets is selected from the group consisting of emphysema, cirrhosis, hepatitis, blood clotting disorders (including thrombosis), tumor formation, and tumor metastasis or invasiveness.

In other aspects of the invention, a method is provided for treating conditions and diseases mediated by Thypins and their targets, comprising administering an antagonist of the polypeptide of the invention; with a preferred embodiment wherein the condition or disease mediated by Thypins or their targets is viral virulence.

A further embodiment of the invention provides a use for the polypeptides of the invention in the preparation of a medicament for treating conditions and diseases mediated by Thypins and their targets; with a preferred embodiment wherein the condition or disease mediated by Thypins or their targets is selected from the group consisting of emphysema, cirrhosis, hepatitis, blood clotting disorders, tumor formation, and tumor metastasis or invasiveness.

A further embodiment of the invention provides a use for the polypeptides of the invention in the preparation of a medicament for treating medical conditions associated with Thypin dysfunction.

DETAILED DESCRIPTION OF THE INVENTION

Figure 1:
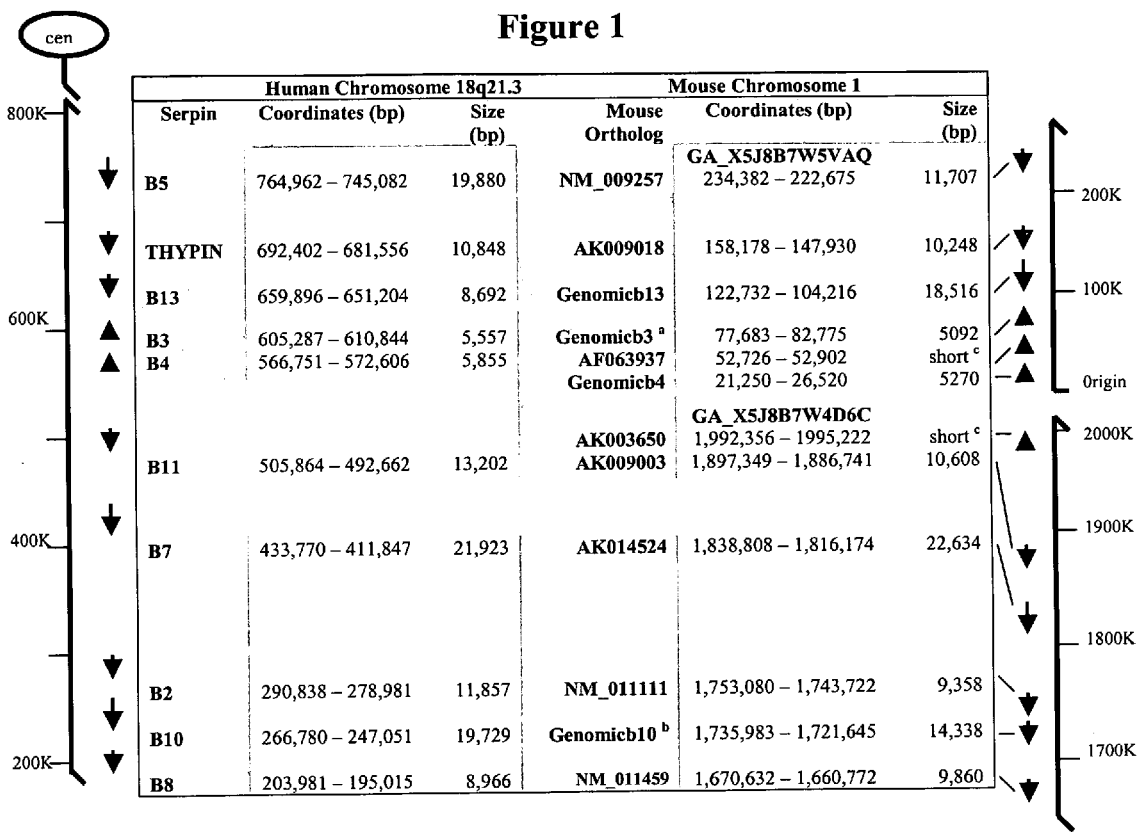
FIG. 1. Syntenic organization of human chromosome 18 and mouse chromosome 1 serpin clusters. The relative positions and transcriptional orientations of the chromosome 18 ov-serpins on contig NT 010986.2 are shown as arrows on the line diagram. Mouse cDNAs with highest homology to their human orthologs are similarly mapped to their respective genomic scaffold. The nucleotide coordinates are presented from the initiator methionine to the terminal codon in the coordinates column of the table. The size column presents the length of these genes in basepairs (bp). The following genomic sequences do not encode complete open reading frames: [a]Genomicb3 sequence has a stop codon in the middle of the ORF; [b]missing sequence at exon 7 splice junction; [c]short sequences: exact matches exist for the second exon encoding AF063937 and exons 4, 6, 7, and 8 of AK003650.

We have identified Thypin (previously named 'epipin'), a new serpin polypeptide having structural features characteristic of this polypeptide family. A splice variant of Thypin, SERPINB12 (also called Yukopin), has been published as GenBank accession number AF411191. The amino acid sequence of a representative human Thypin polypeptide is provided in SEQ ID NO:1 and a nucleotide sequence encoding this polypeptide is provided in SEQ ID NO:2. An alignment showing the sequence similarities between Thypin and serpin polypeptides is presented in Table 2 in Example 1 below. It is apparent from amino acid sequence homology, predicted tertiary structure homology, and chromosome 18 localization that Thypin is an ov-serpin. The most closely related to Thypin from among the known serpins is SCCA-2, with which Thypin shares about 51% amino acid sequence homology. The mouse homologue of Thypin has GenBank accession number AK009018. Mouse Thypin (AK009018) is located on mouse chromosome 1 in an ov-serpin cluster that contains known mouse ov-serpin genes for Serpinb2, Serpinb5 and Serpinb7 (see Example 7 below).

Thypin contains domains similar to those found in other ov-serpins (see Remold-O'Donnell, 1993). One of these is a hydrophobic region located near the amino terminus. This hydrophobic region, though not cleaved, serves as a signal sequence for serpins that enter the extracellular space. Thypin possesses such a hydrophobic region, which was identified as a signal sequence according to the method of Heijne (*Nucleic Acids Res* 14(11):4683–4690 (1986)). The predicted Thypin signal sequence aligns well with known ov-serpin signal sequences, and extends from amino acids 28 to 42 in SEQ ID NO:2. Relative to most of the other ov-serpins, Thypin has an insertion located at approximately amino acids 61 to 107 of SEQ ID NO:2. This region is identified as the interhelical variable loop region because it occurs between two conserved helices (see Remold-O'Donnell, 1993). In other serpins, the interhelical variable loop is exceedingly variable in length and amino acid composition. In Thypin, this region is unusually large due to the insertion, but this circumstance does not interfere with the canonical serpin fold. The Thypin insertion is located between two conserved ov-serpin helices (helix C and helix D). PAI-2 also has a large insertion at this same location. The insertion at amino acids 61 to 107 of SEQ ID NO:2 is also present in SERPINB12/Yukopin, except for twenty amino acids specific to Thypin at amino acids 82 through 101 of SEQ ID NO:2, which may be a trans-glutamination site. The AK009018 murine Thypin polypeptide also includes the Thypin-specific potential transglutamination residues. The discrepancy between Thypin and Yukopin results from the use of different 5' splice sites in intron C; the 3' splice site is identical. The Thypin 5' splice site for intron C is located following nucleotide 303 of SEQ ID NO:1; Yukopin uses a 5' splice site 60 nucleotides upstream within Exon 2 (between nucleotides 243 and 244 of SEQ ID NO:1) with an atypical exon-side ultimate adenine found in 8% of vertebrate splice sites (Padgett et al., 1986, *Ann Rev Biochem* 55: 1119–1150): AAA/gtgctg (nucleotides 241 through 249 of SEQ ID NO:1). There is precedent for alternative splicing in the ov-serpins as a SERPINB13 variant has been described with an insertion in the C–D interhelical loop (Spring et al., 1999, *Biochem Biophys Res Comm* 264: 299–304). Intron/exon splice site phasing is conserved in ov-serpins and has been used to predict evolutionary relatedness of members of the serpin superfamily. Ov-serpins have six introns (A, B, D, E, F, and G) that occur in conserved locations. Intron C, found in a subset of the ov-serpins, is located in the C–D interhelical loop and the exact location is not conserved between serpins. Thypin possesses a high proportion of glutamines in the C–D interhelical loop (5/47 or 10.6% as compared to 6.2% expected (McCaldon and Argos, 1988, *Proteins* 4: 99–122; murine Thypin has 6/45 or 13.3% glutamines in the C–D interhelical loop). The deletion in Yukopin eliminates three of the five glutamines present in human Thypin. It is interesting to speculate that this difference between Thypin and Yukopin may result in a functional difference in the ability to be crosslinked by transglutamination.

Moving from the hypervariable region towards the COOH-terminus, the ov-serpins possess a region within which there is a relatively high degree of conservation. In Thypin, this region extends from approximately amino acid 108 to amino acid 373 of SEQ ID NO:2. This relatively conserved region is referred to herein as the "structural core" region. The serpin RSL is located further towards the COOH-terminus past the structural core region. Based on amino acid homologies, the RSL in Thypin is approximately 22 amino acids long, and extends from amino acids 374 to 395 in SEQ ID NO:2. According to the naming convention for proteolytic cleavage sites of known serpins, amino acid residue 374 is the P17 amino acid and amino acid 395 is P5'. These designations place the scissile bond between the arginine at position 390 (P1) and the serine at position 391 (P1'). Cleavage by the target protease is expected to occur between P1 and P1'. Following the RSL, serpin family members contain a highly conserved serpin signature motif. The Thypin amino acids between residues 398–408 of SEQ ID NO:2 precisely match this serpin signature motif. Therefore, the foregoing structural features indicate that the Thypin polypeptide has an overall primary structure consistent with other ov-serpins.

The skilled artisan will recognize that the boundaries of the regions of Thypin polypeptides described above are approximate and that the precise boundaries of such domains can also differ from member to member within the serpin polypeptide family.

To further establish the classification of Thypin as a member of the serpin structural family, the Thypin sequence was submitted to GeneFold (Tripos, Inc., St. Louis, Mo.; Berman et al., *Nucleic Acids Res* 28:235–242 (2000)) which is a protein threading program that overlays a query protein sequence onto structural representatives of the Protein Data Bank (PDB) (Jaroszewski et al., *Prot Sci* 7:1431–40 (1998)). Serpin family members, despite their diversity, are characterized by a highly characteristic three-dimensional structure that can be predicted from their primary amino acid sequences by using protein-threading algorithms such as GeneFold. To use GeneFold to classify new members of a protein family, the new protein sequence is entered into the program, then is assigned a probability score that reflects how well it folds onto previously known protein structures ("template" structures) that are present in the GeneFold database. For scoring, GeneFold relies on primary amino acid sequence similarity, burial patterns of residues, local interactions and secondary structure comparisons. In using GeneFold, the amino acid sequence is folded (or threaded) onto all of the template structures in a preexisting database of protein folds, which includes the solved structures for several serpins. For each comparison, the program first determines the optimal alignment, and then calculates the probability (P-value) that this degree of alignment occurred by chance. The inverse of the P-value is determined for the query sequence threaded onto each template structure, and this inverse P-value is reported as a score. Three different scores are actually calculated for each hit and are reported in three columns. These three scores are based on (i) sequence only; (ii) sequence plus local conformation preferences plus burial terms; and (iii) sequence plus local conformation preferences plus burial terms plus secondary structure. All scores above the designated cutoff are returned, along with the associated template identifier for each column. These scores therefore reflect the degree to which the new protein matches the various reference structures. The scores thus are useful for assigning a new protein to membership in a known family of proteins. The highest possible score using Gene-Fold is 999.999. When threaded into the GeneFold program, the ov-serpins LEI (SwissProt No. P30740), PAI-2 (GenBank No. XP_008746), SERPINB10 (bomapin) (GenBank No. NP_005015), SCCA-1 (SwissProt No. P29508), SCCA-2 (SwissProt No. P48594) and prostapin (GeneSeq No. Y15156) all had scores of 999.99 in all three columns relative to the top five hits. In each instance, all of the top five hits were serpins, thus illustrating the high degree of structural conservation among this group of proteins.

After threading against all structures in the GeneFold database, Thypin scored 999.99 in all three types of score (i.e., all three columns) with five different known serpins in the GeneFold database. The PDB hits in the order listed by GeneFold are: 1ovaA (Ovalbumin), 1hleA (Horse Leukocyte Elastase Inhibitor), 2antI (Antithrombin), 1atu (alpha-1-Antitrypsin), and 1as4A (Antichymotrypsin). The GeneFold results give a clear indication that Thypin is a serpin. However, extracting the alignment against 1ovaA shows a large insertion present in the Thypin interhelical variable loop region (amino acids 80 to 111 of SEQ ID NO:2). The insertion was mapped onto the structure of 1ovaA using the Molecular Operating Environment (MOE) from the Chemical Computing Group (1010 Sherbrooke St W, Ste 910, Montreal, Quebec, Canada H3A 2R7) and is found on a loop that is isolated from secondary structure elements. A simple loop extension is all that is required to fold Thypin as a serpin.

When Thypin variants according to the invention, such as allelic variants with normal bioactivity or mutants with altered bioactivity, are analyzed using GeneFold, the top five hits obtained will be serpins, and the score for the top five hits will be 999.999. A score of 999.999 will be obtained for these five hits using any of the three types of score reported by GeneFold, i.e., sequence only, sequence plus local conformation preferences plus burial terms, or sequence plus local conformation preferences plus burial terms plus secondary structure. Such Thypin variants are distinguished from other serpins by virtue of containing particular amino acid sequences that differentiate Thypin from other known serpins. Particular amino acid regions that differentiate Thypin from other serpins include but are not limited to the Thypin insertion loop from amino acids 61 to 107 of SEQ ID NO:2; the Thypin core region from amino acid 108 to 373 of SEQ ID NO:2; and the Thypin RSL from amino acid 374 to 395 of SEQ ID NO:2. Thypin variants typically will contain about 425 amino acids, but such variants may contain deletions or insertions of around 5 amino acids while still retaining the bioactivity associated with the Thypin polypeptide represented in SEQ ID NO:2.

A partial human cDNA clone (AA242969) in the GenBank dbEST database contains an open reading frame that predicts a protein having 95% identity to amino acids 69–250 of the Thypin polypeptide shown in SEQ ID NO:2. This EST-encoded polypeptide thus encompasses the above-discussed Thypin insertion (amino acids 61–107 of SEQ ID NO:2), and partially encompasses the Thypin structural core (amino acids 108–373 of SEQ ID NO:2). This EST protein differs from Thypin at eight amino acid residues, which correspond in position to amino acids 109, 115, 118, 126, 127, 216, 246 and 248 of SEQ ID NO:2. The amino acids present in the EST at those locations are, respectively, threonine, asparagine, lysine, phenylalanine, arginine, isoleucine, proline and phenylalanine, whereas in Thypin the corresponding amino acids, respectively, are serine, tyrosine, glutamine, isoleucine, lysine, lysine, glutamine and tyrosine. One embodiment of the invention includes Thypin variants having about 95% or greater amino acid sequence identity with SEQ ID NO:2, and further possessing at least one of the following: a serine at residue 109; a tyrosine at residue 115; a glutamine at residue 118; an isoleucine at residue 126; a lysine at residue 216 or 246; a glutamine at residue 246; or a tyrosine at residue 248. Optimally, these Thypin variants will possess protease inhibitory activity. It should be noted that the polypeptide predicted by EST AA242969 lacks an RSL, thus cannot fold into a serpin structure nor can it exhibit the protease inhibitory activity of Thypin.

Nucleic acid sequence analysis adds further support for the conclusion that Thypin is an ov-serpin. The Thypin gene has been localized to chromosome 18 on the NCBI human chromosomal contigs AC019355, AP001404 and AC015536. These contigs contain genomic sequence for both Thypin and hurpin, thus indicating their linkage. Radiation hybrid mapping of hurpin localizes this gene to chromosome 18q21.3/18q22, juxtaposed to a cluster of ov-serpins (Spring et al., 1999). Analysis of the genomic sequence of Thypin shows that its intron splice site junctions match conserved exon-intron borders of ov-serpin family members, a feature that distinguishes them from other members of the serpin superfamily (Remold-O'Donnell, 1993).

Serpins that inhibit proteases tend to be specific for one or a few proteases. Inhibitory serpins form a 1:1 stoichiometric, heat and denaturation resistant complex with their target protease. The RSL is an important structural determinant of the inhibitory serpins. The sequence of the peptide stalk leading from the A sheet to the commencement of the helix, known as the hinge region (P15–P9), is highly conserved in inhibitory serpins, and mutations in this region can result in loss of inhibitory activity (Huber and Carrell, *Biochemistry* 28:8951 (1989); Potempa et al., 1994). Within the hinge region, P12–P9 shows a dominance of residues with small side chains, which usually are alanines or glycines (Stein et al., *Nature* 347: 99–102 (1990)). Stein et al. proposes that this alanine-rich region contributes to the flexibility of the stalk, and that mobility of the stalk is necessary for inhibitory action. The hinge region of Thypin (corresponding to amino acids 376–382 of SEQ ID NO:2) matches the consensus for the 40 inhibitory serpins analyzed by Potempa et al. (Potempa et al., 1994), including four consecutive alanines (amino acids 379–382 of SEQ ID NO:2) in the alanine-rich stalk, thus indicating that Thypin is a member of the inhibitory serpin subfamily.

It is possible to predict what class of protease is inhibited by a serpin based on the amino acid in the P1 position of the RSL. Thypin has an arginine at P1, thus indicating that it is likely to inhibit one or more arginine-cleaving proteases. Consistent with this prediction, recombinant Yukopin is an inhibitor of trypsin-like serine proteases (Askew et al., 2001, J Biol Chem 276: 49320–49330). It is expected that Thypin would have the same in vitro activity as Yukopin since the C–D interhelical loop does not appear to have a role in protease inhibitory activity. (An interesting difference between the human and mouse Thypin homologs is that the mouse RSL has a PI lysine instead of arginine.) Many arginine-cleaving proteases are present in human serum and tissues. Inhibitory serpins with an arginine at P1 include PAI-1, which targets uPA and tPA, PAI-2, which targets uPA and tPA, anti-thrombin, which targets the serine protease thrombin, and C1-inhibitor, which targets C1-esterase (see Whisstock et al., 1998). Serine proteases with P1 arginine specificity that are potential therapeutic targets for inactivation by Thypin include but are not limited to: trypsin, tryptase, kallikrein, tonin, thrombin, protein C, uPA, tPA, plasmin, coagulation factors VIIa, IXa, Xa, XIa, and XIIa, complement factors 1, B and D, complement components C1 and C2, granzymes A and K, hepsin, prostasin, follipsin, acrosin, and hepatocyte growth factor activator.

PCR amplification from tissue-specific cDNA libraries was performed to detect Thypin cDNA sequences. The results of these experiments showed that Thypin transcripts are expressed in a wide variety of fetal cells and adult cells, including the following: bronchial epithelium; prostate epithelium; breast epithelium; and small airway epithelium. In addition, Thypin is expressed in the following epithelial tissues: prostate; testis; thymus; tonsil; skin; keratinocytes; cervix; fetal small intestine; and esophagus. In addition, Thypin is expressed in the following carcinoma and transformed cell lines: lung epithelial carcinoma (A549); B cell lymphoma (Akata, Nalm6, Namalwa); cancer cells of monocytic origin (U937, Thp-1, AML5); and tumor xenografts (colon, pancreas, prostate). Thypin expression also was observed in miscellaneous tumors originating from lung and esophagus. The primers used to amplify Thypin sequences should amplify Yukopin cDNA as well, but in our PCR examination of greater than 100 different tissue cDNAs we have not identified a size polymorphism consistent with a 20-amino acid (60-nucleotide) difference. This could result from limited agarose gel resolution or lack of the Yukopin mRNA in the tissues we examined. We sequenced nine PCR products from different tissues through the interhelical loop and identified only the Thypin sequence described herein.

The SCCAs also are expressed in normal squamous epithelial tissue (e.g., tongue, tonsil, esophagus, Hassall's corpuscles of the thymus, and skin), which is similar to the expression pattern observed here for Thypin. Also, the SCCAs are elevated in squamous cell carcinomas of cervix, lung and esophagus. Thypin similarly is expressed also in carcinoma tissue (i.e. Gl112 colon adenocarcinoma). Both SCCA1 and SCCA2 are elevated in psoriatic epidermis (see WO 97/14425). Another related serpin, hurpin, also is overexpressed in psoriatic skin lesions and is described as a lung tumor antigen (WO 99/47674).

The above-described pattern of Thypin expression indicates that normal expression of Thypin, like the related SCCA-2, is largely confined to tissues rich in squamous epithelium, thus suggesting that Thypin can serve as a marker for epithelial tissues, such as, for example, in providing epithelium-specific antibodies for tagging epithelial cells in histological preparations, or for determining whether cells of epithelial origin are present in a tumor biopsy.

In some cancers, a serpin that normally is intracellular will assume a bitopological distribution. An example of such a serpin is SCCA-2, which is present in high amounts in the extracellular compartments only in conjunction with a pathological condition such as squamous cell carcinoma. Similarly, redistribution of Thypin from a primarily intracellular location to bitopological intracellular/extracellular location may provide an indicator for particular types of cancer. Bird (1998) also notes that while the intracellular form of PAI-2 is most abundant form, levels of the secreted form increase during pregnancy, inflammation and malignancy.

Like SCCA-1 and SCCA-2, Thypin may be useful as a psoriasis marker, or like maspin, Thypin may be useful as a tumor suppressor. In addition, modulation of Thypin expression or activity may find use in regulating vascular hemostatis, in treating emphysema or cystic fibrosis or in preventing complications of coronary bypass surgery.

In epithelial cell lines and the Thp-1 cell line, Thypin expression appears to become elevated in response to induction with the tumor promoter phorbol myristic acid (PMA) or by infection with *Yersinia enterolytia*. The latter finding indicates that detecting increased levels of Thypin transcripts or detecting increased levels of Thypin protein in infected tissues can provide a rapid diagnostic for *Yersinia* infection thus assisting in control of disease caused by *Yersinia* spp. Such diseases include plague and diarrhea. Also, detection of increased Thypin expression can serve as a diagnostic to determine if tissues have been exposed to tumor promoters such as PMA.

In addition to the above, protease-Thypin complexes may serve as a chemoattractant for neutrophils and monocytes.

As described in Example 5 below, the Thypin gene has been mapped to human chromosome 18q21.3. Thus, the Thypin nucleotide sequences set forth in SEQ ID NO:1 provide a useful tool for tagging chromosome 18q21.3 in histological preparations of human chromosomes. Such procedures using Thypin probes can serve as a diagnostic tool for analyzing cells in a tumor biopsy to determine whether there has been a breakpoint or loss of heterozygosity at this location in chromosome 18. Such knowledge could be useful for predicting the patient's response to various treatment options. Procedures for in situ hybridization to chromosomes are known in the art and typically employ labeled probes of sufficient length to form stable nucleic acid duplexes with the target sequences present in chromosomes that have been fixed to a slide and that have been treated to denature the chromosomal DNA. Suitable probes for this purpose correspond to nucleotide sequences of SEQ ID NO:1, and are at least 15 nucleotides in length, and more preferably are 30 or more nucleotides in length.

Typical biological activities or functions associated with Thypin polypeptides include the inhibition of proteases. Thypin is likely to inhibit one or more proteases found in the serum, extracellular matrix or intracellular space. Protease inhibitory activity is associated with the RSL domain of Thypin polypeptides (amino acids 376–395 of SEQ ID NO:2). Thus, for uses requiring RSL activity, preferred Thypin polypeptides include those having the Thypin RSL domain and exhibiting the ability to inhibit proteases present in serum or extracellular matrix.

Preferred Thypin polypeptides comprise the Thypin RSL and retains specific protease inhibitory capacity of the Thypin protein whose amino acid sequence is shown in SEQ ID NO:2. The protease inhibitory activity of Thypin polypeptides may be determined, for example, in an assay that measures release of polypeptide fragments resulting from the incubation of intact extracellular matrix proteins or intact serum proteins with purified recombinant Thypin. Alternatively, Thypin protease inhibitory activity may be detected by incubating a labeled purified recombinant serpin having the Thypin RSL with serum proteins or extracellular matrix proteins, boiling the mixture in the presence of sodium dodcecyl sulfate, then analyzing the product to determine whether the Thypin has undergone a change consistent with the Thypin having formed a stable heat-resistant complex with a target protease. For example, the boiled mixture can be analyzed by using SDS-polyacrylamide gel electrophoresis, as described in Riewald and Schleef, 1995. The Thypin-protease complexes thus identified can be further analyzed to determine the identity of the protease. As an alternative to using mixtures of serum proteins or extracellular matrix proteins, the assays may employ specific proteases known to form complexes with closely-related serpins. Such proteases include but are not limited to: trypsin, tryptase, kallikrein, tonin, thrombin, protein C, uPA, tPA, plasmin, coagulation factors VIIa, IXa, Xa, XIa, and XIIa, complement factors 1, B and D, complement components C1 and C2, granzymes A and K, hepsin, prostasin, follipsin, acrosin, and hepatocyte growth factor activator To exhibit protease inhibitory activity, the Thypin RSL must be present in a serpin molecule having the serpin tertiary structure that ensures presentation of the RSL in the loop at the top of the structure. Thus, to exhibit activity, the Thypin RSL must be present in an intact Thypin molecule, or alternatively, a different serpin molecule can be engineered to substitute the Thypin RSL for its native RSL.

Thus, for uses requiring protease inhibitory activity, preferred Thypin polypeptides include those having the RSL domain (amino acids 374–395 of SEQ ID NO:2) and capable of forming heat-resistant complexes with serum proteins or extracellular matrix proteins. The protease inhibitory activity of Thypin polypeptides may be determined, for example, in an assay that measures Thypin-protease complexes, or in an assay that measures the ability of the target protease to cleave the protein that is its natural target. The degree to which individual members of the Thypin polypeptide family and fragments and other derivatives of these polypeptides exhibit these activities can be determined by standard assay methods, particularly assays such as chromatography and polyacrylamide gel electrophoresis.

Another aspect of the biological activity of Thypin polypeptides is the ability of members of this polypeptide family to bind particular binding partners such as Thypin-specific antibodies, target proteases or any other biological molecule that normally interacts with Thypin. The term "binding partner," as used herein, includes target proteases, ligands, receptors, substrates, antibodies, and any other molecule that interacts with a Thypin polypeptide through contact or proximity between particular portions of the binding partner and the Thypin polypeptide. Because the RSL domain of Thypin polypeptides determines the Thypin binding specificity to a binding partner(s), the RSL domain when expressed as a separate fragment from the rest of a Thypin polypeptide, or as a soluble polypeptide, fused for example to an immunoglobulin Fc domain, may be capable of disrupting the binding of Thypin polypeptides to their binding partners thus inhibiting the biological activities mediated via binding of Thypin polypeptides to its natural target(s). Suitable assays to detect or measure the binding between Thypin polypeptides and their binding partners include the chromatographic assays described above.

Serpin polypeptides are involved in a variety of diseases or conditions. Such diseases may involve over expression of the serpin in question, or expression of an aberrant version of this serpin. Blocking or inhibiting the interactions between members of the Thypin polypeptide family and their target proteases or other binding partners, and/or other interacting polypeptides is an aspect of the invention and provides methods for treating or ameliorating these diseases and conditions through the use of inhibitors of Thypin polypeptide activity. For conditions involving too little Thypin polypeptide activity, methods of treating or ameliorating these conditions comprise increasing the amount or activity of Thypin polypeptides by providing isolated Thypin polypeptides or active fragments, or by providing compounds (agonists) that activate endogenous or exogenous Thypin polypeptides. Preferred methods of administering Thypin polypeptides to organisms in need of treatment, such as mammals or most preferably humans, include local or systemic administration, injection, slow-release implants, aerosol inhalation, and may involve polyethylene glycol derivatives of Thypin.

Additional uses for Thypin polypeptides include use as diagnostic reagents for cancers characterized by locally elevated Thypin expression or by elevated serum levels of Thypin.

Thypin Polypeptides

An Thypin polypeptide is a polypeptide that shares a sufficient degree of amino acid identity or similarity to the Thypin polypeptide of SEQ ID NO:2 to be identified by those of skill in the art as a polypeptide likely to share particular structural domains and/or to have biological activities in common with the Thypin polypeptide of SEQ ID NO:2 and/or to bind to antibodies that also specifically bind to other Thypin polypeptides. Thypin polypeptides may be isolated from naturally occurring sources, or have the same structure as naturally occurring Thypin polypeptides, or may be produced to have structures that differ from naturally occurring Thypin polypeptides. Polypeptides derived from any Thypin polypeptide by any type of alteration (for example, but not limited to, insertions, deletions, or substitutions of amino acids; changes in the state of glycosylation of the polypeptide; refolding or isomerization to change its three-dimensional structure or self-association state; and changes to its association with other polypeptides or molecules) are also Thypin polypeptides. Therefore, the polypeptides provided by the invention include polypeptides characterized by amino acid sequences similar to those of the Thypin polypeptides described herein, but into which modifications are naturally provided or deliberately engineered. A polypeptide that shares biological activities in common with Thypin polypeptides is a polypeptide having Thypin polypeptide activity.

The present invention provides both full-length and mature forms of Thypin polypeptides. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable mammalian cell or other host cell, of a nucleic acid molecule that encodes the full-length polypeptide. The sequence of the mature form of the polypeptide may also be determinable from the amino acid sequence of the full-length form, through identification of signal sequences or protease cleavage sites.

The Thypin polypeptides of the invention also include those that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1–5 terminal amino acids).

The invention further includes Thypin polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the invention can be incubated with a molar excess of glycopeptidase (Boehringer Mannheim).

Species homologues of Thypin polypeptides and of nucleic acids encoding them are also provided by the present invention. As used herein, a "species homologue" is a polypeptide or nucleic acid with a different species of origin from that of a given polypeptide or nucleic acid, but with significant sequence similarity to the given polypeptide or nucleic acid, as determined by those of skill in the art. Species homologues may be isolated and identified by making suitable probes or primers from polynucleotides encoding the amino acid sequences provided herein and screening a suitable nucleic acid source from the desired species. The invention also encompasses allelic variants of Thypin polypeptides and nucleic acids encoding them; that is, naturally-occurring alternative forms of such polypeptides and nucleic acids in which differences in amino acid or nucleotide sequence are attributable to genetic polymorphism (allelic variation among individuals within a population).

Fragments of the Thypin polypeptides of the present invention are encompassed by the present invention and may be in linear form or cyclized using known methods, for example, as described in H. U. Saragovi, et al., Bio/Technology 10, 773–778 (1992) and in R. S. McDowell, et al., J. Amer. Chem. Soc. 114 9245–9253 (1992). Polypeptides and polypeptide fragments of the present invention, and nucleic acids encoding them, include polypeptides and nucleic acids with amino acid or nucleotide sequence lengths that are at least 25% (more preferably at least 50%, or at least 60%, or at least 70%, and most preferably at least 80%) of the length of a Thypin polypeptide and have at least 60% sequence identity (more preferably at least 70%, at least 75%, at least 80%, at least 85%, at least 90%, at least 95%, at least 97.5%, or at least 99%, and most preferably at least 99.5%) with that Thypin polypeptide or encoding nucleic acid, where sequence identity is determined by comparing the amino acid sequences of the polypeptides when aligned so as to maximize overlap and identity while minimizing sequence gaps. Also included in the present invention are polypeptides and polypeptide fragments, and nucleic acids encoding them, that contain or encode a segment preferably comprising at least 8, or at least 10, or preferably at least 15, or more preferably at least 20, or still more preferably at least 30, or most preferably at least 40 contiguous amino acids. Such polypeptides and polypeptide fragments may also contain a segment that shares at least 70% sequence identity (more preferably at least 70%, at least 75%, at least 80%, at least 85%, at least 90%, at least 95%, at least 97.5%, or at least 99%, and most preferably at least 99.5%) with any such segment of any Thypin polypeptide, where sequence identity is determined by comparing the amino acid sequences of the polypeptides when aligned so as to maximize overlap and identity while minimizing sequence gaps. The percent identity can be determined by visual inspection and mathematical calculation. Alternatively, the percent identity of two amino acid or two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website, or the UW-BLAST 2.0 algorithm, using standard default parameter settings described at the blast-wustl website. In addition, the BLAST algorithm uses the BLOSUM62 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton J C and Federhen S, 1996, Analysis of compositionally biased regions in sequence databases, *Methods Enzymol.* 266: 554–71) or segments consisting of short-periodicity internal repeats (as determined by the XNU program of Clayerie & States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The present invention also provides for soluble forms of Thypin polypeptides comprising certain fragments or domains of these polypeptides. Soluble polypeptides are Thypin polypeptides that are capable of being secreted from the cells in which they are expressed. Soluble Thypin polypeptides also include those polypeptides which include the hydrophobic signal sequence found at amino acids 28 to 42 of SEQ ID NO:2, provided that the soluble Thypin polypeptide is capable of being secreted from a cell, and preferably retains Thypin polypeptide activity. Alternatively, a signal sequence capable of directing secretion may be fused to Thypin using recombinant gene expression technology. A secreted soluble Thypin polypeptide may be identified by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of Thypin polypeptides is advantageous for many applications. Purification of the polypeptides from recombinant host cells is facilitated, since the soluble polypeptides are secreted from the cells. Moreover, soluble polypeptides are generally more suitable than intracellular forms for parenteral administration and for many enzymatic procedures.

Further modifications in the peptide or DNA sequences can be made by those skilled in the art using known techniques. Modifications of interest in the polypeptide sequences may include the alteration, substitution, replacement, insertion or deletion of a selected amino acid. For example, one or more of the cysteine residues may be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the polypeptide can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. No. 5,071,972 and EP 276,846. Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide or a substantial equivalent thereof. One example is a variant that binds with essentially the same binding affinity as does the native form. Binding affinity can be measured by conventional procedures, e.g., as described in U.S. Pat. No. 5,512,457 and as set forth herein.

Useful derivatives of Thypin include fusion polypeptides that comprise peptides that are added to facilitate purification and identification of recombinantly expressed Thypin. Such peptide tags include, for example, poly-His or the antigenic identification peptides described in U.S. Pat. No. 5,011,912 and in Hopp et al., Bio/Technology 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Nucleic Acids Encoding Thypin Polypeptides

Encompassed within the invention are nucleic acids encoding Thypin polypeptides. These nucleic acids can be identified in several ways, including isolation of genomic or cDNA molecules from a suitable source. Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a Thypin polypeptide or a desired combination of Thypin polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., Science 239:487 (1988); Recombinant DNA Methodology, Wu et al., eds., Academic Press, Inc., San Diego (1989), pp. 189–196; and PCR Protocols: A Guide to Methods and Applications, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid molecule" is one that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, isolated nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably under highly stringent conditions, to the complement of nucleic acid molecules that encode the Thypin polypeptides described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3–6.4), and can be readily determined by those having ordinary skill in the art based on, for example, the length and/or base composition of the DNA. One way of achieving moderately stringent conditions for filter-bound target DNA involves the use of a prewashing solution containing 5×SSC, 0.5% SDS, 1.0 mM EDTA (pH 8.0), hybridization buffer of about 6×SSC, and a hybridization temperature of about 68° C. (or other similar hybridization solutions, such as one containing about 50% formamide, with a hybridization temperature of about 42° C.), and washing conditions of about 60° C., in 0.5×SSC, 0.1% SDS. "SSC" (1×) is 0.15 M NaCl, 0.015 M Na citrate, pH 7.0. Generally, highly stringent conditions are defined as hybridization conditions as above, but with washing at approximately 68° C., 0.2×SSC, 0.1% SDS. If desired, SSPE (1×SSPE is 0.15M NaCl, 10 mM $NaH_2PO_4$, and 1.25 mM EDTA, pH 7.4) can be substituted for SSC in the hybridization and wash buffers, and the SDS can be omitted from any of the above buffers without affecting the stringency. Washes are performed for 15 minutes after hybridization is complete. Wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). The hybridization temperature for hybrid duplexes anticipated to be less than 50 base pairs in length optimally is 5 to 10° C. below the melting temperature (Tm) of the duplex, where Tm is determined according to the following equations. For hybrids less than 18 base pairs in length, Tm (° C.)=2(# of A+T bases)+4(# of #G+C bases). For hybrids above 18 base pairs in length, Tm (° C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 85%, at least 90%, at least 95%, at least 97.5%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps.

The present invention also provides genes corresponding to the nucleic acid sequences disclosed herein. "Corresponding genes" or "corresponding genomic nucleic acids" are the regions of the genome that are transcribed to produce the mRNAs from which cDNA nucleic acid sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein, for example, for designing probes or PCR primers. Such methods include the preparation of probes or primers from the disclosed sequence information for identification and/or amplification of genes in appropriate genomic libraries or other sources of genomic materials. An "isolated gene" or "an isolated genomic nucleic acid" is a genomic nucleic acid that has been separated from the adjacent genomic sequences present in the genome of the organism from which the genomic nucleic acid was isolated.

Methods for Making and Purifying Thypin Polypeptides

Methods for the expression, isolation, and purification of the polypeptides and fragments of the invention can be accomplished by any suitable technique, including but not limited to the following methods. Preferred host cells for producing recombinant Thypin polypeptides are COS-7, CV-1, 293 and CHO cells. The glycosylation profile of these Thypin polypeptides is important to their activity. Other preferred polypeptide processing methods for making Thypin polypeptides involve the use of certain processing, binding, or chaperone polypeptides.

The isolated nucleic acid of the invention may be operably linked to an expression control sequence such as that in the pDC412 or pDC314 vectors, or the pMT2 or pED expression vectors disclosed in Kaufman et al., Nucleic Acids Res. 19, 4485–4490 (1991); and Pouwels et al. *Cloning Vectors: A Laboratory Manual*, Elsevier, N.Y., (1985), in order to produce the polypeptide recombinantly. Many suitable expression control sequences are known in the art. General methods of expressing recombinant polypeptides are also known, such as those described in R. Kaufman, Methods in Enzymology 185, 537–566 (1990). As used herein "operably linked" means that the nucleic acid of the invention and an expression control sequence are situated within a construct, vector, or cell in such a way that the polypeptide encoded by the nucleic acid is expressed when appropriate molecules (such as polymerases) are present. As one embodiment of the invention, at least one expression control sequence is operably linked to the nucleic acid of the invention in a recombinant host cell or progeny thereof, the nucleic acid and/or expression control sequence having been introduced into the host cell by transformation or transfection, for example, or by any other suitable method. As another embodiment of the invention, at least one expression control sequence is integrated into the genome of a recombinant host cell such that it is operably linked to a nucleic acid sequence encoding a polypeptide of the invention. In a further embodiment of the invention, at least one expression control sequence is operably linked to a nucleic acid of the invention through the action of a trans-acting factor such as a transcription factor, either in vitro or in a recombinant host cell.

In addition, a sequence encoding a signal peptide (native or heterologous) that promotes secretion can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367, 566; the type I interleukin-1 receptor signal peptide described in U.S. Pat. No. 4,968,607; and the type II interleukin-1 receptor signal peptide described in EP 460, 846. A DNA sequence for a signal peptide (secretory leader) can be fused in frame to the nucleic acid sequence of the invention so that the DNA is initially transcribed, and the mRNA translated, into a fusion polypeptide comprising the signal peptide. A signal peptide that is functional in the intended host cells is one that promotes extracellular secretion of the polypeptide in that host cell. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, R. J., *Large Scale Mammalian Cell Culture,* 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual,* 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable strain for DHFR selection is CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective medium. Other examples of selectable markers that can be incorporated into an expression vector include cDNAs conferring resistance to antibiotics, such as G418 and hygromycin B. Cells harboring the vector can be selected on the basis of resistance to these compounds.

Alternatively, Thypin gene products can be obtained via homologous recombination, or "gene targeting," techniques. Such techniques employ the introduction of exogenous transcription control elements (such as the CMV promoter or the like) in a particular predetermined site on the genome, to induce expression of the endogenous nucleic acid sequence of interest (see, for example, U.S. Pat. No. 5,272, 071). The location of integration into a host chromosome or genome can be easily determined by one of skill in the art, given the known location and sequence of the gene. In a preferred embodiment, the present invention also contemplates the introduction of exogenous transcriptional control elements in conjunction with an amplifiable gene, to produce increased amounts of the gene product, again, without the need for isolation of the gene sequence itself from the host cell.

A number of types of cells may act as suitable host cells for expression of the polypeptide. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (*EMBO J.* 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, the polypeptide may be produced in lower eukaryotes such as yeast or in prokaryotes such as bacteria. Suitable yeast strains include *Saccharomyces cerevisiae, Schizosaccharomyces pombe, Kluyveromyces* strains, *Candida* spp., *Pichia* spp. or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional Thypin polypeptide. Such covalent attachments may be accomplished using known chemical or enzymatic methods. The polypeptide may also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the Max-Bac® kit), and such methods are well known in the art, as described in Summers and Smith, Texas Agricultural Experiment Station Bulletin No. 1555 (1987), and Luckow and Summers, *Bio/Technology* 6:47 (1988). As used herein, an insect cell that is modified to express an exogenous nucleic acid of the present invention is considered "transformed." Cell-free translation systems may also be employed to produce polypeptides using RNAs derived from nucleic acid constructs disclosed herein. A host cell that comprises an isolated nucleic acid of the invention, preferably operably linked to at least one expression control sequence, is a "recombinant host cell".

The polypeptide of the invention may be prepared by culturing transformed host cells under culture conditions suitable to support expression of the recombinant polypeptide. The resulting expressed polypeptide may then be purified from such culture (i.e., from culture medium or cell extracts) using known purification processes, such as selective precipitation with various salts, gel filtration and ion exchange chromatography. The purification of the polypeptide may also include an affinity column containing agents that will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography using an antibody that specifically binds one or more Thypin epitopes.

Alternatively, the polypeptide of the invention may also be expressed in a form that will facilitate purification. For example, it may be expressed as a fusion polypeptide, that is, it may be fused with a maltose binding polypeptide (MBP), glutathione-5-transferase (GST), thioredoxin (TRX) or polyHIS. Kits for expression and purification of such fusion polypeptides are commercially available from New England BioLab (Beverly, Mass.), Pharmacia (Piscataway, N.J.) and InVitrogen, respectively. The polypeptide can also be tagged with a non-Thypin epitope and subsequently purified by using a specific antibody directed to such epitope. One such epitope (FLAG®) is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. The polypeptide thus purified is substantially free of other mammalian polypeptides and is defined in accordance with the present invention as an "isolated polypeptide." The afore-described purification method may be used to isolate Thypin and Thypin fragments as well as antibodies that bind to Thypin polypeptides, fragments, variants, binding partners etc. The polypeptide of the invention may also be expressed as a product of transgenic animals, e.g., as a component of the milk of transgenic cows, goats, pigs, or sheep which are characterized by containing somatic or germ cells into which has been inserted a nucleic acid encoding a human Thypin polypeptide.

It is also possible to utilize an affinity column comprising a polypeptide capable of binding to Thypin polypeptides, such as a monoclonal antibody generated against Thypin or against an antigenic fragment thereof, to affinity-purify expressed Thypin polypeptides. These Thypin polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, Thypin-binding polypeptides, such as the anti-Thypin antibodies of the invention or other polypeptides that can interact with Thypin or fragments thereof, can be bound to a solid phase support such as a column chromatography matrix or a similar substrate suitable for identifying, separating, or purifying cells that express polypeptides of the invention on their surface. Adherence of Thypin-binding polypeptides of the invention to a solid phase contacting surface can be accomplished by any means, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the invention on their surface bind to the fixed Thypin-binding polypeptide and unbound cells then are washed away. This affinity-binding method is useful for purifying, screening, or separating such Thypin-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the invention first can be incubated with a biotinylated Thypin-binding polypeptide of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.,* 10D:239 (1986). Wash of unbound material and the release of the bound cells is performed using conventional methods.

The polypeptide may also be produced by known conventional chemical synthesis. The synthetically-constructed polypeptide sequences, by virtue of sharing primary, secondary or tertiary structural and/or conformational characteristics with polypeptides may possess biological properties in common therewith, including polypeptide activity. Thus, they may be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Antagonists and Agonists of Thypin Polypeptides

Any method which neutralizes Thypin polypeptides or inhibits expression of the Thypin genes (either transcription or translation) can be used to reduce the biological activities of Thypin polypeptides. In particular embodiments, antagonists inhibit the binding of at least one Thypin polypeptide to cells, thereby inhibiting biological activities induced by the binding of those Thypin polypeptides to the cells. In other embodiments, antagonists inhibit the binding of at least one Thypin polypeptide to a target protease. In yet other embodiments, antagonists can be designed to reduce the level of endogenous Thypin gene expression, e.g., using well-known antisense or ribozyme approaches to inhibit or prevent translation of Thypin mRNA transcripts; triple helix approaches to inhibit transcription of Thypin genes; or targeted homologous recombination to inactivate or "knock out" the Thypin genes or their endogenous promoters or enhancer elements. Such antisense, ribozyme, and triple helix antagonists may be designed to reduce or inhibit either unimpaired, or if appropriate, mutant Thypin gene activity.

Techniques for the production and use of such molecules are well known to those of skill in the art.

Antisense RNA and DNA molecules can act to directly block the translation of mRNA by hybridizing to targeted endogenous mRNA thereby preventing translation. This antisense approach involves designing oligonucleotides (either DNA or RNA) that are complementary to a Thypin mRNA. The antisense oligonucleotides will bind to the complementary target gene mRNA transcripts and prevent translation. Absolute complementarity, although preferred, is not required. An antisense molecule "complementary" to Thypin nucleic acid, as referred to herein, means a sequence having sufficient complementarity to be able to hybridize with the target nucleic acid, forming a stable duplex (or triplex, as appropriate). In the case of double-stranded antisense nucleic acids, a single strand of the duplex DNA may thus be tested, or triplex formation may be assayed. The ability to hybridize will depend on both the degree of complementarity and the length of the antisense nucleic acid. Preferred oligonucleotides are those that are complementary to the 5' end of the message, e.g., the 5' untranslated sequence up to and including the AUG initiation codon. However, oligonucleotides complementary to the 5'- or 3'-non-translated, non-coding regions of the Thypin gene transcript, or to the coding regions, may be used.

Antisense oligonucleotides complementary to the 5' untranslated region of the mRNA preferably include the complement of the AUG start codon. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides. The oligonucleotides can be DNA or RNA or chimeric mixtures or derivatives or modified versions thereof, single-stranded or double-stranded. Chimeric oligonucleotides, oligonucleosides, or mixed oligonucleotides/oligonucleosides of the invention can be of several different types. These include a first type wherein the "gap" segment of nucleotides is positioned between 5' and 3' "wing" segments of linked nucleosides and a second "open end" type wherein the "gap" segment is located at either the 3' or the 5' terminus of the oligomeric compound (see, e.g., U.S. Pat. No. 5,985,664). Oligonucleotides of the first type are also known in the art as "gapmers" or gapped oligonucleotides. Oligonucleotides of the second type are also known in the art as "hemimers" or "wingmers". The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc Natl Acad Sci U.S.A. 86: 6553–6556; Lemaitre et al., 1987, Proc Natl Acad Sci 84: 648–652; PCT Publication No. WO88/09810), or hybridization-triggered cleavage agents or intercalating agents. (See, e.g., Zon, 1988, Pharm. Res. 5: 539–549). The antisense molecules should be delivered to cells which express the Thypin transcript in vivo.

A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Thypin gene transcripts and thereby prevent translation of the Thypin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave Thypin mRNA transcripts can also be used to prevent translation of Thypin mRNA and expression of Thypin polypeptides. (See, e.g., PCT International Publication WO90/11364, published Oct. 4, 1990; U.S. Pat. No. 5,824,519). The ribozymes that can be used in the present invention include hammerhead ribozymes (Haseloff and Gerlach, 1988, Nature, 334:585–591), RNA endoribonucleases (hereinafter "Cech-type ribozymes") such as the one which occurs naturally in *Tetrahymena thermophila* (known as the IVS, or L-19 IVS RNA) and which has been extensively described (see, for example, WO 88/04300; Been and Cech, *Cell,* 47:207–216 (1986)). As in the antisense approach, the ribozymes can be composed of modified oligonucleotides (e.g. for improved stability, targeting, etc.) and should be delivered to cells which express the Thypin polypeptide in vivo. A preferred method of delivery involves using a DNA construct encoding the ribozyme under the control of a strong constitutive pol III or pol II promoter, so that transfected cells will produce sufficient quantities of the ribozyme to destroy endogenous Thypin messages and inhibit translation. Because ribozymes, unlike antisense molecules, are catalytic, a lower intracellular concentration is required for efficacy.

Alternatively, endogenous Thypin gene expression can be reduced by using deoxyribonucleotide sequences complementary to the regulatory region of the target gene (i.e., the target gene promoter and/or enhancers) to form triple helical structures that prevent transcription of the target Thypin gene. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Anti-sense RNA and DNA, ribozyme, and triple helix molecules of the invention may be prepared by any method known in the art for the synthesis of DNA and RNA molecules, including, for example, solid phase phosphoramidite chemical synthesis. Oligonucleotides can be synthesized by standard methods known in the art, e.g. by use of an automated DNA synthesizer (such as are commercially available from Biosearch, Applied Biosystems, etc.). Phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448–7451). Alternatively, RNA molecules may be generated by in vitro or in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constituitively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra), or in model organisms such as Caenorhabditis elegans where the "RNA interference" ("RNAi") technique (Grishok A, Tabara H, and Mello C C, 2000, Genetic requirements for inheritance of RNAi in C. elegans, Science 287 (5462): 2494–2497), or the introduction of transgenes (Demburg A F, Zalevsky J, Colaiacovo M P, and Villeneuve A M, 2000, Transgene-mediated cosuppression in the C. elegans germ line, Genes Dev. 14 (13): 1578–1583) are used to inhibit the expression of specific target genes. However this approach can be adapted for use in humans provided the recombinant DNA constructs are directly administered or targeted to the required site in vivo using appropriate vectors such as viral vectors.

Organisms that have enhanced, reduced, or modified expression of the gene(s) corresponding to the nucleic acid sequences disclosed herein are provided. The desired change in gene expression can be achieved through the use of antisense nucleic acids or ribozymes that bind and/or cleave the mRNA transcribed from the gene (Albert and Morris, 1994, Trends Pharmacol. Sci. 15(7): 250–254; Lavarosky et al., 1997, Biochem. Mol. Med. 62(1): 11–22; and Hampel, 1998, Prog. Nucleic Acid Res. Mol. Biol. 58: 1–39). Transgenic animals that have multiple copies of the gene(s) corresponding to the nucleic acid sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1). In addition, organisms are provided in which the gene(s) corresponding to the nucleic acid sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9): 629–633; Zwaal et al., 1993, Proc. Natl. Acad. Sci. USA 90(16): 7431–7435; Clark et al., 1994, Proc. Natl. Acad. Sci. USA 91(2): 719–722), or through homologous recombination, preferably detected by positive/negative genetic selection strategies (Mansour et al., 1988, Nature 336: 348–352; U.S. Pat. Nos. 5,464,764; 5,487,992; 5,627,059; 5,631,153; 5,614,396; 5,616,491; and 5,679,523). These organisms with altered gene expression are preferably eukaryotes and more preferably are mammals. Such organisms are useful for the development of non-human models for the study of disorders involving the corresponding gene(s), and for the development of assay systems for the identification of molecules that interact with the polypeptide product(s) of the corresponding gene(s).

Also provided are Thypin polypeptide variants with partner binding sites that have been altered in conformation so that (1) the Thypin variant will still bind to its partner(s), but a specified small molecule will fit into the altered binding site and block that interaction, or (2) the Thypin variant will no longer bind to its partner(s) unless a specified small molecule is present (see for example Bishop et al., 2000, Nature 407: 395–401). Nucleic acids encoding such altered Thypin polypeptides can be introduced into organisms according to methods described herein, and may replace the endogenous nucleic acid sequences encoding the corresponding Thypin polypeptide. Such methods allow for the interaction of a particular Thypin polypeptide with its binding partners to be regulated by administration of a small molecule compound to an organism, either systemically or in a localized manner.

The Thypin polypeptides themselves can also be employed in inhibiting a biological activity of Thypin in in vitro or in vivo procedures. Encompassed within the invention are Thypin polypeptides that act as "dominant negative" inhibitors of native Thypin polypeptide function when expressed as fragments or as components of fusion polypeptides. For example, a purified polypeptide comprising the Thypin RSL domain (amino acids 374 to 395 of SEQ ID NO:2) can be used to inhibit binding of endogenous Thypin polypeptides to endogenous binding partners. Such use effectively would block Thypin polypeptide interactions and inhibit Thypin polypeptide activities.

In a preferred embodiment, antibodies that bind specifically with the Thypin polypeptide shown in SEQ ID NO:2 are used to antagonize the ability of Thypin to inhibit its target protease(s). For example, antibodies that specifically recognize one or more epitopes of Thypin polypeptides, or epitopes of conserved variants of Thypin polypeptides, or peptide fragments of the Thypin polypeptide can be used in the invention to inhibit Thypin polypeptide activity. Such antibodies include but are not limited to polyclonal antibodies, monoclonal antibodies (mABs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be administered in therapeutic doses to treat diseases characterized by overexpression or aberrant expression of Thypin. The ability of a Thypin-specific antibody to antagonize Thypin activity can be determined, for example, in assays that measure the protease-inhibitory activity of Thypin in the presence and absence of the antibody.

Purified and modified Thypin polypeptides of the present invention can be administered to modulate interactions between Thypin polypeptides and Thypin binding partners that are not membrane-bound, such as for example, to modulate interactions of Thypin and target proteases that are present in the extracellular matrix, serum, or in the cytoplasm of cells in which Thypin is expressed. Modulating such interactions can provide a means for the modification of Thypin-influenced bioactivity.

In an alternative aspect, the invention further encompasses the use of agonists of Thypin polypeptide activity to treat or ameliorate the symptoms of a disease for which increased Thypin polypeptide activity is beneficial. In a preferred aspect, the invention entails using compositions comprising of a Thypin nucleic acid or a Thypin polypeptide to cells in vitro, to cells ex vivo, to cells in vivo, and/or to a multicellular organism such as a vertebrate or mammal. Preferred therapeutic forms of Thypin are soluble forms, as described above. In still another aspect of the invention, the invention involves methods comprising administering a therapeutically effective amount of a composition containing Thypin-encoding nucleic acid for expression of a Thypin polypeptide in a host organism for treatment of disease, or of administering a therapeutically effective amount of purified recombinant Thypin together with a pharmaceutically acceptable carrier. Such methods are useful for treatment of a pathological condition associated with decreased endogenous activity of a Thypin polypeptide. Furthermore, the invention encompasses the administration to cells and/or organisms of compounds found to increase the endogenous activity of Thypin polypeptides.

One example of compounds that increase Thypin polypeptide activity are agonistic antibodies, preferably monoclonal antibodies, that increase Thypin activity when the antibody is bound to Thypin. Alternatively, such an antibody could increase Thypin polypeptide activity for example by preventing the binding to Thypin of a native inhibitor of Thypin polypeptide activity. The ability of a Thypin-specific antibody to antagonize or agonize Thypin activity can be determined in assays that measure the protease-inhibitory activity of Thypin in the presence and absence of the antibody.

Antibodies to Thypin Polypeptides

Antibodies that are specifically immunoreactive with the polypeptides of the invention are provided herein. Such antibodies bind to Thypin polypeptides via the antigen-binding sites of the antibody (as opposed to non-specific binding). In the present invention, specifically binding antibodies are those that will specifically recognize and bind Thypin polypeptides or subportions thereof, homologues, and variants, or Thypin fusion proteins, but that will not bind other protein molecules. In one preferred embodiment, the antibodies are specific for the polypeptides of the present invention, such as the polypeptide whose amino acid sequence is shown in SEQ ID NO:2, and do not cross-react with other proteins. The Thypin polypeptides, fragments, variants and Thypin fusion polypeptides as set forth herein can be employed as "immunogens" in producing antibodies immunoreactive therewith.

The polypeptides, fragments, variants, fusion polypeptides, and so on described herein contain antigenic determinants or epitopes that elicit the formation of antibodies that bind specifically with Thypin. Thypin-specific antibodies do not bind with other known serpins, that is, these antibodies do not bind via their hypervariable region binding site with ov-serpins such as SCCA-1, SCCA-2, hurpin or maspin. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (Janeway and Travers, *Immuno Biology* 3:9 (Garland Publishing Inc., 2nd ed. 1996)). Because folded polypeptides have complex surfaces, the number of epitopes available is quite numerous; however, due to the conformation of the polypeptide and steric hindrances, the number of antibodies that actually bind to the epitopes is less than the number of available epitopes (Janeway and Travers, *Immuno Biology* 2:14 (Garland Publishing Inc., 2nd ed. 1996)). Epitopes can be identified by any of the methods known in the art. Thus, one aspect of the present invention relates to the antigenic epitopes of Thypin. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

The Thypin polypeptide shown in SEQ ID NO:2 or subportions thereof provide suitable proteins for raising Thypin-specific antibodies. For this purpose, contiguous segments comprising at least 15 amino acids of SEQ ID NO:2 are used. Particular subregions of Thypin useful for raising Thypin-specific antibodies include amino acids 61–107, 108–373 and 374–395 of SEQ ID NO:2.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kozbor et al., 1984, *J. Immunol.* 133:3001–3005; Cole et al., 1983, *Proc. Natl. Acad. Sci. USA* 80:2026–2030); and the EBV-hybridoma technique (Cole et al., 1985, Monoclonal Antibodies And Cancer Therapy, Alan R. Liss, Inc., pp. 77–96). Hybridoma cell lines that produce monoclonal antibodies specific for the polypeptides of the invention are also contemplated herein. Such hybridomas can be produced and identified by conventional techniques. The hybridoma producing the mAb of this invention may be cultivated in vitro or in vivo. Production of high titers of mAbs in vivo makes this the presently preferred method of production. One method for producing such a hybridoma cell line comprises immunizing an animal with a Thypin polypeptide large enough to include at least one Thypin-specific epitope; harvesting spleen cells from the immunized animal; fusing said spleen cells to a myeloma cell line, thereby generating hybridoma cells; and identifying a hybridoma cell line that produces a monoclonal antibody that binds the polypeptide. In a preferred embodiment, the antibody will bind native Thypin.

In another preferred embodiment, the antibody will specifically bind an epitope unique to the complex formed between Thypin and its protease target. Antibodies specific for such complexes are raised by using as antigen the complex formed between Thypin and its protease target. Such antibodies are useful in assays to detect the presence of such complexes in tissues, cells, serum or extracellular matrix.

For the production of antibodies, various host animals may be immunized by injection with one or more of the following: a Thypin polypeptide, a fragment of a Thypin polypeptide, a functional equivalent of a Thypin polypeptide, or a mutant form of a Thypin polypeptide. Such host animals may include but are not limited to rabbits, guinea pigs, mice and rats. Various adjuvants may be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD and any subclass thereof.

In addition, techniques developed for the production of "chimeric antibodies" (Takeda et al., 1985, *Nature,* 314: 452–454; Morrison et al., 1984, *Proc Natl Acad Sci USA* 81:6851–6855; Boulianne et al., 1984, *Nature* 312:643646; Neuberger et al., 1985, Nature 314:268–270) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the present invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) as well as a constant region derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Useful techniques for humanizing antibodies are also discussed in U.S. Pat. No. 6,054,297. Procedures to generate antibodies transgenically can be found in GB 2,272,440, U.S. Pat. Nos. 5,569,825 and 5,545,806, and related patents. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.). In another preferred embodiment, fully human antibodies for use in humans are produced by screening a phage display library of human antibody variable domains (Vaughan et al., 1998, Nat Biotechnol. 16(6): 535–539; and U.S. Pat. No. 5,969,108).

Antigen-binding antibody fragments that recognize specific epitopes may be generated by known techniques. For example, such fragments include but are not limited to: the F(ab')2 fragments that can be produced by pepsin digestion of the antibody molecule and the Fab fragments that can be generated by reducing the disulfide bridges of the (ab')2 fragments. Alternatively, Fab expression libraries may be constructed (Huse et al., 1989, *Science,* 246:1275–1281) to allow rapid and easy identification of monoclonal Fab fragments with the desired specificity. Techniques described for the production of single chain antibodies (U.S. Pat. No. 4,946,778; Bird, 1988, *Science* 242:423–426; Huston et al., 1988, Proc. Natl. Acad. Sci. USA 85:5879–5883; and Ward et al., 1989, Nature 334:544–546) can also be adapted to produce single chain antibodies against Thypin gene products. Single chain antibodies are formed by linking the heavy and light chain fragments of the Fc region via an amino acid bridge, resulting in a single chain polypeptide. Such single chain antibodies may also be useful intracellularly (i.e., as 'intrabodies), for example as described by Marasco et al. (*J. Immunol. Methods* 231:223–238, 1999) for genetic therapy in HIV infection. In addition, antibodies to the Thypin polypeptide can, in turn, be utilized to generate anti-idiotype antibodies that "mimic" the Thypin polypeptide and that may bind to the Thypin polypeptide using techniques well known to those skilled in the art. (See, e.g., Greenspan & Bona, 1993, *FASEB J* 7(5):437–444; and Nissinoff, 1991, *J. Immunol.* 147(8):2429–2438).

Antibodies that are immunoreactive with the polypeptides of the invention include bispecific antibodies (i.e., antibodies that are immunoreactive with the polypeptides of the invention via a first antigen binding domain, and also immunoreactive with a different polypeptide via a second antigen binding domain). A variety of bispecific antibodies have been prepared, and found useful both in vitro and in vivo (see, for example, U.S. Pat. No. 5,807,706; and Cao and Suresh, 1998, Bioconjugate Chem 9: 635–644). Numerous methods of preparing bispecific antibodies are known in the art, including the use of hybrid-hybridomas such as quadromas, which are formed by fusing two differed hybridomas, and triomas, which are formed by fusing a hybridoma with a lymphocyte (Milstein and Cuello, 1983, *Nature* 305: 537–540; U.S. Pat. Nos. 4,474,893; and 6,106,833). U.S. Pat. No. 6,060,285 discloses a process for the production of bispecific antibodies in which at least the genes for the light chain and the variable portion of the heavy chain of an antibody having a first specificity are transfected into a hybridoma cell secreting an antibody having a second specificity. Chemical coupling of antibody fragments has also been used to prepare antigen-binding molecules having specificity for two different antigens (Brennan et al., 1985, *Science* 229: 81–83; Glennie et al., *J. Immunol.,* 1987, 139:2367–2375; and U.S. Pat. No. 6,010,902). Bispecific antibodies can also be produced via recombinant means, for example, by using. the leucine zipper moieties from the Fos and Jun proteins (which preferentially form heterodimers) as described by Kostelny et al. (*J. Immunol.* 148:1547–4553; 1992). U.S. Pat. No. 5,582,996 discloses the use of complementary interactive domains (such as leucine zipper moieties or other lock and key interactive domain structures) to facilitate heterodimer formation in the production of bispecific antibodies. Tetravalent, bispecific molecules can be prepared by fusion of DNA encoding the heavy chain of an F(ab')2 fragment of an antibody with either DNA encoding the heavy chain of a second F(ab')2 molecule (in which the CH1 domain is replaced by a CH3 domain), or with DNA encoding a single chain FV fragment of an antibody, as described in U.S. Pat. No. 5,959,083. Expression of the resultant fusion genes in mammalian cells, together with the genes for the corresponding light chains, yields tetravalent bispecific molecules having specificity for selected antigens. Bispecific antibodies can also be produced as described in U.S. Pat. No. 5,807,706. Generally, the method involves introducing a protuberance (constructed by replacing small amino acid side chains with larger side chains) at the interface of a first polypeptide and a corresponding cavity (prepared by replacing large amino acid side chains with smaller ones) in the interface of a second polypeptide. Moreover, single-chain variable fragments (sFvs) have been prepared by covalently joining two variable domains; the resulting antibody fragments can form dimers or trimers, depending on the length of a flexible linker between the two variable domains (Kortt et al., 1997, *Protein Engineering* 10:423–433).

Screening procedures by which such antibodies can be identified are well known, and can involve immunoaffinity chromatography, for example. Antibodies can be screened for agonistic (i.e., ligand-mimicking) properties. Agonistic antibodies can be used to induce Thypin-mediated stimulatory pathways or intercellular communication or other Thypin-mediated physiological phenomena.

Those antibodies that can block binding of the Thypin polypeptides of the invention to binding partners for Thypin can be used to inhibit Thypin-mediated phenomena that results from such binding. Such blocking antibodies can be identified using any suitable assay procedure, such as by testing antibodies for the ability to inhibit binding of Thypin binding to trypsin-like proteases. Alternatively, blocking antibodies can be identified in assays for the ability to inhibit a biological effect that results from binding of Thypin to its target. Such an antibody can be employed in an in vitro procedure, or administered in vivo to inhibit a biological activity mediated by Thypin. Disorders caused or exacerbated (directly or indirectly) by the interaction of Thypin with a Thypin binding partner thus can be treated. A therapeutic method involves in vivo administration of a blocking antibody to a mammal in an amount effective in inhibiting Thypin-mediated biological activity. Monoclonal antibodies are generally preferred for use in such therapeutic methods. In one embodiment, an antigen-binding antibody fragment is employed. Compositions comprising an antibody that is directed against Thypin, and a physiologically acceptable diluent, excipient, or carrier, are provided herein. Suitable components of such compositions are as described below for compositions containing Thypin polypeptides.

Also provided herein are conjugates comprising a detectable (e.g., diagnostic) or therapeutic agent, attached to the antibody. Examples of such agents are presented above. The conjugates find use in in vitro or in vivo procedures. The antibodies of the invention can also be used in assays to detect the presence of Thypin polypeptides or fragments thereof, either in vitro or in vivo. The antibodies also can be employed in purifying polypeptides or fragments of the invention by immunoaffinity chromatography.

Rational Design of Compounds that Interact with Thypin Polypeptides

The goal of rational drug design is to produce structural analogs of biologically active polypeptides of interest or of small molecules with which they interact, e.g., inhibitors, agonists, antagonists, etc. This approach can be used to fashion drugs which are more active or stable forms of the polypeptide or which enhance or interfere with the function of a polypeptide in vivo (Hodgson J (1991) Biotechnology 9:19–21). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the molecule. Less often, useful information regarding the structure of a polypeptide may be gained by modeling based on the structure of homologous polypeptides. In both cases, relevant structural information is used to design analogous serpin-like molecules, to identify efficient inhibitors, or to identify small molecules that may bind serpins. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746). The use of Thypin polypeptide structural information in molecular modeling software systems to assist in agonist or inhibitor design and agonist-Thypin or inhibitor-Thypin polypeptide interaction is also encompassed by the invention. A particular method of the invention comprises analyzing the three dimensional structure of Thypin polypeptides for likely binding sites of substrates, synthesizing a new molecule that incorporates a predictive reactive site, and assaying the new molecule as described further herein.

It is also possible to isolate a target-specific antibody, selected by functional assay, as described further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original antigen. The anti-id could then be used to identify and isolate peptides from banks of chemically or biologically produced peptides. The isolated peptides would then act as the pharmacore.

Assays of Thypin Polypeptide Activities

The purified Thypin polypeptides of the invention (including polypeptides, polypeptides, fragments, variants, oligomers, and other forms) are useful in a variety of assays. For example, the Thypin molecules of the present invention can be used to identify binding partners of Thypin polypeptides, which can also be used to modulate various physiological phenomena. Alternatively, they can be used to identify non-binding-partner molecules or substances that modulate development, tissue remodeling and so on.

Assays to Identify Binding Partners. Thypin polypeptides and fragments thereof can be used to identify binding partners. For example, they can be tested for the ability to bind a candidate binding partner in any suitable assay, such as a conventional binding assay. To illustrate, the Thypin polypeptide can be labeled with a detectable reagent (e.g., a radionuclide, chromophore, enzyme that catalyzes a colorimetric or fluorometric reaction, and the like). The labeled polypeptide is contacted with candidate serine proteases that are suspected of having the capacity to interact with Thypin. If specific binding occurs, the labelled Thypin is expected to form a heat-stable complex with the protease. These complexes can be detected by any convenient means, which may employ gel electrophoresis or column chromatography.

Compounds that can be assayed for binding to Thypin polypeptides include but are not limited to small organic molecules, such as those that are commercially available—often as part of large combinatorial chemistry compound ‘libraries’—from companies such as Sigma-Aldrich (St. Louis, Mo.), Arqule (Woburn, Mass.), Enzymed (Iowa City, Iowa), Maybridge Chemical Co.(Trevillett, Cornwall, UK), MDS Panlabs (Bothell, Wash.), Pharmacopeia (Princeton, N.J.), and Trega (San Diego, Calif.). Preferred small organic molecules for screening using these assyas are usually less than 10 kDa molecular weight and may possess a number of physicochemical and pharmacological properties which enhance cell penetration, resist degradation, and/or prolong their physiological half-lives (Gibbs, J., 1994, Pharmaceutical Research in Molecular Oncology, *Cell* 79(2): 193–198). Compounds including natural products, inorganic chemicals, and biologically active materials such as proteins and toxins can also be assayed using these methods for the ability to bind to Thypin polypeptides.

Yeast Two-Hybrid or "Interaction Trap" Assays. Where the Thypin polypeptide binds or potentially binds to another polypeptide, the nucleic acid encoding the Thypin polypeptide can also be used in interaction trap assays (such as, for example, that described in Gyuris et al., Cell 75:791–803 (1993)) to identify nucleic acids encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate binding partner. Competitive binding assays can be performed by conventional methodology. Reagents that can be employed in competitive binding assays include radiolabeled Thypin and intact cells expressing Thypin (endogenous or recombinant). For example, a radiolabeled soluble Thypin fragment can be used to compete with native Thypin for binding to a target protease.

Cell Proliferation, Cell Death, Cell Differentiation, and Cell Adhesion Assays

A polypeptide of the present invention may exhibit cell proliferation (either inducing or inhibiting), or cell differentiation (either inducing or inhibiting) activity, or may induce production of cytokines in certain cell populations. Many polypeptide factors discovered to date have exhibited such activity in one or more factor-dependent cell proliferation assays, and hence the assays serve as a convenient confirmation of cell stimulatory activity. The activity of a polypeptide of the present invention is evidenced by any one of a number of routine factor-dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a Thypin polypeptide of the invention may, among other means, be measured by the following methods:

Assays for T-cell or thymocyte proliferation include without limitation those described in: *Current Protocols in Immunology*, Coligan et al. eds, Greene Publishing Associates and Wiley-Interscience (pp. 3.1–3.19: In vitro assays for mouse lymphocyte function; Chapter 7: Immunologic studies in humans); Takai et al., J. Immunol. 137: 3494–3500, 1986; Bertagnolli et al., J. Immunol. 145: 1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Kruisbeek and Shevach, 1994, Polyclonal T cell stimulation, in *Current Protocols in Immunology*, Coligan et al. eds. Vol 1 pp. 3.12.1–3.12.14, John Wiley and Sons, Toronto; and Schreiber, 1994, Measurement of mouse and human interferon gamma in *Current Protocols in Immunology*, Coligan et al. eds. Vol 1 pp. 6.8.1–6.8.8, John Wiley and Sons, Toronto.

Assays for proliferation and differentiation of hematopoietic and lymphopoietic cells include, without limitation, those described in: Bottomly et al., 1991, Measurement of human and murine interleukin 2 and interleukin 4, in *Current Protocols in Immunology*, Coligan et al. eds. Vol 1 pp. 6.3.1–6.3.12, John Wiley and Sons, Toronto; deVries et al., J Exp Med 173: 1205–1211, 1991; Moreau et al., Nature 336:690–692, 1988; Greenberger et al., Proc Natl Acad. Sci. USA 80: 2931–2938, 1983; Nordan, 1991, Measurement of mouse and human interleukin 6, in *Current Protocols in Immunology* Coligan et al. eds. Vol 1 pp. 6.6.1–6.6.5, John Wiley and Sons, Toronto; Smith et al., Proc Natl Acad Sci USA 83: 1857–1861, 1986; Bennett et al., 1991, Measurement of human interleukin 11, in *Current Protocols in Immunology* Coligan et al. eds. Vol 1 pp. 6.15.1 John Wiley and Sons, Toronto; Ciarletta et al., 1991, Measurement of mouse and human Interleukin 9, in *Current Protocols in Immunology* Coligan et al. eds. Vol 1 pp. 6.13.1, John Wiley and Sons, Toronto.

Assays for T-cell clone responses to antigens (which will identify, among others, polypeptides that affect APC-T cell interactions as well as direct T-cell effects by measuring proliferation and cytokine production) include, without limitation, those described in: *Current Protocols in Immunology*, Coligan et al. eds, Greene Publishing Associates and Wiley-Interscience (Chapter 3: In vitro assays for mouse lymphocyte function; Chapter 6: Cytokines and their cellular receptors; Chapter 7: Immunologic studies in humans); Weinberger et al., Proc Natl Acad Sci USA 77: 6091–6095, 1980; Weinberger et al., Eur. J. Immun. 11:405–411, 1981; Takai et al., J. Immunol. 137:3494–3500, 1986; Takai et al., J. Immunol. 140:508–512, 1988

Assays for thymocyte or splenocyte cytotoxicity include, without limitation, those described in: *Current Protocols in Immunology*, Coligan et al. eds, Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, polypeptides that modulate T-cell dependent antibody responses and that affect Th1/Th2 profiles) include, without limitation, those described in: Maliszewski, J Immunol 144: 3028–3033, 1990; and Mond and Brunswick, 1994, Assays for B cell function: in vitro antibody production, in *Current Protocols in Immunology* Coligan et al. eds. Vol 1 pp. 3.8.1–3.8.16, John Wiley and Sons, Toronto.

Mixed lymphocyte reaction (MLR) assays (which will identify, among others, polypeptides that generate predominantly Th1 and CTL responses) include, without limitation, those described in: *Current Protocols in Immunology*, Coligan et al. eds, Greene Publishing Associates and Wiley- Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, polypeptides expressed by dendritic cells that activate naive T-cells) include, without limitation, those described in: Guery et al., J. Immunol 134:536–544, 1995; Inaba et al., J Exp Med 173:549–559, 1991; Macatonia et al., J Immunol 154:5071–5079, 1995; Porgador et al., J Exp Med 182:255–260, 1995; Nair et al., J Virology 67:4062–4069, 1993; Huang et al., Science 264:961–965, 1994; Macatonia et al., J Exp Med 169:1255–1264, 1989; Bhardwaj et al., J Clin Invest 94:797–807, 1994; and Inaba et al., J Exp Med 172:631–640, 1990.

Assays for lymphocyte survival/apoptosis (which will identify, among others, polypeptides that prevent apoptosis after superantigen induction and polypeptides that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, J Immunol 145:4037–4045, 1990; Zamai et al., Cytometry 14:891–897, 1993; Gorczyca et al., International Journal of Oncology 1:639–648, 1992.

Assays for polypeptides that influence early steps of T-cell commitment and development include, without limitation, those described in: Antica et al., Blood 84:111–117, 1994; Fine et al., Cell Immunol 155:111–122, 1994; Galy et al., Blood 85:2770–2778, 1995; Toki et al., Proc Natl Acad. Sci. USA 88:7548–7551, 1991

Assays for embryonic stem cell differentiation (which will identify, among others, polypeptides that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, polypeptides that regulate lympho-hematopoiesis) include, without limitation, those described in: Methylcellulose colony forming assays, Freshney, 1994, In *Culture of Hematopoietic Cells*, Freshney et al. eds. pp. 265–268, Wiley-Liss, Inc., New York, N.Y.; Hirayama et al., Proc. Natl. Acad. Sci. USA 89:5907–5911, 1992; Primitive hematopoietic colony forming cells with high proliferative potential, McNiece and Briddell, 1994, In *Culture of Hematopoietic Cells*, Freshney et al. eds. pp. 23–39, Wiley-Liss, Inc., New York, N.Y.; Neben et al., Experimental Hematology 22:353–359, 1994; Ploemacher, 1994, Cobblestone area forming cell assay, In *Culture of Hematopoietic Cells*, Freshney et al. eds. pp. 1–21, Wiley-Liss, Inc., New York, N.Y.; Spooncer et al., 1994, Long term bone marrow cultures in the presence of stromal cells, In *Culture of Hematopoietic Cells*, Freshney et al. eds. pp. 163–179, Wiley-Liss, Inc., New York, N.Y.; Sutherland, 1994, Long term culture initiating cell assay, In *Culture of Hematopoietic Cells*, Freshney et al. eds. Vol pp. 139–162, Wiley-Liss, Inc., New York, N.Y.

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium). Assays for wound healing activity include, without limitation, those described in: Winter, Epidermal Wound Healing, pps. 71–112 (Maibach and Rovee, eds.), Year Book Medical Publishers, Inc., Chicago, as modified by Eaglstein and Mertz, J. Invest. Dermatol 71:382–84 (1978).

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Assays for cell movement and adhesion include, without limitation, those described in: *Current Protocols in Immunology* Coligan et al. eds, Greene Publishing Associates and Wiley-Interscience (Chapter 6.12, Measurement of alpha and beta chemokines 6.12.1–6.12.28); Taub et al. J. Clin. Invest. 95:1370–1376, 1995; Lind et al. APMIS 103:140–146, 1995; Muller et al Eur. J. Immunol. 25: 1744–1748; Gruber et al. J. Immunol. 152:5860–5867, 1994; Johnston et al. J. Immunol. 153: 1762–1768, 1994.

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Assays for receptor-ligand activity include without limitation those described in: *Current Protocols in Immunology* Coligan et al. eds, Greene Publishing Associates and Wiley-Interscience (Chapter 7.28, Measurement of cellular adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63:1033–1038, 1990.

Diagnostic and Other Uses of Thypin Polypeptides and Nucleic Acids

The nucleic acids encoding the Thypin polypeptides provided by the present invention can be used for numerous diagnostic or other useful purposes. The nucleic acids of the invention can be used to express recombinant Thypin polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosome 18 or to map the position of an unknown genes; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for use in gene therapy.

Uses of Thypin polypeptides and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of Thypin-specific antibodies. Any or all nucleic acids suitable for these uses are capable of being developed into reagent grade materials or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987

Probes and Primers. Among the uses of the disclosed Thypin nucleic acids, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human Thypin homologues.

Chromosome Mapping. The nucleic acids encoding Thypin polypeptides, and the disclosed fragments and combinations of these nucleic acids, can be used by those skilled in the art as a chromosome marker for human 18q21.3. In addition, nucleic acids of the invention or a fragment thereof can be used as a positional marker to map other genes of unknown location. Useful techniques include, but are not limited to, using the Thypin nucleic acid sequence or portions thereof, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For radiation hybridization, PCR is first performed using the Whitehead Institute/MIT Center for Genome Research Gen ebridge4 panel of 93 radiation hybrids. For this method, PCR primers are used that lie within a putative exon of the gene of interest and that amplify a product from human genomic DNA, but that do not amplify hamster genomic DNA. The results of the PCRs are converted into a data vector that is submitted to the Whitehead/MIT Radiation Mapping site on the world-wide web at seq.wi.mit.edu. The data is scored and the chromosomal assignment and placement relative to known Sequence Tag Site (STS) markers on the radiation hybrid map is provided. Additional information about radiation hybrid mapping also can be accessed at the Whitehead/MIT website at genome.wi.mit.edu.

Diagnostics and Gene Therapy. The nucleic acids encoding Thypin polypeptides, and the disclosed fragments and combinations of these nucleic acids can be used by one skilled in the art using well-known techniques to analyze abnormalities associated with the Thypin gene or variants thereof. By this means, one can distinguish conditions in which this marker is rearranged or deleted and can use this information for diagnosing certain medical disorders. Thypin DNA furthermore can be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with a normal Thypin gene using gene therapy techniques known in the art. Defective genes can be detected in in vitro diagnostic assays, and by comparison of a native nucleotide sequence disclosed herein with that of a gene derived from a person suspected of harboring a defect in a Thypin gene.

Methods of Screening for Binding Partners. The Thypin polypeptides and fragments thereof can be used as reagents in methods to screen for or identify Thypin binding partners, such as target proteases that are inhibited by Thypin. For example, purified recombinant Thypin polypeptides can be attached to a solid support material and used as a reagent to trap its protease binding partner(s) in a manner similar to affinity chromatography. In particular embodiments, a polypeptide is attached to a solid support by conventional procedures. As one example, chromatography columns are available that contain functional groups that will react with functional groups on amino acid side chains of polypeptides (Pharmacia Biotech, Inc., Piscataway, N.J.). In an alternative, a Thypin/Fc polypeptide (as discussed above) is attached to protein A- or protein G-containing chromatography columns through interaction with the Fc moiety.

The Thypin polypeptides also find use in identifying cells that express a Thypin binding partner on the cell surface. Purified Thypin polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, Thypin polypeptides can be conjugated to a detectable moiety, then incubated with cells to be tested for binding partner expression. After incubation, unbound labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.,* 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them. Alternatively, these same assays can be used to detect Thypin binding partners in cell extracts.

Measuring Biological Activity. Thypin polypeptides also find use in measuring the biological activity of Thypin-binding polypeptides in terms of their binding affinity. The polypeptides thus can be employed by those conducting "quality assurance" studies, e.g., to monitor shelf life and stability of polypeptide under different conditions. For example, the polypeptides can be employed in a binding affinity study to measure the biological activity of a binding partner polypeptide that has been stored at different temperatures, or produced in different cell types. Thypin polypeptides also can be used to determine whether biological activity is retained after modification of a binding partner polypeptide (e.g., chemical modification, truncation, mutation, etc.). The binding affinity of the modified polypeptide is compared to that of an unmodified binding polypeptide to detect any adverse impact of the modifications on biological activity of the binding polypeptide. The biological activity of a binding polypeptide thus can be ascertained before it is used in a research study, for example.

Carriers and Delivery Agents. The polypeptides also find use as carriers for delivering agents attached thereto to cells bearing identified binding partners. The polypeptides thus can be used to deliver diagnostic or therapeutic agents to such cells (or to other cell types found to express binding partners on the cell surface) in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

Treating Diseases with Thypin Polypeptides and Antagonists Thereof

As shown in Example 6, Thypin mRNA is expressed at relatively high levels in skin. Example 6 shows further that when lung epithelial cells are exposed to a combination of IL-4 and IL-13 prior to RNA analysis, Thypin expression is selectively induced. Certain diseases, including allergies and other lung diseases, are associated with elevated levels of IL-4, IL-13 and other cytokines, and are associated also with elevated levels of various proteases that cause tissue destruction.

Accordingly, one aspect of the invention provides physiologically acceptable compositions containing Thypin for reducing protease levels in patients having a lung disorder. These compositions may be used alone or in conjunction with other medicines or treatments being used to treat the same disorder, and may be administered by injection or aerosol delivery directly to the lungs. Lung disorders that may be treated by administering Thypin include asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, and ARDS. Other pulmonary disorders that may be treated by administering Thypin include chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; sarcoidosis, including pulmonary sarcoidosis; and allergies, including allergic rhinitis, contact dermatitis, atopic dermatitis, and asthma.

Administration of compositions containing Thypin also may be useful for reducing protease levels in patients suffering from various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid. For treating skin disorders, the Thypin composition may be administered systemically by injection, via aerosol, or topically by local injection, or may be applied directly to the affected area in a lotion, ointment, cream, or gel.

Further, the Thypin polypeptides, fragments, variants, antagonists, agonists, antibodies, and binding partners of the invention are potentially useful for preventing, treating and/or diagnosing one or more medical conditions and diseases including, but not limited to those in the following group: psoriasis; eczema; cancers involving breakpoints or deletions in chromosome 18q; squamous cell carcinomas, including carcinoma of lung, cervix and esophagus; arthritis that involves extracellular matrix destruction or formation of lesions in arthritic joints, including osteoarthritis and rheumatoid arthritis; cirrhosis; thrombosis; emphysema; angiodema; tumor growth; disorders involving vascular hemostasis; disorders involving complement activation; disorders associated with abnormal degradation of the extracellular matrix, such as tumor invasion and metastasis; disorders involving digestion; disorders involving control of fibrinolysis; disorders of the coagulation cascade; disorders associated with vasodilation in inflammation and hypertension.

The therapeutic molecule or molecules to be used will depend on the etiology of the condition to be treated and the biological pathways involved, and variants, fragments, and binding partners of Thypin polypeptides may have effects similar to or different from Thypin polypeptides. Molecules useful for manipulating Thypin levels or activities may include full-length Thypin polypeptides or fragments thereof, allelic variants, muteins, antagonists, agonists, antibodies, and binding partners of the invention, and it is understood that a specific molecule or molecules can be selected from those provided as embodiments of the invention by individuals of skill in the art, according to the biological and therapeutic considerations described herein.

Administration of Thypin Polypeptides and Antagonists Thereof

This invention provides compounds, compositions, and methods for treating a patient, preferably a mammalian patient, and most preferably a human patient, who is suffering from a medical disorder, and in particular a Thypin-mediated disorder, such as the disorders described above. Such Thypin-mediated disorders include conditions caused (directly or indirectly) or exacerbated by binding between Thypin and a binding partner. For purposes of this disclosure, the terms "illness," "disease," "medical condition," "abnormal condition" and the like are used interchangeably with the term "medical disorder." The terms "treat", "treating", and "treatment" used herein includes curative, preventative (e.g., prophylactic) and palliative or ameliorative treatment. For such therapeutic uses, Thypin polypeptides and fragments, Thypin nucleic acids encoding Thypin polypeptides, and/or agonists or antagonists of the Thypin polypeptide such as antibodies can be administered to the patient in need through well-known means. Compositions of the present invention can contain a polypeptide in any form described herein, such as native polypeptides, variants, derivatives, oligomers, and biologically active fragments. In particular embodiments, the composition comprises a soluble polypeptide or an oligomer comprising soluble Thypin polypeptides.

Therapeutically Effective Amount. In practicing the method of treatment or use of the present invention, a therapeutically effective amount of a therapeutic agent of the present invention is administered to a patient having a condition to be treated, preferably to treat or ameliorate diseases associated with the activity of a Thypin polypeptide. "Therapeutic agent" includes without limitation any of the Thypin polypeptides, fragments, and variants described herein; nucleic acids encoding Thypin polypeptides, fragments, and variants; agonists or antagonists of Thypin polypeptides such as agonistic or antagonistic antibodies specific for Thypin; Thypin polypeptide binding partners; and complexes formed from Thypin polypeptides, fragments, variants, and binding partners, etc. As used herein, the term "therapeutically effective amount" means the total amount of each therapeutic agent or other active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. The therapeutic agents provided herein may be administered in combination with other therapeutic agents, either serially, alternately, or simultaneously.

As used herein, the phrase "administering a therapeutically effective amount" of a therapeutic agent means that the patient is treated with said therapeutic agent in an amount and for a time sufficient to induce an improvement, and preferably a sustained improvement, in at least one indicator that reflects the severity of the disorder. An improvement is considered "sustained" if the patient exhibits the improvement on at least two occasions separated by one or more days, or more preferably, by one or more weeks. The degree of improvement is determined based on signs or symptoms, and determinations may also employ questionnaires that are administered to the patient, such as quality-of-life questionnaires. Various indicators that reflect the extent of the patient's illness may be assessed for determining whether the amount and time of the treatment is sufficient. The baseline value for the chosen indicator or indicators is established by examination of the patient prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as Thypin polypeptides or antagonists until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions or injuries. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Dosing. One skilled in the pertinent art will recognize that suitable dosages will vary, depending upon such factors as the nature and severity of the disorder to be treated, the patient's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose may be formulated in animal models to achieve a circulating plasma concentration range that includes the IC50 (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of therapeutic agent of the present invention with which to treat each individual patient, and may modulate the does and frequency of administration in accord with an individual patients needs.

Pharmaceutical compositions comprising Thypin or fragments thereof, a protein that is a Thypin antagonist or a protein that is a Thypin agonist should contain a dose of about 0.01 ng to about 100 mg (preferably about 0.1 ng to about 10 mg, more preferably about 0.1 microgram to about 1 mg) of polypeptide per kg body weight. In one embodiment of the invention, such compositions are administered one time per week to treat the various medical disorders disclosed herein, in another embodiment are administered at least two times per week, and in another embodiment are administered at least three times per week. If injected, the effective amount of Thypin polypeptides or antagonists per adult dose may be calculated based on body surface area, and may involve doses of 1–20 mg/m$^2$, and preferably involves doses of 5–12 mg/m$^2$. Alternatively, a flat dose may be administered, whose amount may range from 5–100 mg/dose. Exemplary dose ranges for a flat dose to be administered by subcutaneous injection are 5–25 mg/dose, 25–50 mg/dose and 50–100 mg/dose. In one embodiment of the invention, a medical disorder is treated by administering a preparation acceptable for injection containing Thypin polypeptides at a flat dose containing 1, 5, 10, 25 or 50 mg. The 1, 5, 10, 25 or 50 mg dose may be administered repeatedly, particularly for chronic conditions. If a route of administration other than injection is used, the dose is appropriately adjusted in accord with standard medical practices.

The frequency of administration and duration of the treatment may vary. In many instances, an improvement in a patient's condition will be obtained by injecting the therapeutic dose of Thypin polypeptides or Thypin antagonists one to three times per week over a period of at least three weeks, or alternatively, one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the patient's physician. The foregoing doses are examples for an adult patient who is a person who is 18 years of age or older.

For pediatric patients (age 4–17), one suitable regimen involves the subcutaneous injection of 0.4 mg/kg, up to a maximum dose of 25 mg of Thypin polypeptides or antagonists, administered by subcutaneous injection one or more times per week. If an antibody against a Thypin polypeptide is used as the Thypin polypeptide antagonist, a preferred dose range is 0.1 to 20 mg/kg, and more preferably is 1–10 mg/kg. Another preferred dose range for an anti-Thypin antibody is 0.75 to 7.5 mg/kg of body weight. Humanized antibodies are preferred, that is, antibodies in which only the antigen-binding portion of the antibody molecule is derived from a non-human source. Such antibodies may be injected or administered intravenously.

Formulations. Compositions comprising an effective amount of a Thypin polypeptide of the present invention (from whatever source derived, including without limitation from recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which may contain antioxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, Thypin for pharmaceutical compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323. Such compositions will influence the physical state, solubility, stability, rate of in vivo release, and rate of in vivo clearance, and are thus chosen according to the intended application, so that the characteristics of the carrier will depend on the selected route of administration. In one preferred embodiment of the invention, sustained-release forms of Thypin polypeptides are used. Sustained-release forms suitable for use in the disclosed methods include, but are not limited to, Thypin polypeptides that are encapsulated in a slowly-dissolving biocompatible polymer (such as the alginate microparticles described in U.S. Pat. No. 6,036,978), admixed with such a polymer (including topically applied hydrogels), and/or encased in a biocompatible semipermeable implant.

Combinations of Therapeutic Compounds. The invention further provides the administration of Thypin polypeptides, Thypin antagonists or Thypin agonists concurrently with one or more other drugs that are administered to the same patient in combination with the Thypin polypeptides, antagonists or agonists, each drug being administered according to a regimen suitable for that medicament. Generally, the additional drug is one that is effective against the same medical condition for which the Thypin is being administered. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. The pharmaceutical composition may further contain other agents which either enhance the activity of the Thypin polypeptide or compliment its activity or use in treatment. Such additional factors and/or agents may be included in the pharmaceutical composition to produce a synergistic effect with a polypeptide of the invention, or to minimize side effects. Conversely, a Thypin polypeptide, antagonist or agonist of the present invention may be included in formulations of the particular cytokine, lymphokine, chemokine, other hematopoietic factor, thrombolytic or anti-thrombotic factor, or anti-inflammatory agent to minimize side effects of the cytokine, lymphokine, chemokine, other hematopoietic factor, thrombolytic or anti-thrombotic factor, or anti-inflammatory agent. Additional examples of drugs to be administered concurrently may include but are not limited to analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, Thypin polypeptides or antagonists may be combined with a second Thypin polypeptide/antagonist, including an antibody against a Thypin polypeptide, or a Thypin polypeptide-derived peptide that acts as a competitive inhibitor of a native Thypin polypeptide.

Routes of Administration. Any efficacious route of administration may be used to therapeutically administer Thypin polypeptides or antagonists thereof, including those compositions comprising nucleic acids. Parenteral administration includes injection, for example, via intra-articular, intravenous, intramuscular, intralesional, intraperitoneal or subcutaneous routes by bolus injection or by continuous infusion, and also includes localized administration, e.g., at a site of disease or injury. Other suitable means of administration include sustained release from implants; aerosol inhalation and/or insufflation; eyedrops; vaginal or rectal suppositories; buccal preparations; oral preparations, including pills, syrups, lozenges or chewing gum; and topical preparations such as lotions, gels, sprays, ointments or other suitable techniques. Alternatively, Thypin polypeptides, antagonists or agonists may be administered by implanting cultured cells that express the polypeptide, for example, by implanting cells that express Thypin polypeptides or proteinaceous antagonists. Cells may also be cultured ex vivo in the presence of Thypin polypeptides in order to modulate their proliferation or to produce a desired effect on or activity in such cells. Treated cells can then be introduced in vivo for therapeutic purposes.

In another embodiment, the patient's own cells are induced to produce Thypin polypeptides or antagonists by transfection in vivo or ex vivo with a DNA that encodes Thypin polypeptides or antagonists. This DNA can be introduced into the patient's cells, for example, by injecting naked DNA or liposome-encapsulated DNA that encodes Thypin polypeptides or antagonists, or by other means of transfection. Nucleic acids of the invention may also be administered to patients by other known methods for introduction of nucleic acid into a cell or organism (including, without limitation, in the form of viral vectors or naked DNA). When Thypin polypeptides or antagonists are administered in combination with one or more other biologically active compounds, these may be administered by the same or by different routes, and may be administered simultaneously, separately or sequentially.

Oral Administration. When a therapeutically effective amount of a therapeutic agent of the present invention is administered orally, polypeptide of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, ethanol, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

Administration by Injection. For therapeutic agents comprising polypeptides, injection is one of the preferred routes of administration. When a therapeutically effective amount of polypeptide of the present invention is administered by intravenous, cutaneous or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Bone and Tissue Administration. For compositions of the present invention which are useful for bone, cartilage, tendon or ligament disorders, the therapeutic method includes administering the composition topically, systematically, or locally as an implant or device. When administered, the therapeutic composition for use in this invention is, of course, in a pyrogen-free, physiologically acceptable form Further, the composition may desirably be encapsulated or injected in a viscous form for delivery to the site of bone, cartilage or tissue damage. Topical administration may be suitable for wound healing and tissue repair. Therapeutically useful agents other than a polypeptide of the invention which may also optionally be included in the composition as described above, may alternatively or additionally, be administered simultaneously or sequentially with the composition in the methods of the invention. Preferably for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure polypeptides or extracellular matrix components. Other potential matrices are nonbiodegradable and chemically defined, such as sintered hydroxapatite, bioglass, aluminates, or other ceramics Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix. A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethyl-cellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the polypeptide from the polymer matrix and to provide appropriate handling of the composition, yet not so much that the progenitor cells are prevented from infiltrating the matrix, thereby providing the polypeptide the opportunity to assist the osteogenic activity of the progenitor cells.

In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-alpha and TGF-beta), and insulin-like growth factor (IGF). The dosage regimen of a polypeptide-containing pharmaceutical composition to be used in tissue regeneration will be determined by the attending physician considering various factors which modify the action of the polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Veterinary Uses. In addition to human patients, Thypin polypeptides and antagonists are useful in the treatment of disease conditions in non-human animals, such as pets (dogs, cats, birds, primates, etc.), domestic farm animals (horses cattle, sheep, pigs, birds, etc.), or any animal that suffers from a condition involving aberrant Thypin expression. In such instances, an appropriate dose may be determined according to the animal's body weight. For example, a dose of 0.2–1 mg/kg may be used. Alternatively, the dose is determined according to the animal's surface area, an exemplary dose ranging from 0.1–20 mg/m$^2$, or more preferably, from 5–12 mg/m$^2$. For small animals, such as dogs or cats, a suitable dose is 0.4 mg/kg. In a preferred embodiment, Thypin polypeptides or antagonists (preferably constructed from genes derived from the same species as the patient), is administered by injection or other suitable route one or more times per week until the animal's condition is improved, or it may be administered indefinitely.

Manufacture of Medicaments. The present invention also relates to the use of Thypin polypeptides, fragments, and variants; nucleic acids encoding Thypin polypeptides, fragments, and variants; agonists or antagonists of the Thypin polypeptides such as antibodies; Thypin polypeptide binding partners; complexes formed from Thypin polypeptides, fragments, variants, and binding partners, etc, in the manufacture of a medicament for the prevention or therapeutic treatment of each medical disorder disclosed herein.

Variations of Thypin polypeptides are provided as naturally occurring genomic variants of the Thypin sequences disclosed herein; such variations may be incorporated into a Thypin polypeptide or nucleic acid individually or in any combination, or in combination with alternative splice variation as described above.

The following examples are intended to illustrate particular embodiments and not to limit the scope of the invention.

EXAMPLE 1

Identification a New Member of the Human Serpin Family

A new serpin gene was identified and sequenced as described below. A nucleotide sequence encoding this newly discovered protein is shown in SEQ ID NO:1. This new serpin gene was named "Thypin" because it appears to be expressed primarily in epithelial tissues (see Example 2 below).

Thypin was discovered as follows. A data set was received from Celera Genomics (Rockville, Md.) containing a listing of amino acid sequences predicted to be encoded by the human genome. This data set was searched with a BLAST algorithm to identify serpin family polypeptides. IMX96867, located in R22 genomic contig 51804590, was recognized as being exon 1 of a new serpin gene. Two other serpin gene fragments, IMX96869 and IMX96874, were found to contain exons 3 and 6 of the same new serpin gene. These three exons were found to be contiguous on R22 genomic contig 51804590. Three other contiguous Thypin exons (exons 4, 5 and 7) were identified by electronic genome walking with SCCA-2 cDNA sequence on this same contig. Exon 2 was discovered by sequencing a thymus cDNA. Exon 2 was confirmed by determining that it was located between exons 1 and 3 on R22 genomic contig 51804590.

Using thymus cDNA as template, the complete coding sequence of this new serpin was determined by reverse transcriptase-PCR cloning and sequencing. This effort employed the following oligonucleotides that were designed to the 5' and 3' untranslated regions of Thypin:

```
SEQ ID NO:3:  5'  TGGTTTTAGATCGTTATAAGTTTTAC  3'

SEQ ID NO:4:  5'  CTCCAGCTCCAAAGTACTAGACACTGCTCC  3'
```

The two oligonucleotides described above were used as PCR primers to amplify cDNA corresponding to transcripts from human thymus. Using the nested primers shown below, another round of PCR was used to amplify the Thypin cDNA from the initiator methionine to the termination codon. These nested primers had the following sequences:

SEQ ID NO:5:
5' ATACTAGTAGTATGGACTCTCTTGTTACAGCAAACACC 3'

SEQ ID NO:6:
5' TAGCGGCCGCTTAAGGAGAGCAGACCCTGCCATAAAAGAG 3'

The following additional PCR primers also were used to generate cDNA encoding exons 1, 2 and 3 of Thypin.

SEQ ID NO:7:    5' ATGGACTCTCTTGTTACAGC 3'

SEQ ID NO:8:    5' CTCTCCATAAAGCCTGTTGG 3'

Sequence derived from the PCR studies confirmed the Thypin exon sequences that had initially been identified in R22 genomic contig 51804590. Exon 2 was identified in a PCR product spanning exons 1 and 3.

The gene structure of Thypin was determined by comparing the cDNA sequence shown in SEQ ID NO:1 with the R22 genomic contig 51804590. The Thypin gene was found also to be present in Genomic Contig GenBank Accession No. AC015536. The approximate positions of the exons containing Thypin coding sequence in the AC015536 contig are shown in Table 1 below, as well as the corresponding locations of these nucleotides in SEQ ID NO:1. Table 1 also indicates which amino acids are encoded by each of the seven Thypin exons.

TABLE 1

| Exon | AC015536 nts | SEQ ID NO: 1 nts | Splice Site @ | nt | AA |
|---|---|---|---|---|---|
| 1 | 154946–154779 | 1–168 | 3' | 168 | 56 |
| 2 | 152744–152610 | 169–303 | 5', 3' | 135 | 45 |
| 3 | 151497–151357 | 304–444 | 5', 3' | 141 | 47 |
| 4 | 149980–149862 | 445–562 | 5', 3' | 118 | 39.33 |
| 5 | 147080–146935 | 563–705 | 5', 3' | 143 | 47.67 |
| 6 | 145597–145430 | 706–873 | 5', 3' | 168 | 56 |

TABLE 1-continued

| Exon | AC015536 nts | SEQ ID NO: 1 nts | Splice Site @ | nt | AA |
|---|---|---|---|---|---|
| 7 | 144431–144026 | 874–1278 | 5' | 405 | 134 |

The coding region of the Thypin gene includes 7 exons and 6 introns spanning a distance of approximately 10,900 nucleotides on the AC015536 contig. The complete open reading frame of Thypin consists of 1275 nucleotides and encodes a protein containing 425 amino acids (SEQ ID NOS:1 and 2). Each intron has a consensus splice site at its 5' and 3' boundaries. It is possible that the 5' and 3' untranslated regions of the Thypin gene may extend further along the contig sequence beyond those portions that correspond to the 5' and 3' ends as indicated in Table 1.

The amino acid sequence of Thypin (SEQ ID NO:2) was compared with the amino acid sequences of other serpin family members. The alignments were performed using the GCG "pretty" multiple sequence alignment program, with amino acid similarity scoring matrix=blosum62, gap creation penalty=8, and gap extension penalty=2. Several of the serpins most closely related to Thypin were LEI (SEQ ID NO:9), PAI2 (SEQ ID NO:10), SERPINB10 (SEQ ID NO:11), SCCA-1 (SEQ ID NO:12), SCCA-2 (SEQ ID NO:13), and prostapin (SEQ ID NO:14). The sources of the LEI, PAI2, SERPINB10, SCCA-1, SCCA-2 and prostapin sequences in Table 2, respectively, were: SwissProt No. P30740; GenBank No. XP_008746; GenBank No. NP_005015; SwissProt No. P29508; SwissProt No. P48594; and GeneSeq No. Y15156. In Table 2, to facilitate the alignment the prostapin insert of amino acids 207–430 of SEQ ID NO:14 has been omitted from the displayed alignment. Table 2 includes consensus residues that are identical among at least five of the amino acid sequences in the alignment. The capitalized residues in Table 2 are those which match the consensus residues. The numbering of amino acid residues in Table 2 corresponds to the position of those residues in the Thypin amino acid sequence (SEQ ID NO:2).

TABLE 2

```
Protein
(SEQ ID NO)   1                                                              50
       LEI (9)   MeqLssANTr  FalDLFlals  ennpagNIFi  SPfSIssAma  MVfLGtrgnT
      PAI2 (10)  MedLcvANTl  FalnLFkhla  kasptqNlFl  SPwSIsstma  MVymGsrgsT
   SERPB10 (11)  MdSLatsinq  FaleLskkla  esaqgkNIFf  SswSIstsLt  iVyLGAkgtT
    SCCA-1 (12)  MnSLseANTk  FmfDLFqqfr  k.skenNIFy  SPiSItsALg  MVlLGAkdnT
    SCCA-2 (13)  MnSLvtANTk  FmfDLFqqfr  k.skenNIFy  SPiSItsALg  MVlLGAkdnT
    THYPIN (2)   MdSLvtANTk  FcfDLFqeig  kddrhkNIFf  SPlSlsaALg  MVrLGArsds
    Prstpn (14)  MgSLstANve  FclDvFkeln  snnigdNIFf  SslSllyALs  MVlLGArgeT
     consensus   M-SL--ANT-  F---DLF----  ------NIF-  SP-SI--AL-  MV-LGA---T 51                                                             100
       LEI (9)   AaQlsKtfHF  ntv.......  ..........  ..........  ..........
      PAI2 (10)  edQmaKVLqF  nevganavtp  mtpenftscg  fmqqiqkgsy  pd........
   SERPB10 (11)  AaQmaqVLqF  n.........  ......rdqg  vkcdpesekk  rK........
    SCCA-1 (12)  AqQikKVLHF  dqvtentt..  ..........  ..........  gKaatyhvdr
    SCCA-2 (13)  AqQisKVLHF  dqvtentt..  ..........  ..........  eKaatyhvdr
    THYPIN (2)   AhQideVLHF  nefsqneske  pdpclksnkq  kvladssleg  qKktteplдq
    Prstpn (14)  AeQleKVLHF  shtvds....  ..........  ...lkpgfkds  pKcs......
     consensus   A-Q--KVLHF  ----------  ----------  ----------  -k--------
```

TABLE 2-continued

```
                  101                                                           150
      LEI   (9)  .........e  evHsrFqsLn  adiNkrgasY  iLklANrLyG  EKTynFlpEf
      PAI2 (10)  .ailqaqaad  KiHssFrsLs  saiNastgnY  lLesvNkLfG  EKsasFreEY
   SERPB10 (11)  .mefnlsnse  eiHsdFqtLi  seilkpnddy  lLktANaiyG  EKTyaFhnkY
    SCCA-1 (12)  ........sg  nvHhqFqkLl  refNkstdaY  eLkiANkLfG  EKTylFlqEY
    SCCA-2 (13)  ........sg  nvHhqFqkLl  tefNkstdaY  eLkiANkLfG  EKTyqFlqEY
    THYPIN  (2)  qagslnnesg  lvscyFgqLl  skldriktdY  tLsiANrLyG  EqefpicqEY
    Prstpn (14)  .......qag  riHseFgvxf  sqiNqpdsnc  tLsiANrLyG  tKTmaFhqqy
    consensus    ----------  --H--F----  ---N-----Y  -L--AN-L-G  EKT--F--EY
                  151                                                           200
      LEI   (9)  LvstqKtYga  dlasVDFqha  sEdaRKtINq  WVkgQTeGKI  peLlasgmvd
      PAI2 (10)  irlcqKyYss  epqaVDFlec  aEeaRKkINs  WVktQTkGKI  pNLlpegsvd
   SERPB10 (11)  Ledmktyfga  epqpVnFvea  sdqiRKdINs  WVErQTeGKI  qNLlpddsvd
    SCCA-1 (12)  LdaikKfYqt  svesVDFana  pEesRKkINs  WVEsQTneKI  kNLipegnig
    SCCA-2 (13)  LdaikKfYqt  svestDFana  pEesRKkINs  WVEsQTneKI  kNLfpdgtig
    THYPIN  (2)  LdgviqfYht  tiesVDFqkn  pEksRqeINf  WVEcQTneKI  keLfskdain
    Prstpn (14)  LscseKwYqa  rlqtVDFeqs  tEetRKtINa  WVEnkTnGKv  aNLfgkstid
    consensus    L----K-Y--  ----VDF---  -E--RK-IN-  WVE-QT-GKI  -NL-------

201                                                           248
      LEI   (9)  nmTklVLVNA  iYFKGnWkdk  FmkeaTtnaP  FrlNkkdrk.  .tVkMMyQkk
      PAI2 (10)  gdTrmVLVNA  vYFKGkWktp  FekklnglyP  FrvNsaqrt.  .pVqMMylre
   SERPB10 (11)  stTrmiLVNA  lYFKGiWehq  FlvqnTtekp  FriNettsK.  .pVqMMfmkk
    SCCA-1 (12)  snTtlVLVNA  iYFKGqWekk  FnkedTkeek  FwpNkntyK.  .siqMMrQyt
    SCCA-2 (13)  ndTtlVLVNA  iYFKGqWenk  FkkenTkeek  FwpNkntyK.  .sVqMMrQyn
    THYPIN  (2)  aeTvlVLVNA  vYFKakWety  FdhenTvdaP  FclNanenK.  .sVkMMtQkg
    Prstpn (14)  pssvmVLVNA  iYFKGqWqnk  FqvreTvksP  FqlseAggKn  vtVeMMyQig
    consensus    --T--VLVNA  -YFKG-W---  F----T---P  F--N----K-  --V-MM-Q--
                  249                                                           297
      LEI   (9)  kfaygyiEdl  kcrvLElPY.  qGeeLSMviL  LPddiedest  GLkkiEeqlT
      PAI2 (10)  klnigyiEdl  kAqiLElPY.  aG.dvSMflL  LPdeiadvst  GLelLEseiT
   SERPB10 (11)  klhifhiEkp  kAvgLqlyY.  ksrdLSlliL  LPedi....n  GLeqLEkaiT
    SCCA-1 (12)  sfhfaslEdv  qAkvLEiPY.  kGkdLSMivL  LP....neid  GLqkLEeklT
    SCCA-2 (13)  sfnfallEdv  qAkvLEiPY.  kGkdLSMivL  LP....neid  GLqkLEeklT
    THYPIN  (2)  lyrigfiEev  kAqiLEmrYt  kGk.LSMfvL  LPshskdnlk  GLeeLErkiT
    Prstpn (14)  tfklafvkep  qmqvLElPYv  nnk.LSMiiL  LPvgian...  .LkqiEkqln
    consensus    -------E--  -A--LE-PY-  -G--LSM--L  LP--------  GL--LE---T 298                                                           347
      LEI   (9)  lEKLhEWTkp  eNldfieVnv  sLPRFKLEeS  YtLnSdLarl  GvqDlFNssk
      PAI2 (10)  ydKLnkWTSk  dkMaEdeVev  yiPqFKLEeh  YeLrSiLrsM  GmeDaFNkgr
   SERPB10 (11)  yEKLnEWTSa  dmMelyeVql  hLPkFKLEdS  YdLkStLssM  GmsDaFsqsk
    SCCA-1 (12)  aEKLmEWTSl  qNMrETrVdl  hLPRFKvEeS  YdLkdtLrtM  GmvDiFNgd.
    SCCA-2 (13)  aEKLmEWTSl  qNMrETcVdl  hLPRFKmEeS  YdLkdtLrtM  GmvniFNgd.
    THYPIN  (2)  yEKmvaWsSs  eNMsEesVvl  sfPRFtLEdS  YdLnSiLqdM  GitDiFdetr
    Prstpn (14)  sgtfhEWTSs  sNMmEreVev  hLPRFKLEtk  YeLnSlLksl  GvtDlFNqvk
    consensus    -EKL-EWTS-  -NM-E---V--  -LPRFKLE-S  Y-L-S-L--M  G--D-FN---
                  348                                                           396
      LEI   (9)  ADLSGMSgar  difiSkivHK  sFVEVnEEGT  EAAAATagia  tfCmlmp.ee
      PAI2 (10)  AnfSGMSern  dLfLSevfHq  amVdVnEEGT  EAAAgTggvm  tgRtghg.gp
   SERPB10 (11)  ADfSGMSsar  nLfLSnvfHK  aFVEinEqGT  EAAAgsgsei  dirirvp.si
    SCCA-1 (12)  ADLSGMtgsr  gLvLSgvlHK  aFVEVtEEGa  EAAAATavvg  fgSspastne
    SCCA-2 (13)  ADLSGMtwsh  gLsvSkvlHK  aFVEVtEEGv  EAAAATavvv  velSspstne
    THYPIN  (2)  ADLtGiSpsp  nLySkiiHK   tFVEVdEnGT  qAAAATgavv  seRslrsw.v
    Prstpn (14)  ADLSGMSptk  gLySkaiHK   syldVsEEGT  EAAAATgdsi  avkslp.mra
    consensus    ADLSGMS---  -L-LS---HK  -FVEV-EEGT  EAAAAT----  --.-------
```

TABLE 2-continued

|  | 397 |  | 425 |
|---|---|---|---|
| LEI (9) | nFtAdHPFLF | FIRHNssgsI | LFlGRfsSP |
| PAI2 (10) | qFvAdHPFLF | lImHkiTNcI | LFfGRfsSP |
| SERPB10 (11) | eFnANHPFLF | FIRHNkTNtI | LFyGRlcSP |
| SCCA-1 (12) | eFhcNHPFLF | FIRqNkTNsI | LFyGRfsSP |
| SCCA-2 (13) | eFccNHPFLF | FIRqNkTNsI | LFyGRfsSP |
| THYPIN (2) | eFnANHPFLF | FIRHNkTqtI | LFyGRvcSP |
| Prstpn (14) | qFkANHPFLF | FIRHthTNtI | LFcGklaSP |
| consensus | -F-ANHPFLF | FIRHN-TN-I | LF-GR---SP |

▬ : facultative secretion signal (amino acids 28–42 of SEQ ID NO:2)
▪ ▪ ▪ : interhelical variable loop (amino acids 61–107 of SEQ ID NO:2)
▪ ▪ ▪ : reactive site loop ('RSL") (amino acids 374–395 of SEQ ID NO:2)
• C, S, R : P1 reactive residue
▬ : serpin signature consensus (amino acids 398–408 of SEQ ID NO:2)
Δ : deletion of prostapin amino acids 207–430 (amino acids 207–430 of SEQ ID NO:14)

The closest match found with Thypin among the known serpins in the public databases was SCCA-2. A GAP alignment was performed comparing the Thypin amino acid sequence shown in SEQ ID NO:2 and the SCCA-2 amino acid sequence, which is given in SEQ ID NO:13. This GAP comparison employed the BLOSUM62 amino acid substitution matrix, and used a gap weight of 8 and a length weight of 2. The results of this alignment indicated that the SCCA-2 and Thypin polypeptides have a 59.28% similarity and a 51.03% identity.

Amino acid substitutions and other alterations (deletions, insertions, etc.) to Thypin amino acid sequences (e.g. SEQ ID NO:2) are predicted to be more likely to alter or disrupt Thypin polypeptide activities if they result in changes to the capitalized residues of the amino acid sequences as shown in Table 2, and particularly if those changes do not substitute an amino acid of similar structure (such as substitution of any one of the aliphatic residues—Ala, Gly, Leu, Ile, or Val—for another aliphatic residue), or a residue present in other serpin polypeptides at that conserved position. Conversely, if a change is made to a Thypin amino acid sequence resulting in substitution of the residue at that position in the alignment from one of the other Table 2 serpin polypeptide sequences, it is less likely that such an alteration will affect the function of the altered Thypin polypeptide. For example, the consensus residue corresponding to amino acid 382 of Thypin in Table 2 is alanine, but PAI2 and SERPINB10 have a glycine at that position. Thus, substitution of glycine for the alanine at position 382 of Thypin is less likely to alter the function of the polypeptide than substitution of a very different amino acid such as proline, tryptophan or tyrosine.

In addition, a partial human cDNA clone (AA242969) was identified in the GenBank dbEST database that has 95% identity to amino acids 69–250 of the Thypin polypeptide shown in SEQ ID NO:2. This region of Thypin includes the above-discused Thypin insertion, which is located at amino acids 61–107 of SEQ ID NO:2. The region of Thypin corresponding to amino acids 108–373 of SEQ ID NO:2 corresponds to the ov-serpin structural core, as discussed above, thus this EST polypeptide partially overlaps the Thypin structural core region. This EST protein differs from Thypin at eight amino acid residues, thus suggesting that EST AA242969 may represent a segment of an allelic variant of Thypin. Alternatively, one or more of these eight differences may be due to sequencing errors in determining the corresponding EST cDNA sequence. The locations of these eight differences correspond to amino acids 109, 115, 118, 126, 127, 216, 246 and 248 of SEQ ID NO:2. The amino acids present in the EST at those locations are, respectively, threonine, asparagine, lysine, phenylalanine, arginine, isoleucine, proline and phenylalanine, whereas in Thypin the corresponding amino acids, respectively, are serine, tyrosine, glutamine, isoleucine, lysine, lysine, glutamine and tyrosine. The polypeptide predicted by EST AA242969 lacks an RSL, thus cannot fold into a serpin structure nor can it exhibit any bioactivity associated with the Thypin RSL.

EXAMPLE 2

Expression in Cells and Tissues of Thypin mRNA

Oligonucleotides based on the Thypin coding sequences were used in reverse transcriptase PCR reactions to amplify panels of cDNA to determine the expression profile of Thypin. For this purpose, a pair of oligonucleotide PCR primers (SEQ ID NO:7 and SEQ ID NO:8) were used that amplify exons 1, 2 and 3. These oligonucleotides were used to amplify the Celera panel of cDNAs (Bill Lawrence, VM). By analyzing the reverse transcriptase PCR products, Thypin expression was detected in a wide variety of fetal cells and adult cells, including the following: bronchial epithelium; prostate epithelium; breast epithelium; and small airway epithelium. In addition, Thypin is expressed in the following epithelial tissues: prostate; testis; thymus; tonsil; skin; keratinocytes; cervix; fetal small intestine; and esophagus. In addition, Thypin is expressed in the following carcinoma and transformed cell lines: lung epithelial carcinoma (A549); B cell lymphoma (Akata, Nalm6, Namalwa); cancer cells of monocytic origin (U937, Thp-1, AML5); tumor xenografts (colon, pancreas, prostate). Thypin expression also was observed in miscellaneous tumors originating from lung and esophagus.

EXAMPLE 3

Host Cells Expressing Recombinant Thypin

To express Thypin protein, the full-length Thypin cDNA was PCR amplified with SpeI (5') and NotI (3') restriction endonuclease sites using olignucleotide primers corresponding to SEQ ID NOs 5 and 6. The Thypin gene was cloned into an intermediate cloning vector, placing the gene downstream of the IgKappa signal sequence, a short FLAG® tag (DYKD), and a poly-HIS tag. This entire fusion construct was subcloned into pDC412 as a SalI-NotI fragment. The amino acids GTSS were used as a spacer between the poly-HIS and the Thypin coding sequences. The IdKappa signal was included to direct the expressed protein into the extracellular compartment, that is, to ensure secretion of the expressed Thypin. The amino acid sequence of the fusion construct up to the initiator methionine of Thypin is shown as follows:

METDTLLLWVLLLWVPGSTGDYKDEGSHHHHHHGTSS-Thypin

The 37-amino-acid N-terminal fusion construct sequence shown at the left above is provided as SEQ ID NO:15. This pDC412-Thypin plasmid was transfected into COS-1 monkey kidney cells for expression of secreted Thypin polypeptide.

Transfected cell lysates and supernatants will be harvested, purified and analyzed for Thypin expression by conventional methods including, but not limited to, centrifugation, size exclusion filtration and chromotography, ion exchange chromatography, affinity chromatography, SDS-PAGE, isoelectric focusing, two-dimensional electrophoresis, western blot analysis, radionuclide labeling, affinity-tag labeling, immunoprecipitation and affinity-tag precipitation. Purified protein can be examined for post-translational modification, including phosphorylation and glycosylation. Purified protein will be tested for heat and denaturation-resistant complex formation with a variety of proteases. The inhibitory activity of Thypin may be stabilized or augmented by the addition of cofactors such as polysulfated oligosaccharides as discussed in Potempa et al. (1994).

EXAMPLE 4

Monoclonal Antibodies That Bind Polypeptides of the Invention

This example illustrates a method for preparing monoclonal antibodies that bind Thypin polypeptides. Other conventional techniques may be used, such as those described in U.S. Pat. No. 4,411,993. Suitable immunogens that may be employed in generating such antibodies include, but are not limited to, purified Thypin polypeptide, an immunogenic fragment thereof, and cells expressing high levels of Thypin polypeptide or an immunogenic fragment thereof. Immunogenic fragments generally contain at least 12 or more amino acids. DNA encoding a Thypin polypeptide can also be used as an immunogen, for example, as reviewed by Pardoll and Beckerleg in *Immunity* 3: 165, 1995.

Rodents (BALB/c mice or Lewis rats, for example) are immunized with Thypin polypeptide immunogen emulsified in an adjuvant (such as complete or incomplete Freund's adjuvant, alum, or another adjuvant, such as Ribi adjuvant R700 (Ribi, Hamilton, Mont.)), and injected in amounts ranging from 10–100 µg subcutaneously or intraperitoneally. DNA may be given intradermally (Raz et al., 1994, *Proc. Natl. Acad. Sci. USA* 91: 9519) or intamuscularly (Wang et al., 1993, *Proc. Natl. Acad. Sci. USA* 90: 4156); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision to test for Thypin polypeptide antibodies by dot-blot assay, ELISA (enzyme-linked immunosorbent assay), immunoprecipitation, or other suitable assays, such as FACS analysis of inhibition of binding of Thypin polypeptide to a Thypin polypeptide binding partner. Following detection of an appropriate antibody titer, positive animals are provided one last intravenous injection of Thypin polypeptide in saline. Three to four days later, the animals are sacrificed, and spleen cells are harvested and fused to a murine myeloma cell line, e.g., NS1 or preferably P3X63Ag8.653 (ATCC CRL-1580). These cell fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells may be screened by ELISA for reactivity against purified Thypin polypeptide by adaptations of the techniques disclosed in Engvall et al., (*Immunochem.* 8: 871, 1971) and in U.S. Pat. No. 4,703,004. A preferred screening technique is the antibody capture technique described in Beckmann et al., (*J. Immunol.* 144: 4212, 1990). Thypin-specific antibodies will bind Thypin but not other serpins including SCCA-1, SCCA-2, hurpin, prostapin, bomapin, PAI2 or LEI. Hybridoma cells producing Thypin-specific antibodies can be injected intraperitoneally into syngeneic rodents to produce ascites containing high concentrations (for example, greater than 1 milligram per milliliter) of anti-Thypin polypeptide monoclonal antibodies. Alternatively, hybridoma cells can be grown in vitro in flasks or roller bottles by various techniques. Monoclonal antibodies can be purified by ammonium sulfate precipitation, followed by gel exclusion chromatography. Alternatively, affinity chromatography based upon binding of antibody to protein A or protein G can also be used, as can affinity chromatography based upon binding to Thypin polypeptide.

EXAMPLE 5

Chromosome Mapping

The Thypin gene was mapped to a human chromosome using the BLAST probram on the NCBI Human Genome mapping resource webpage. Results of this BLAST analysis indicated that Thypin is located within the serpin cluster at human chromosome 18q21.3, and that it maps between the hurpin (located at 18q21.3–q22; Spring et al., *Biochem Biophys Res Com* 264:299 (1999)) and maspin genes (Schneider et al., *Proc Natl Acad Sci USA* 92:3147 (1995)). Serpins that map to 18q21.3 include: SerpinB5 (PI-5, maspin); SerpinB13 (PI-13, hurpin, headpin); SerpinB3 (SCCA-1); Serpin B7 (PI-11, megsin); Serpin B2 (PAI-2); Serpin B10 (PI-10, bomapin); and SerpinB8 (PI-8, CAP2). These serpins, listed in consecutive order distal to the centromere, are located on NCBI human genomic 18q contig NT_010986.2.

EXAMPLE 6

Analysis of Thypin Expression by Real-time Quantitative PCR

RNA samples were obtained from a variety of tissue sources and from cells or tissues treated with a variety of compounds; these RNA samples included commercially available RNA (Ambion, Austin, Tex.; Clontech Laboratories, Palo Alto, Calif.; and Stratagene, La Jolla, Calif.). The RNA samples were DNase treated (part # 1906, Ambion, Austin, Tex.), and reverse transcribed into a population of cDNA molecules using TaqMan Reverse Transcription Reagents (part # $N_8O_{8-0234}$, Applied Biosystems, Foster City, Calif.) according to the manufacturers instructions using random hexamers. Each population of cDNA molecules was placed into specific wells of a multi-well plate at either 5 ng or 20 ng per well and run in triplicate. Pooling was used when same tissue types and stimulation conditions were applied but collected from different donors. Negative control wells were included in each multi-well plate of samples.

Sets of probes and oligonucleotide primers complementary to mRNAs encoding Thypin polypeptides were designed using Primer Express software (Applied Biosystems, Foster City, Calif.) and synthesized, and PCR conditions for these probe/primer sets were optimized to produce a steady and logarithmic increase in PCR product every thermal cycle between approximately cycle 20 and cycle 36. The forward primer used was

```
5'-AACGACAGAGCCTCTGGATCAG-3'    (SEQ ID NO:16)
``` at a concentration of 900 nM; the reverse primer used was

```
5'-GAGAAGCTGCCCAAAGTAGCA-3'    (SEQ ID NO:17)
``` at a concentration of 300 nM. The FAM-labeled probe used for Thypin was

```
5'-CAGTCCGCTCTCATTGTTTAAGGACCCAG-3'    (SEQ ID NO:18)
``` at a concentration of 200 nM. Oligonucleotide primer sets complementary to 18S RNA and to mRNAs encoding certain 'housekeeper' proteins—beta-actin, HPRT (hypoxanthine phosphoribosyltransferase), DHFR (dihydrofolate reductase), PKG (phosphoglycerate kinase), and GAPDH (glyceraldehyde-3-phosphate dehydrogenase)—were synthesized and PCR conditions were optimized for these primer sets also. For example, forward and reverse primer concentrations for the housekeeping gene HPRT was 300 nM each, and VIC labeled probe (Applied Biosystems, Foster City, Calif.) was used at 200 nM. Multiplex TAQMAN PCR reactions using both Thypin and HPRT probe/primer sets were set up in 25-microliter volumes with TAQMAN Universal PCR Master Mix (part # 4304437, Applied Biosystems, Foster City, Calif.) on an Applied Biosystems Prism 7700 Sequence Detection System. Threshold cycle values ($C_T$) were determined using Sequence Detector software version 1.7a (Applied Biosystems, Foster City, Calif.), and delta $C_T$ (the average FAM value minus the average VIC value) was calculated and transformed to $2E(-dC_T)$, which is 2 to the minus delta $C_T$, for relative expression comparison of Thypin to HPRT.

Analysis of Thypin expression relative to HPRT expression in a variety of adult and fetal RNA samples indicated that Thypin is expressed less abundantly than HPRT in a few adult and fetal tissues, with the lowest relative expression in adult testes and uterus (see below); a ratio of 0.00710639 indicates that the expression of Thypin is less than 1% of that of HPRT. In contrast, Thypin is expressed about 28-fold more abundantly than HPRT in adult skin.

| Sample | Thypin Avg CT | HPRT Avg CT | Ratio of Thypin: HPRT | Minimum (Minus Err) | Maximum (Plus Err) |
|---|---|---|---|---|---|
| Adult Testis | 34.3867 | 27.25 | 0.00710639 | 0.00624469 | 0.008087 |
| Adult Uterus | 32.9067 | 30.067 | 0.13966089 | 0.12738358 | 0.1531215 |
| Adult Thymus | 31.8633 | 30.393 | 0.3609823 | 0.33180107 | 0.39273 |
| Fetal Colon | 31.56 | 30.103 | 0.36433395 | 0.3287549 | 0.4037635 |
| Fetal Skeletal Muscle | 31.73 | 30.407 | 0.39961057 | 0.33446684 | 0.4774423 |
| Adult Skin | 25.1133 | 29.94 | 28.3773245 | 25.9267212 | 31.05956 |

Analysis of Thypin expression relative to HPRT expression in RNA samples from human mesenchymal stem cells undergoing differentiation into bone indicated that Thypin expression increases during differentiation, but is still expressed at much lower levels than HPRT (see below).

| Sample | Thypin Avg CT | HPRT Avg CT | Ratio of Thypin: HPRT | Minimum (Minus Err) | Maximum (Plus Err) |
|---|---|---|---|---|---|
| MSC Bone day 0 | 39.3633 | 29.053 | 0 | 0 | 0 |
| MSC Bone 24 h | 35.15 | 29.24 | 0.0166308 | 0.0131106 | 0.0210961 |
| MSC Bone 1 wk | 34.8533 | 29.977 | 0.034039 | 0.0311515 | 0.0371942 |
| MSC Bone 4.5 wk | 34.9733 | 30.613 | 0.0486978 | 0.0381139 | 0.0622207 |

Thypin expression relative to HPRT expression was analyzed in RNA samples from lung epithelial cells of normal human bronchial tissue ("NHBE") exposed to a variety of cytokine treatments (see below). This experiment shows that treatment with a combination of interleukin-4 (IL-4) and interleukin-13 (IL-13) increased Thypin expression, while treatment with interferon-gamma (IFNg) or a combination of interleukin-1 (IL-1), interleukin-18 (IL-18), and tumor necrosis factor alpha (TNFa) reduced Thypin expression. Furthermore, the specific upregulation of Thypin by the IL-4 and IL-13 combination was also observed in experiments with primary lung small airway epithelial cells (SAEC) and with lung adenocarcinoma epithelial cells (Calu3). These results suggest that upregulation of the protease inhibitor Thypin may be involved in lung epithelial response to inflammation-induced proteases.

| Sample | Thypin Avg CT | HPRT Avg CT | Ratio of Thypin: HPRT | Minimum (Minus Err) | Maximum (Plus Err) |
|---|---|---|---|---|---|
| NHBE no stim | 31.4233 | 29.203 | 0.2146414 | 0.1945253 | 0.2368376 |
| NHBE IL4/IL13 | 31.11 | 29.757 | 0.3913867 | 0.370097 | 0.4139011 |
| NHBE IL1/IL18/TNFa | 32.0967 | 29.347 | 0.1486509 | 0.1268492 | 0.1741996 |
| NHBE gIFN | 33.98 | 30.167 | 0.0711332 | 0.0629347 | 0.0803997 |
| SAEC no stim | 36.9367 | 29.13 | 0 | 0 | 0 |
| SAEC IL4/IL13 | 34.5667 | 29.037 | 0.0216423 | 0.0164463 | 0.02848 |
| SAEC IL1/IL18/TNFa | 36.3967 | 28.533 | 0 | 0 | 0 |
| SAEC IFNg | 38.39 | 28.987 | 0 | 0 | 0 |
| Calu3 no stim | 38.13 | 28.527 | 0 | 0 | 0 |
| Calu3 IL4/IL13 | 35.8167 | 28.88 | 0.0081631 | 0.0070136 | 0.009501 |
| Calu3 IL1/IL18/TNFa | 38.21 | 28.22 | 0 | 0 | 0 |
| Calu3 IFNg | 39.5 | 28.257 | 0 | 0 | 0 |

EXAMPLE 7

Identification of Mouse Ov-serpin Genes by Synteny Analysis

We have identified a mouse Thypin homolog and four new mouse ov-serpin genes that are homologous to human SERPINB3, SERPINB4, SERPINB10, and SERPINB13. These mouse genes map to mouse chromosome 1 in a syntenic cluster of ov-serpins with similar organization to human chromosome 18. FIG. 1 shows a genetic map of the human chromosome 18 and mouse chromosome 1 ov-serpins showing extensive syntenic organization between the chromosomes. The identification of four new genomic ov-serpin sequences and previously unannotated cDNAs extends the mouse ov-serpin homology on chromosome 1 and completes the orthologous representation of the known human chromosome 18 ov-serpins.

BLAST analysis of public (NT 010986.2) and Celera Genomics (CHGD R26B, GA_X2HTBL3HLMK) genomic scaffolds located Thypin in a contiguous cluster of ten chromosome 18 ov-serpins that span a genomic region of approximately 400 kilobases. The ten ov-serpin genes identified include eight that were annotated in the public domain (SERPINB2, PAI2; SERPINB3, SCCA1; SERPINB4, SCCA2; SERPINB5, Maspin; SERPINB7, Megsin; SERPINB8, PI8; SERPINB10, Bomapin; SERPINB13, Hurpin), one found in the Derwent patent database (SERPINB11, Prostapin), and Thypin (see Table 3 for Accession numbers). Using NCBI LocusLink (SERPINB2 and SERPINB4) and BLAST analysis we compiled or identified the best matching (% amino acid identity) homologous mouse cDNAs to seven out of ten of the human chromosome 18 ov-serpins (Table 3). We did not find good mouse cDNA matches for the SERPINB3, SERPINB10, or SERPINB13 in the GenBank database. However, we did find high-identity matches for these three serpins by BLAST searching the mouse genomic database from Celera Genomics. The translated mouse protein matches to SERPINB3, SERPINB10 and SERPINB13 are named Genomicb3, Genomicb10, and Genomicb13, respectively. We also found another mouse genomic sequence that is homologous to SERPINB4 (also SERPINB3 due to their high sequence similarity) which we translated and designated Genomicb4. The predicted protein sequences for mouse Genomicb3, Genomicb4, Genomicb10, and Genomicb13, edited visually at the intron/exon junctions to give the best fit with the human sequence, are provided as SEQ ID NOs 19 through 22, respectively. Only mouse Genomicb4 (SEQ ID NO:20) and Genomicb13 (SEQ ID NO:22) appear complete. The Genomicb10 mouse protein is missing 25 amino acids of coding sequence at the splice site of exon seven. The Genomicb3 mouse sequence appears to have a stop codon after amino acid 123 of SEQ ID NO:19; whether this is an artifact due to sequencing error is not clear. Each of these mouse serpin polypeptide sequences has a predicted cleavage site in the RSL: between amino acids 352 and 353 of SEQ ID NO:19; between amino acids 352 and 353 of SEQ ID NO:20; between amino acids 332 and 333 of SEQ ID NO:21; and between amino acids 354 and 355 of SEQ ID NO:22. We have not yet confirmed that any of these putative genes encode cDNAs. However, they are useful as markers in the mouse and human chromosomal ov-serpin cluster analysis discussed below. Unique mouse genomic homologs were identified for all the chromosome 18 ov-serpins except SERPINB3 and SERPINB4. Three cDNAs are annotated as mouse homologs of SERPINB4 in NCBI LocusLink (AF063937, AK003220 and AK003650) and all are represented, at least partially, in the mouse genome. We could only find an exact genomic match for the first 176 nucleotides of AF063937 on chromosome 1 scaffold CMGD R12C GA_X5J8B7W5VAQ (1,928,040 bp), encoding a complete exon from the initiator methionine to amino acid 56. We identified an exact coding sequence match for AK003220 on mouse chromosome 1 CMGD R12C contig GA_X5J8B7W2TTH (39,633 bp) and most of AK003650 on genomic scaffold CMGD R12C GA_X5J8B7W4D6C (2,012,083 bp). We did not find the first 73 amino acid genomic coding sequence of AK003650. This places three related Serpinb4 mouse homologs in three different chromosome 1 regions that have not yet been linked. With the identification herein of Genomicb3 and Genomicb4 on GA_$_{x5}$J8B7W5VAQ, there are a total of five different mouse SERPINB3/B4 homologs on three genomic contigs/scaffolds (see Table 3).

TABLE 3

| | Human | | | Mouse | |
|---|---|---|---|---|---|
| Serpin | Accession # | Chromosome | % ID | Accession # | Chromosome |
| B2 | P05120 | 18q21.3 | 75 | NM_011111 | 1 (GA_X5J8B7W4D6C) |
| B3 | P29508 | 18q21.3 | 58 | Genomicb3[a] | 1 (GA_X5J8B7W5VAQ) |
| B4 | P48594 | 18q21.3 | 60 | AF063937[b] | 1 (GA_X5J8B7W5VAQ) |
| | | | 60 | Genomicb4[a] | 1 (GA_X5J8B7W5VAQ) |
| | | | 59 | AK003220[b] | 1 (GA_X5J8B7W2THH) |
| | | | 57 | AK003650[b] | 1 (GA_X5J8B7W4D6C) |
| B5 | P36952 | 18q21.3 | 89 | NM_009257 | 1 (GA_X5J8B7W5VAQ) |
| B7 | XP_036922 | 18q21.3 | 73 | AK014524 | 1 (GA_X5J8B7W4D6C) |
| B8 | P50452 | 18q21.3 | 78 | NM_011459 | 1 (GA_X5J8B7W4D6C) |
| B10 | P48595 | 18q21.3 | 72 | Genomicb10[a] | 1 (GA_X5J8B7W4D6C) |
| B11 | gsp|Y15155 | 18q21.3 | 64 | AK009003 | 1 (GA_X5J8B7W4D6C) |
| B12 | THYPIN | 18q21.3 | 72 | AK009018 | 1 (GA_X5J8B7W5VAQ) |
| B13 | Q9UIV8 | 18q21.3 | 74 | Genomicb13[a] | 1 (GA_X5J8B7W5VAQ) |

Human chromosome 18 ov-serpins are presented with their highest percent identity mouse sequence match (BLAST: GCG, Madison Wis.) in Table 3. Human annotated protein sequences (Human-accession #) were compared to mouse translated nucleotide sequence (Mouse-accession #). Human references, except for Thypin and Y15155 (Derwent database), are available through NCBI Protein Query, ncbi.nlm.nih.gov:80/entrez/query.fcgi?db=Protein. The mouse sequences are full-length cDNAs obtained from the NCBI, except where denoted as "Genomic" ([a]). These "Genomic" sequences are predicted full-length mouse homologies to human counterparts identified in the mouse genome (Celera Genomics, Rockville, Md.). The genomic sequence exons were spliced empirically based on best estimates from a total alignment of the human and mouse sequences. The percent sequence identities shown are for annotated human proteins compared to translated cDNA sequences, or translated genomic sequences (% ID). Complete sequence matches for all the annotated cDNAs were localized on three independent mouse chromosome 1 genomic contigs/scaffolds (Mouse-Chromosome). ([b]) AF063937, AK003220, and AK003650 are all annotated in NCBI LocusLink as mouse SerpinB4 homologs (SCCA2, LocusID 20248).

The high sequence similarity shared between human ov-serpins is also conserved in the mouse members (see Table 4 below). The upper right diagonal (bold) shows percent sequence identity for the entire protein. The lower left diagonal presents the identity throughout the RSL (P17 through P4'). Most of the highly conserved residues identified in the serpin superfamily are also conserved in both human and mouse protein sequences.

TABLE 4

Human and mouse ov-serpin amino acid sequence comparison

| | HsB3 | HsB4 | AF063937 | AK003220 | AK003650 | Genmcb3 | Genmcb4 |
|---|---|---|---|---|---|---|---|
| HsB3 | 100 | 91 | 59 | 59 | 55 | 57 | 59 |
| HsB4 | 66 | 100 | 60 | 59 | 57 | 59 | 60 |
| AF063937 | 52 | 57 | 100 | 86 | 82 | 85 | 79 |
| AK003220 | 66 | 57 | 90 | 100 | 84 | 81 | 76 |
| AK003650 | 29 | 33 | 62 | 62 | 100 | 78 | 74 |
| Genmcb3 | 43 | 43 | 62 | 62 | 38 | 100 | 78 |
| Genmcb4 | 48 | 52 | 48 | 48 | 33 | 43 | 100 |

EXAMPLE 8

Identification of Additional New Members of the Human Serpin Family

Using the same methods as were used to identify Thypin, we have identified five additional new members of the human serpin polypeptide family: IMX96506, IMX96866, IMX96983, IMX98220, and IMX 96909. Each of these new human serpins will be described in turn below.

IMX96506. The amino acid sequence of the IMX96506 polypeptide is presented in SEQ ID NO:23; SEQ ID NO:24 and SEQ ID NO:25 are subsequences of SEQ ID NO:23. SEQ ID NO:23 has an RSK sequence at amino acids 377 through 379 of SEQ ID NO:23; the cleavage site is predicted to be between Arg-377 and Ser-378. When analyzed using the GeneFold algorithm as described above, the IMX96506 polypeptide has maximal scores (scores of 999.9) in all categories to plasminogen activator inhibitor III and to alpha-antitrypsin.

IMX96866. The amino acid sequence of the IMX96866 polypeptide is presented in SEQ ID NO:26. The amino acid sequence for IMX96866 polypeptide appears incomplete, as it has an interhelical variable loop region, but does not extend to the RSL domain. However, when analyzed using the GeneFold algorithm, the IMX96866 polypeptide also has maximal scores to plasminogen activator inhibitor III and to alpha-antitrypsin. Also, IMX96866 exhibits sequence similarity to rat and mouse kallilrein binding protein.

IMX96983. The amino acid sequence of the IMX96983 polypeptide is presented in SEQ ID NO:27; SEQ ID NO:28 is a subsequence of SEQ ID NO:27. The amino acid sequence of IMX96983 polypeptide has a substantial N-terminal extension (approximately 197 amino acids) relative to the ov-serpins; also it has a 'VLK' amino acid sequence (amino acids 544 through 546 of SEQ ID NO:27) and appears to lack the characteristic C-terminal residues of the ov-serpins. However, when analyzed using the GeneFold algorithm, the IMX96983 polypeptide also has maximal scores to plasminogen activator inhibitor III and to alpha-antitrypsin in all categories. IMX96983 polypeptide exhibits similarity to nexin and neuroserpins.

IMX98220. The amino acid sequence of the IMX98220 polypeptide is presented in SEQ ID NO:29; SEQ ID NO:30 and SEQ ID NO:31 are subsequences of SEQ ID NO:29. IMX98220 polypeptide exhibits sequence similarity to cytoplasmic anti-proteinase 3 (CAP-3).

IMX96909. The amino acid sequence of the IMX96909 polypeptide is presented in SEQ ID NO:32; SEQ ID NO:33 is a human polypeptide sequence very similar to SEQ ID NO:32. SEQ ID NO:34 differs from SEQ ID NO:32 in that amino acids 252 through 262 of SEQ ID NO:32 are replaced by amino acids 252 through 257 in SEQ ID NO:34; this difference may represent a splice variation or a naturally occurring polymorphism. SEQ ID NO:35 is a subsequence of SEQ ID NO:34. When analyzed using the GeneFold algorithm, the IMX96909 polypeptide has maximal scores to plasminogen activator inhibitor III and to alpha-antitrypsin in all categories.

EXAMPLE 9

Antisense Inhibition of Thypin Nucleic Acid Expression

In accordance with the present invention, a series of oligonucleotides are designed to target different regions of the Thypin mRNA molecule, using the nucleotide sequence of SEQ ID NO:1 as the basis for the design of the oligonucleotides. The oligonucleotides are selected to be approximately 10, 12, 15, 18, or more preferably 20 nucleotide residues in length, and to have a predicted hybridization temperature that is at least 37° C. Preferably, the oligonucleotides are selected so that some will hybridize toward the 5' region of the mRNA molecule, others will hybridize to the coding region, and still others will hybridize to the 3' region of the mRNA molecule.

The oligonucleotides may be oligodeoxynucleotides, with phosphorothioate backbones (internucleoside linkages) throughout, or may have a variety of different types of internucleoside linkages. Generally, methods for the preparation, purification, and use of a variety of chemically modified oligonucleotides are described in U.S. Pat. No. 5,948,680. As specific examples, the following types of nucleoside phosphoramidites may be used in oligonucleotide synthesis: deoxy and 2'-alkoxy amidites; 2'-fluoro amidites such as 2'-fluorodeoxyadenosine amidites, 2'-fluorodeoxyguanosine, 2'-fluorouridine, and 2'-fluorodeoxycytidine; 2'-O-(2-methoxyethyl)-modified amidites such as 2,2'-anhydro[1-(beta-D-arabino-furanosyl)-5-methyluridine], 2'-O-methoxyethyl-5-methyluridine, 2'-O-methoxyethyl-5'-O-dimethoxytrityl-5-methyluridine, 3'-O-acetyl-2'-O-methoxy-ethyl-5'-O-dimethoxytrityl-5-methyluridine, 3'-O-acetyl-2'-O-methoxyethyl-5'-O-dimethoxytrityl-5-methyl-4-triazoleuridine, 2'-O-methoxyethyl-5'-O-dimethoxytrityl-5-methylcytidine, N4-benzoyl-2'-O-methoxyethyl-5'-O-dimethoxytrityl-5-methylcytidine, and N4-benzoyl-2'-O-methoxyethyl-5'-O-di -methoxytrityl-5-methylcytidine-3'-amidite; 2'-O-(aminooxyethyl) nucleoside amidites and 2'-O-(dimethylaminooxyethyl) nucleoside amidites such as 2'-(dimethylaminooxyethoxy) nucleoside amidites, 5'-O-tert-butyldiphenylsilyl-$O^{2-2'}$-anhydro-5-methyluridine, 5'-O-tert-butyl-diphenylsilyl -2'-O-(2-hydroxyethyl)-5-methyluridine, 2'-O-([2-phthalimidoxy)ethyl]-5'-t-butyldiphenyl-silyl-5-methyluridine, 5'-O-tert-butyldiphenylsilyl-2'-O-[(2-formadoximinooxy)ethyl]-5-methyluridine, 5'-O-tert-butyldiphenylsilyl-2'-O-[N,N-dimethylaminooxyethyl]-5-methyluridine, 2'-O-(dimethylaminooxyethyl)-5-methyluridine, 5'-O-DMT-2'-O-(dimethylaminooxyethyl)-5-methyluridine, and 5'-O-DMT-2'-O-(2-N,N-dimethylaminooxyethyl)-5-methyluridine-3'-[(2-cyanoethyl)-N,N-diisopropylphosphoramidite]; and 2'-(aminooxyethoxy) nucleoside amidites such as N2-isobutyryl-6-O-diphenylcarbamoyl-2'-O-(2-ethylacetyl)-5'-O-(4,4'-dimethoxytrityl)guanosine-3'-[(2-cyanoethyl) -N,N-diisopropylphosphoramidite].

Modified oligonucleosides may also be used in oligonucleotide synthesis, for example methylenemethylimino-linked oligonucleosides, also called MMI-linked oligonucleosides; methylenedimethylhydrazo-linked oligonucleosides, also called MDH-linked oligonucleosides; methylenecarbonylamino-linked oligonucleosides, also called amide-3-linked oligonucleosides; and methyleneaminocarbonyl-linked oligonucleosides, also called amide-4-linked oligonucleosides, as well as mixed backbone compounds having, for instance, alternating MMI and P=O or P=S linkages, which are prepared as described in U.S. Pat. Nos. 5,378,825, 5,386,023, 5,489,677, 5,602,240 and 5,610,289. Formacetal- and thioformacetal-linked oligonucleosides may also be used and are prepared as described in U.S. Pat. Nos. 5,264,562 and 5,264,564; and ethylene oxide linked oligonucleosides may also be used and are prepared as described in U.S. Pat. No. 5,223,618. Peptide nucleic acids (PNAs) may be used as in the same manner as the oligonucleotides described above, and are prepared in accordance with any of the various procedures referred to in Peptide Nucleic Acids (PNA): Synthesis, Properties and Potential Applications, Bioorganic & Medicinal Chemistry, 1996, 4, 5–23; and U.S. Pat. Nos. 5,539,082, 5,700,922, and 5,719,262.

Chimeric oligonucleotides, oligonucleosides, or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Some examples of different types of chimeric oligonucleotides are: [2'-O-Me]-[2'-deoxy]-[2'-O-Me] chimeric phosphorothioate oligonucleotides, [2'-O-(2-methoxyethyl)]-[2'-deoxy]-[2'-O-(methoxyethyl)] chimeric phosphorothioate oligonucleotides, and [2'-O-(2-methoxyethyl)phosphodiester]-[2'-deoxy phosphorothioate]-[2'-O-(2-methoxyethyl)phosphodiester] chimeric oligonucleotides, all of which may be prepared according to U.S. Pat. No. 5,948,680. In one preferred embodiment, chimeric oligonucleotides ("gapmers") 18 nucleotides in length are utilized, composed of a central "gap" region consisting of ten 2'-deoxynucleotides, which is flanked on both sides (5' and 3' directions) by four-nucleotide "wings". The wings are composed of 2'-methoxyethyl (2'-MOE) nucleotides. The internucleoside (backbone) linkages are phosphorothioate (P=S) throughout the oligonucleotide. Cytidine residues in the 2'-MOE wings are 5-methylcytidines. Other chimeric oligonucleotides, chimeric oligonucleosides, and mixed chimeric oligonucleotides/oligonucleosides are synthesized according to U.S. Pat. No. 5,623,065.

Oligonucleotides are preferably synthesized via solid phase P(III) phosphoramidite chemistry on an automated synthesizer capable of assembling 96 sequences simultaneously in a standard 96 well format. The concentration of oligonucleotide in each well is assessed by dilution of samples and UV absorption spectroscopy. The full-length integrity of the individual products is evaluated by capillary electrophoresis, and base and backbone composition is confirmed by mass analysis of the compounds utilizing electrospray-mass spectroscopy.

The effect of antisense compounds on target nucleic acid expression can be tested in any of a variety of cell types provided that the target nucleic acid is present at measurable levels. This can be routinely determined using, for example, PCR or Northern blot analysis. Cells are routinely maintained for up to 10 passages as recommended by the supplier. When cells reached 80% to 90% confluency, they are treated with oligonucleotide. For cells grown in 96-well plates, wells are washed once with 200 microliters OPTI-MEM-1 reduced-serum medium (Gibco BRL) and then treated with 130 microliters of OPTI-MEM-1 containing 3.75 g/mL LIPOFECTIN (Gibco BRL) and the desired oligonucleotide at a final concentration of 150 nM. After 4 hours of treatment, the medium is replaced with fresh medium. Cells are harvested 16 hours after oligonucleotide treatment. Preferably, the effect of several different oligonucleotides should be tested simultaneously, where the oligonucleotides hybridize to different portions of the target nucleic acid molecules, in order to identify the oligonucleotides producing the greatest degree of inhibition of expression of the target nucleic acid.

Antisense modulation of Thypin nucleic acid expression can be assayed in a variety of ways known in the art. For example, Thypin mRNA levels can be quantitated by, e.g., Northern blot analysis, competitive polymerase chain reaction (PCR), or real-time reverse transcriptase PCR (RT-PCR). Real-time quantitative RT-PCR is presently preferred. RNA analysis can be performed on total cellular RNA or poly(A)+ mRNA. Methods of RNA isolation and Northern blot analysis are taught in, for example, Ausubel, F. M. et al., Current Protocols in Molecular Biology, Volume 1, pp. 4.1.1–4.2.9 and 4.5.14.5.3, John Wiley & Sons, Inc., 1996. Real-time quantitative (PCR) can be conveniently accomplished using the commercially available ABI PRISM 7700 Sequence Detection System, available from PE-Applied Biosystems, Foster City, Calif. and used according to manufacturer's instructions. This fluorescence detection system allows high-throughput quantitation of PCR products. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples. Other methods of quantitative PCR analysis are also known in the art. Thypin protein levels can be quantitated in a variety of ways well known in the art, such as immunoprecipitation, Western blot analysis (immunoblotting), ELISA, or fluorescence-activated cell sorting (FACS). Antibodies directed to Thypin polypeptides can be prepared via conventional antibody generation methods such as those described herein. Immunoprecipitation methods, Western blot (immunoblot) analysis, and enzyme-linked immunosorbent assays (ELISA) are standard in the art (see, for example, Ausubel, F. M. et al., Current Protocols in Molecular Biology, Volume 2, pp. 10.16.1–10.16.11, 10.8.1–10.8.21, and 11.2.1–11.2.22, John Wiley & Sons, Inc., 1991).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule capable of hybridizing under highly stringent conditions with a complement of the nucleotide sequence of SEQ ID NO: 1, wherein said highly stringent conditions comprise hybridizing at 42° C. in 50% formamide and 6×SSC and washing at 68° C. in 0.2×SSC; wherein said nucleic acid molecule is capable of encoding a Thypin polypeptde having the amino acid sequence shown in SEQ ID NO: 2.

2. An isolated nucleic acid molecule capable of hybridizing under highly stringent conditions with a complement of the nucleotide sequence of SEQ ID NO: 1, wherein said highly stringent conditions comprise hybridizing at 42° C. in 50% formamide and 6×SSC and washing at 68° C. in 0.2 ×SSC, and wherein said nucleic acid molecule is capable of encoding a Thypin polypeptde, wherein said Thypin polypeptide has protease inhibitory activity and differs from the amino acid sequence of SEQ ID NO: 2 by the substitution, deletion or addition of five or fewer amino acids, wherein such modifications do not involve amino acids 374–395 of SEQ ID NO: 2.

3. A nucleic acid molecule according to claim 1 that comprises the nucleotide sequence as shown in SEQ ID NO:1.

4. An expression vector comprising at least one nucleic acid according to any of claims 1 through 2.

5. An isolated recombinant host cell comprising at least one nucleic acid according to any of claims 1 through 2.

6. The recombinant host cell of claim 5, wherein the nucleic acid is integrated into the host cell genome.

7. A process for producing a polypeptide encoded by the nucleic acid of any of claims 1 through 2, comprising culturing a recombinant host cell under conditions promoting expression of said polypeptide, wherein the recombinant host cell comprises at least one nucleic acid according to any of claims 1 through 2.

8. The process of claim 7 further comprising purifying said polypeptide.

* * * * *